(12) United States Patent
Paranhos-Baccala et al.

(10) Patent No.: US 8,088,910 B2
(45) Date of Patent: Jan. 3, 2012

(54) ISOLATED MULTIPLE SCLEROSIS (MS)-ASSOCIATED RETROVIRUS (MSRV) NUCLEIC ACIDS CORRESPONDING TO THE GAG REGION

(75) Inventors: Glaucia Paranhos-Baccala, Lyons (FR); Florence Komurian-Pradel, Poleymieux Au Mont D'Or (FR); Frederic Bedin, Lyons (FR); Mireille Sodoyer, Sainte Foy les Lyon (FR); Catherine Ott, Lyons (FR); Francois Mallet, Villeurbanne (FR); Herve Perron, Lyons (FR); Bernard Mandrand, Villeurbanne (FR)

(73) Assignee: Biomerieux, Marcy l'Etoile (FR)

( * ) Notice: Subject to any disclaimer, the term of this patent is extended or adjusted under 35 U.S.C. 154(b) by 0 days.

(21) Appl. No.: 12/776,893

(22) Filed: May 10, 2010

(65) Prior Publication Data

US 2010/0285448 A1    Nov. 11, 2010

Related U.S. Application Data

(62) Division of application No. 09/319,156, filed as application No. PCT/FR98/01460 on Jul. 7, 1998, now Pat. No. 7,771,927.

(30) Foreign Application Priority Data

Jul. 7, 1997 (FR) ..................... 97 08816

(51) Int. Cl.
 *C07H 21/04* (2006.01)
 *A61K 39/21* (2006.01)
(52) U.S. Cl. ............... 536/23.72; 424/207.1
(58) Field of Classification Search .................. None
 See application file for complete search history.

(56) References Cited

U.S. PATENT DOCUMENTS

| | | | | |
|---|---|---|---|---|
| 6,582,703 B2 * | 6/2003 | Perron et al. | ............... | 424/204.1 |
| 2003/0198647 A1 * | 10/2003 | Perron et al. | ............... | 424/204.1 |

FOREIGN PATENT DOCUMENTS

| | | |
|---|---|---|
| FR | 2 689 519 | 10/1993 |
| FR | 2 689 520 | 10/1993 |
| FR | 2 689 521 | 10/1993 |
| FR | 2 715 936 | 8/1995 |
| FR | 2 715 937 | 8/1995 |
| FR | 2 715 938 | 8/1995 |
| FR | 2 715 939 | 8/1995 |
| FR | 2 716 198 | 8/1995 |
| FR | 2 727 428 | 5/1996 |
| FR | 2 728 585 | 6/1996 |
| FR | 2 731 356 | 9/1996 |
| FR | 2 737 500 | 2/1997 |
| WO | WO 93/07259 | 4/1993 |
| WO | WO 93/20188 | 10/1993 |
| WO | WO 94/28138 | 12/1994 |
| WO | WO 95/21256 | 8/1995 |
| WO | WO 97/06260 | 2/1997 |
| WO | WO 98/23755 * | 6/1998 |

OTHER PUBLICATIONS

Pauley, A., "The Sequence of H. Sapiens BAC Clone RG083M05," unpublished paper, 1996, pp. 1-20.
Boysen, C. et al., "Analysis of the 1.1-Mb Human Alpha/Delta T-Cell Receptor Locus with Bacterial Artificial Chromosome Clones," Molecular Biotechnology, University of Washington Database, 1997, pp. 1-4.
Adams, M.D. et al., "Initial Assessment of Human Gene Diversity and Expression Patterns Based Upon 83 Million Nucleotides of cDNA Sequence," The Institute for Genomic Research, 1995, pp. 1-4.
La Mantia, Girolama et al., "Identification and Characterization of Novel Human Endogenous Retrosiral Sequences 1513-Prefenrtially Expressed in Undifferentiated Embryonal Carcinoma Cells," Nucleic Acids Research, vol. 19, No. 7, pp. 1520, 1997.
Perron, H. et al., "Molecular Identification of a Novel Retrovirus Repeatedly Isolated from Patients with Multiple Sclerosis," Proc. Natl. Acad. Sci. USA, vol. 94, pp. 7583-7588, 1997.
Laemmli, U. K., "Cleavage of Structural Proteins during the Assently of the Head of Bacteriophage T4," Nature, vol. 227, pp. 680-685, Aug. 15, 1970.
Towbin, Harry et al., "Electrophoretic transfer of proteins from polyacrylamide gels to nitrocellulose sheets: Procedure and some applications," Proc. Natl. Acad. Sci. USA, vol. 76, No. 9, pp. 4350-4354, Sep. 1979.
Boehringer Mannheim Biochemicals, 1994 Catalog, "Random Promed DNA Labeling Kit," p. 103.

* cited by examiner

*Primary Examiner* — Jeffrey S. Parkin
(74) *Attorney, Agent, or Firm* — Oliff & Berridge, PLC

(57) ABSTRACT

An isolated polynucleotide having a nucleotide sequence selected from the group consisting of (a) SEQ ID NO: 21, (b) the full-length sequences encoding a polypeptide having a peptide sequence selected from the group consisting of SEQ ID NOs: 25 and 26, and (c) the full-length complementary sequences to the sequences set forth in (a) or (b).

13 Claims, 33 Drawing Sheets

Fig. 2

```
             10          20          30          40          50
         1234567890  1234567890  1234567890  1234567890  1234567890
         GCTTATAGAA  GGACCCCTAG  TATGGGGTAA  TCCCCTCTGG  GAAACCAAGC    50
         A  Y  R  R    T  P  S    M  G  .    S  P  L  G    N  Q  A
          L  I  E    G  P  L  V    W  G  N    P  L  W    E  T  K  P
           L  .  K    D  P  .    Y  G  V  I    P  S  G    K  P  S

CCCAGTACTC  AGCAGGAAAA  ATAGAATAGG  AAACCTCACA  AGGACATACT   100
         P  V  L    S  R  K  N    R  I  G    N  L  T    R  T  Y  F
          Q  Y  S    A  G  K    I  E  .  E    T  S  Q    G  H  T
         P  S  T  Q    Q  E  K    .  N  R    K  P  H  K    D  I  L

TTCCTCCCCT  CCAGATGGCT  AGCCACTGAG  GAAGGAAAAA  TACTTTCACC   150
           P  P  L    Q  M  A    S  H  .  G    R  K  N    T  F  T
         F  L  P  S    R  W  L    A  T  E    E  G  K  I    L  S  P
          S  S  P    P  D  G  .    P  L  R    K  E  K    Y  F  H  L

TGCAGCTAAC  CAACAGAAAT  TACTTAAAAC  CCTTCACCAA  ACCTTCCACT   200
         C  S  .  P    T  E  I    T  .  N    P  S  P  N    L  P  L
          A  A  N    Q  Q  K  L    L  K  T    L  H  Q    T  F  H  L
           Q  L  T    N  R  N    Y  L  K  P    F  T  K    P  S  T

TAGGCATTGA  TAGCACCCAT  CAGATGGCCA  AATTATTATT  TACTGGACCA   250
         R  H  .  .    H  P  S    D  G  Q    I  I  I  Y    W  T  R
          G  I  D    S  T  H  Q    M  A  K    L  L  F    T  G  P
           .  A  L    I  A  P  I    R  W  P    N  Y  Y    L  D  Q

GGCCTTTTCA  AAACTATCAA  GAAGATAGTC  AGGGGCTGTG  AAGTGTGCCA   300
         P  F  Q    N  Y  Q    E  D  S  Q    G  L  .    S  V  P
          G  L  F  K    T  I  K    K  I  V    R  G  C  E    V  C  Q
           A  F  S    K  L  S  R    R  .  S    G  A  V    K  C  A  K

AAGAAATAAT                                                   310
         K  K  .
          R  N  N
           E  I
```

Fig. 3A

```
          10         20         30         40         50
 1234567890 1234567890 1234567890 1234567890 1234567890
 CCCTGTATCT TTAACCTCCT TGTTAAGTTT GTCTCTTCCA GAATCAAAAC    50
  P C I F   N L L   V K F   V S S   R I K T
   P V S   L T S L   L S L   S L P   E S K L
 L Y L   . P P   C . V C   L F Q   N Q N

TGTAAAACTA CAAATTGTTC TTCAAATGGA GCACCAGATG GAGTCCATGA   100
  V K L   Q I V L   Q M E   H Q M   E S M T
   . N Y   K L F   F K W S   T R W   S P .
 C K T T   N C S   S N G   A P D G   V H D

CTAAGATCCA CCGTGGACCC CTGGACCGGC CTGCTAGCCC ATGCTCCGAT   150
    K I H   R G P   L D R P   A S P   C S D
  L R S T   V D P   W T G   L L A H   A P M
   . D P   P W T P   G P A   C . P   M L R C

GTTAATGACA TTGAAGGCAC CCCTCCCGAG GAAATCTCAA CTGCACAACC   200
  V N D I   E G T   P P E   E I S T   A Q P
   L M T   L K A P   L P R   K S Q   L H N P
  . . H   . R H   P S R G   N L N   C T T

CCTACTATGC CCCAATTCAG CGGGAAGCAG TTAGAGCGGT CATCAGCCAA   250
  L L C   P N S A   G S S   . S G   H Q P T
   Y Y A   P I Q   R E A V   R A V   I S Q
  P T M P   Q F S   G K Q   L E R S   S A N

CCTCCCCAAC AGCACTTGGG TTTTCCTGTT GAGAGGGGGG ACTGAGAGAC   300
   S P T   A L G F S C   . E G G   L R D
  P P Q Q   H L G   F P V   E R G D   . E T
   L P N   S T W V   F L L   R G G   T E R Q

AGGACTAGCT GGATTTCCTA GGCCAACGAA GAATCCCTAA GCCTAGCTGG   350
   R T S W   I S .   A N E   E S L S   L A G
   G L A   G F P R   P T K   N P .   A . L G
    D . L   D F L   G Q R R   I P K   P S W
```

Fig. 3B

```
          10         20         30         40         50
 1234567890 1234567890 1234567890 1234567890 1234567890
 GAAGGTGACT GCATCCACCT CTAAACATGG GGCTTGCAAC TTAGCTCACA    400
   K V T   A S T   S K H   G A C   N L A   H T
   R . L   H P P   L N M   G L A   T . L   T
 E G D   C I H L   . T W   G L Q   L S S   H

CCCGACCAAT CAGAGAGCTC ACTAAAATGC TAATTAGGCA AAAATAGGAG    450
   R P I   R E L   T K M   L I R Q   K . E
   P D Q   S E S S   L K C   . L G   K N R R
 P T N   Q R A H   . N A N   . A   K I G G

GTAAAGAAAT AGCCAATCAT CTATTGCCTG AGAGCACAGC GGGAGGGACA    500
   V K K   . P I I   Y C L   R A Q   R E G Q
   . R N   S Q S S   I A .   E H S   G R D K
 K E I   A N H   L L P E   S T A   G G T

AGGATGGGA TATAAACCCA GGCATTCGAG CCGGCAACGG CAACCCCCTT    550
   G S G   Y K P R   H S S   R Q R   Q P P L
   D R D   I N P   G I R A   G N G   N P L
 R I G I   . T Q   A F E   P A T A   T P F

TGGGTCCCCT CCCTTTGTAT GGGCGCTCTG TTTTCACTCT ATTTCACTCT    600
   G P L   P L Y   G R S V   F T L   F H S
 W V P S   L C M   G A L   F S L Y   F T L
 G S P   P F V W   A L C   F H S   I S L Y

ATTAAATCTT GCAACTGAAA AAAAAAAAA AAAAA                    635
   I K S   C   N .   K   K K K   K
   L N L   A T E K   K K K   K
     . I L   Q L K   K K K K   K
```

Fig. 4A

```
           10         20         30         40         50
   1234567890 1234567890 1234567890 1234567890 1234567890
   ATGGCCCTCC CTTATCATAC TTTTCTCTTT ACTGTTCTCT TACCCCCTTT       50
    M  A  L  P   Y  H  T   F  L  F    T  V  L  L    P  P  F
     W  P  S   L  I  I  L   F  S   L  F  S    Y  P  L  S
      G  P  P    L  S  Y   F  S  L  Y    C  S  L    T  P  F

CGCTCTCACT GCACCCCCTC CATGCTGCTG TACAACCAGT AGCTCCCCTT      100
    A  L  T    A  P  P  P   C  C  C   T  T  S    S  S  P  Y
     L  S  L   H  P  L   H  A  A  V   Q  P  V    A  P  L
      R  S  H   C  T  P  S   M  L  L   Y  N  Q  .  L  P  L

ACCAAGAGTT TCTATGAAGA ACGCGGCTTC CTGGAAATAT TGATGCCCCA      150
     Q  E  F   L  .  R    T  R  L  P   G  N  I    D  A  P
    T  K  S  F   Y  E  E   R  G  F   L  E  I  L   M  P  H
     P  R  V   S  M  K  N   A  A  S   W  K  Y  .  C  P  I

TCATATAGGA GTTTATCTAA GGGAAACTCC ACCTTCACTG CCCACACCCA      200
    S  Y  R  S   L  S  K    G  N  S   T  F  T  A   H  T  H
     H  I  G    V  Y  L  R   E  T  P   P  S  L    P  T  P  I
      I  .  E    F  I  .   G  K  L  H   L  H  C    P  H  P

TATGCCCCGC AACTGCTATA ACTCTGCCAC TCTTTGCATG CATGCAAATA      250
    M  P  R    N  C  Y  N   S  A  T    L  C  M    H  A  N  T
     C  P  A    T  A  I    T  L  P  L   F  A  C   M  Q  I
      Y  A  P  Q  L  L  .    L  C  H    S  L  H  A   C  K  Y

CTCATTATTG GACAGGGAAA ATGATTAATC CTAGTTGTCC TGGAGGACTT      300
     H  Y  W   T  G  K    M  I  N  P   S  C  P    G  G  L
    L  I  I  G   Q  G  K  .  L  I    L  V  V  L   E  D  L
     S  L  L    D  R  E  N   D  .  S  .  L  S   W  R  T  W

GGAGCCACTG TCTGTTGGAC TTACTTCACC CATACCAGTA TGTCTGATGG      350
    G  A  T  V   C  W  T   Y  F  T    H  T  S  M    S  D  G
     E  P  L   S  V  G  L   T  S  P    I  P  V   C  L  M  G
      S  H  C    L  L  D    L  L  H  P   Y  Q  Y   V  .  W
```

Fig. 4B

```
            10         20         30         40         50
     1234567890 1234567890 1234567890 1234567890 1234567890
     GGGTGGAATT CAAGGTCAGG CAAGAGAAAA ACAAGTAAAG GAAGCAATCT      400
       G  G  I    Q  G  Q    A  R  E    K  Q  V    K  E  A  I  S
        V  E  F    K  V  R    Q  E  K    N  K  *    R  K  Q  S
      G  W  N    S  R  S    G  K  R    K  T  S    K  G  S  N  L

CCCAACTGAC CCGGGGACAT AGCACCCCTA GCCCCTACAA AGGACTAGTT      450
       Q  L  T    R  G  H    S  T  P    S  P  Y    K  G  L  V
        P  N  *    P  G  D    I  A  P    L  A  P    T  K  D  *  F
      P  T  D    P  G  T  *    H  P  *    P  L  Q    R  T  S  S

CTCTCAAAAC TACATGAAAC CCTCCGTACC CATACTCGCC TGGTGAGCCT      500
       L  S  K  L    H  E  T    L  R  T    H  T  R  L    V  S  L
        S  Q  N    Y  M  K  P    S  V  P    I  L  A    W  *  A  Y
      L  K  T    T  *  N    P  P  Y  P    Y  S    P  G  E  P

ATTTAATACC ACCCTCACTC GGCTCCATGA GGTCTCAGCC CAAAACCCTA      550
       F  N  T    T  L  T  R    L  H  E    V  S  A    Q  N  P  T
        L  I  P    P  S  L    G  S  M  R    S  Q  P    K  T  L
      I  *  Y  H    P  H  S    A  P  *    G  L  S    P  K  P  Y

CTAACTGTTG GATGTGCCTC CCCCTGCACT TCAGGCCATA CATTTCAATC      600
       N  C  W    M  C  L    P  L  H  F    R  P  Y    I  S  I
        L  T  V  G    C  A  S    P  C  T    S  G  H  T    F  Q  S
      *  L  L    D  V  P  P    P  A  L    Q  A  I    H  F  N  P

CCTGTTCCTG AACAATGGAA CAACTTCAGC ACAGAAATAA ACACCACTTC      650
       P  V  P  E    Q  W  N    N  F  S    T  E  I  N    T  T  S
        L  F  L    N  N  G    T  S  A    Q  K  *    T  P  L  P
      C  S  *    T  M  E    Q  L  Q  H    R  N  K    H  H  F

CGTTTTAGTA GGACCTCTTG TTTCCAATCT GGAAATAACC CATACCTCAA      700
       V  L  V    G  P  L    V  S  N  L    E  I  T    H  T  S  N
        F  *  *    D  L  L    F  P  I  W    K  *  P    I  P  Q
      R  F  S  R    T  S  C    F  Q  S    G  N  N  P    Y  L  K
```

Fig. 4C

```
          10         20         30         40         50
 1234567890 1234567890 1234567890 1234567890 1234567890
 ACCTCACCTG TGTAAAATTT AGCAATACTA TAGACACAAC CAGCTCCCAA     750
   L  T  C    V  K  F    S  N  T    I  D  T  T    S  S  Q
 T  S  P  V    .  N  L    A  I  L    .  T  Q  P    A  P  N
   P  H  L    C  K  I    .  Q  Y  Y    R  H  N    Q  L  P  M

TGCATCAGGT GGGTAACACC TCCCACACGA ATAGTCTGCC TACCCTCAGG     800
   C  I  R  W    V  T  P    P  T  R    I  V  C  L    P  S  G
 A  S  G    G  .  H  L    P  H  E    .  S  A    Y  P  Q  E
   H  Q  V    G  N  T    S  H  T  N    S  L  P    T  L  R

AATATTTTTT GTCTGTGGTA CCTCAGCCTA TCATTGTTTG AATGGCTCTT     850
   I  F  F    V  C  G  T    S  A  Y    H  C  L    N  G  S  S
 Y  F  L    S  V  V    P  Q  P  I    I  V  .    M  A  L
   N  I  F  C    L  W  Y    L  S  L    S  L  F  E    W  L  F

CAGAATCTAT GTGCTTCCTC TCATTCTTAG TGCCCCCTAT GACCATCTAC     900
   E  S  M    C  F  L    S  F  L  V    P  P  M    T  I  Y
 Q  N  L  C    A  S  S  H  S    .  C  P  L    .  P  S  T
   R  I  Y    V  L  P  L    I  L  S    A  P  Y    D  H  L  H

ACTGAACAAG ATTTATACAA TCATGTCGTA CCTAAGCCCC ACAACAAAAG     950
   T  E  Q  D    L  Y  N    H  V  V    P  K  P  H    N  K  R
 L  N  K    I  Y  T  I    M  S  Y    L  S  P    T  T  K  E
   .  T  R    F  I  Q    S  C  R  T    .  A  P    Q  Q  K

AGTACCCATT CTTCCTTTTG TTATCAGAGC AGGAGTGCTA GGCAGACTAG    1000
   V  P  I    L  P  F  V    I  R  A    G  V  L    G  R  L  G
 Y  P  F    F  L  L    L  S  E  Q    E  C  .    A  D  .
   S  T  H  S    S  F  C    Y  Q  S    R  S  A  R    Q  T  R

GTACTGGCAT TGGCAGTATC ACAACCTCTA CTCAGTTCTA CTACAAACTA    1050
   T  G  I    G  S  I    T  T  S  T    Q  F  Y    Y  K  L
 V  L  A  L    A  V  S    Q  P  L    L  S  S  T    T  N  Y
   Y  W  H    W  Q  Y    H  N  L  Y    S  V  L    L  Q  T  I
```

Fig. 4D

```
              10         20         30         40         50
         1234567890 1234567890 1234567890 1234567890 1234567890
         TCTCAAGAAA TAAATGGTGA CATGGAACAG GTCACTGACT CCCTGGTCAC     1100
          S Q E I    N G D M E Q  V T D S    L V T
         L K K       . M V T    W N R       S L T    P W S P
           S R N       K W        . H G T G   H .     L P G H

CTTGCAAGAT CAACTTAACT CCCTAGCAGC AGTAGTCCTT CAAAATCGAA     1150
          L Q D      Q L N S    L A A       V V L    Q N R R
         C K I      N L T      P . Q Q      . S F    K I E
           L A R S    T . L      P S S       S S P S   K S K

GAGCTTTAGA CTTGCTAACC GCCAAAAGAG GGGGAACCTG TTTATTTTTA     1200
          A L D      L L T      A K R G      G T C    L F L
         E L . T    C . P       P K E       G E P V   Y F .
           S F R     L A N R     Q K R       G N L    F I F R

GGAGAAGAAC GCTGTTATTA TGTTAATCAA TCCAGAATTG TCACTGAGAA     1250
          G E E R    C Y Y      V N Q       S R I V   T E K
         E K N      A V I M    L I N        P E L    S L R K
           R R T     L L L C     . S I       Q N C    H . E

AGTTAAAGAA ATTCGAGATC GAATACAATG TAGAGCAGAG GAGCTTCAAA     1300
          V K E     I R D R    I Q C       R A E      E L Q N
         L K K     F E I       E Y N V     E Q R      S F K
           S . R N   S R S       N T M       . S R G    A S K

ACACCGAACG CTGGGGCCTC CTCAGCCAAT GGATGCCCTG GGTTCTCCCC     1350
          T E R     W G L      L S Q W     M P W      V L P
         T P N A   G A S       S A N       G C P G    F S P
           H R T     L G P P     Q P M       D A L    G S P L

TTCTTAGGAC CTCTAGCAGC TCTAATATTG TTACTCCTCT TTGGACCCTG     1400
          F L G P   L A A       L I L      L L L F    G P C
         S . D     L . Q L     . Y C       Y S S     L D P V
           L R T     S S S       S N I V     T P L    W T L
```

Fig. 4E

```
          10         20         30         40         50
   1234567890 1234567890 1234567890 1234567890 1234567890
   TATCTTTAAC CTCCTTGTTA AGTTTGTCTC TTCCAGAATT GAAGCTGTAA     1450
     I  F  N    L  L  V  K   F  V  S    S  R  I    E  A  V  K
      S  L  T    S  L  L    S  L  S  L    P  E  L    K  L  .
    Y  L  .    P  P  C  .   V  C  L    F  Q  N  .    S  C  K

AGCTACAGAT GGTCTTACAA ATGGAACCCC A                          1481
     L  Q  M    V  L  Q    M  E  P
    S  Y  R  W   S  Y  K    W  N  P
    A  T  D    G  L  T  N    G  T  P
```

Fig. 5A

```
          10         20         30         40         50
  1234567890 1234567890 1234567890 1234567890 1234567890
  TCAAAATCGA AGAGCTTTAG ACTTGCTAAC CGCCAAAAGA GGGGGAACCT      50
   S K S K   S F R    L A N    R Q K R    G N L
  Q N R    R A L D    L L T    A K R    G G T C
   K I E    E L .    T C .    P    P K E    G E P

GTTTATTTTT AGGGGAAGAA TGCTGTTAGT ATGTTAATCA ATCTGGAATC     100
   F I F    R G R M    L L V    C . S    I W N H
   L F L    G E E    C C . Y    V N Q    S G I
   V Y F .    G K N    A V S    M L I N    L E S

ATTACTGAGA AAGTTAAAGA AATTTGAGAT CGAATATAAT GTAGAGCAGA     150
   Y . E    S . R    N L R S    N I M    . S R
   I T E K    V K E    I . D    R I . C    R A E
   L L R    K L K K    F E I    E Y N    V E Q R

GGACCTTCAA AACACTGCAC CCTGGGGCCT CCTCAGCCAA TGGATGCCCT     200
   G P S K    H C T    L G P    P Q P M    D A L
   D L Q    N T A P    W G L    L S Q    W M P W
   T F K    T L H    P G A S    S A N    G C P

GGACTCTCCC CTTCTTAGGA CCTCTAGCAG CTATAATATT TTTACTCCTC     250
   D S P    L L R T    S S S    Y N I    F T P L
   T L P    F L G    P L A A    I I F    L L L
   G L S P    S . D    L . Q    L . Y F    Y S S

TTTGGACCCT GTATCTTCAA CTTCCTTGTT AAGTTTGTCT CTTCCAGAAT     300
   W T L    Y L Q    L P C .    V C L    F Q N
   F G P C    I F N    F L V    K F V S    S R I
   L D P    V S S T    S L L    S L S    L P E L

TGAAGCTGTA AAGCTACAAA TAGTTCTTCA AATGGAACCC CAGATGCAGT     350
   . S C K    A T N    S S S    N G T P    D A V
   E A V    K L Q I    V L Q    M E P    Q M Q S
   K L .    S Y K    . F F K    W N P    R C S
```

Fig. 5B

```
         10         20         30         40         50
1234567890 1234567890 1234567890 1234567890 1234567890
CCATGACTAA AATCTACCGT GGACCCCTGG ACCGGCCTGC TAGACTATGC    400
 H  D  .   N  L  P  W  T  P  G   P  A  C   .  T  M  L
 M  T  K   I  Y  R   G  P  L  D  R  P  A   R  L  C
P  .  L  K  S  T  V  D  P  W   T  G  L  L  D  Y  A

TCTGATGTTA ATGACATTGA AGTCACCCCT CCCGAGGAAA TCTCAACTGC    450
 .  C  .   .  H  .   S  H  P  S  R  G  N   L  N  C
 S  D  V   N  D  I  E  V  T  P   P  E  E  I   S  T  A
L  M  L   M  T  L  K  S  P  L   P  R  K   S  Q  L  H

ACAACCCCTA CTACACTCCA ATTCAGTAGG AAGCAGTTAG AGCAGTTGTC    500
 T  T  P   T  T  L  Q  F  S  R  K  Q  L  E   Q  L  S
 Q  P  L   L  H  S  N  S  V  G  S  S  .   S  S  C  Q
N  P  Y   Y  T  P   I  Q  .  E   A  V  R   A  V  V

AGCCAACCTC CCCAACAGTA CTTGGGTTTT CCTGTTGAGA GGGTGGACTG    550
 A  N  L   P  N  S  T  W  V  F   L  L  R   G  W  T  E
 P  T  S   P  T  V   L  G  F  S   C  .  E   G  G  L
S  Q  P  P  Q  Q  Y   L  G  F   P  V  E  R  V  D  .

AGAGACAGGA CTAGCTGGAT TTCCTAGGCT GACTAAGAAT CCCNAAGCCT    600
 R  Q  D   .  L  D   F  L  G  .   L  R  I   P  K  P
 R  D  R  T   S  W  I   S  .  A  D  .  E  S  X  S  L
E  T  G   L  A  G  F  P  R  L   T  K  N   P  X  A  X

ANCTGGGAAG GTGACCGCAT CCATCTTTAA ACATGGGGCT TGCAACTTAG    650
 X  W  E  G  D  R  I   H  L  .   T  W  G  L  Q  L  S
 X  G  K   V  T  A  S  I  F  K   H  G  A   C  N  L  A
L  G  R   .  P  H   P  S  L  N   M  G  L   A  T  .

CTCACACCCG ACCAATCAGA GAGCTCACTA AAATGCTAAT CAGGCAAAAA    700
 S  H  P   T  N  Q  R  A  H  .   N  A  N   Q  A  K  T
 H  T  R   P  I  R   E  L  T  K   M  L  I  R  Q  K
L  T  P  D  Q  S  E   S  S  L   K  C  .   S  G  K  N
```

Fig. 5C

```
          10         20         30         40         50
 1234567890 1234567890 1234567890 1234567890 1234567890
CAGGAGGTAA AGCAATAGCC AATCATCTAT TGCCTGAGAG CACAGCGGGA      750
  G  G  K   A  I  A   N  H  L  L   P  E  S   T  A  G
 Q  E  V  K  Q  .  P   I  I  Y   C  L  R  A   Q  R  E
  R  R  .   S  N  S  Q   S  S  I   A  .  E   H  S  G  K

AGGACAAGGA TTGGGATATA AACTCAGGCA TTCAAGCCAG CAACAGCAAC      800
  R  T  R   I  G  I   .  T  Q  A   F  K  P   A  T  A  T
 G  Q  G   L  G  Y  K   L  R  H   S  S  Q   Q  Q  Q  P
  D  K  D   W  D  I   N  S  G  I   Q  A  S   N  S  N

CCCCTTTGGG TCCCCTCCCA TTGTATGGGA GCTCTGTTTT CACTCTATTT      850
  P  F  G   S  P  P  I   V  W  E   L  C  F   H  S  I  S
 P  L  G   P  L  P   L  Y  G  S   S  V  F   T  L  F
  P  L  W   V  P  S   H  C  M  G   A  L  F   S   L  Y  F

CACTCTATTA AATCATGCAA CTGCACTCTT CTGGTCCGTG TTTTTTATGG      900
  L  Y  .   I  M  Q   L  H  S  S   G  P  C   F  L  W
 H  S  I  K  S  C  N   C  T  L   L  V  R  V   F  Y  G
  T  L  L   N  H  A  T   A  L  F   W  S  V   F  F  M  A

CTCAAGCTGA GCTTTTGTTC GCCATCCACC ACTGCTGTTT GCCACCGTCA      950
  L  K  L  S   F  C  S   P  S  T   T  A  V   C  H  R  H
 S  S  .   A  F  V  R   H  P  P   L  L  F   A  T  V  T
  Q  A  E   L  L  F   A  I  H  H   C  C  L   P  P  S

CAGACCCGCT GCTGACTTCC ATCCCTTTGG ATCCAGCAGA GTGTCCACTG     1000
  R  P  A   A  D  F  H   P  F  G   S  S  R   V  S  T  V
 D  P  L   L  T  S   I  P  L  D   P  A  E   C  P  L
  Q  T  R  C   .  L  P   S  L  W   I  Q  Q   S  V  H  C

TGCTCCTGAT CCAGCGAGGT ACCCATTGCC ACTCCCGATC AGGCTAAAGG     1050
  L  L  I   Q  R  G   T  H  C  H   S  R  S   G  .  R
 C  S  .   S  S  E  V   P  I  A   T  P  D  Q   A  K  G
  A  P  D   P  A  R  Y   P  L  P   L  P  I   R  L  K  A
```

Fig. 5D

```
         10         20         30         40         50
1234567890 1234567890 1234567890 1234567890 1234567890
CTTGCCATTG TTCCTGCATG GCTAAGTGCC TGGGTTTGTC CTAATAGAAC   1100
 L  A  I  V  P  A  W  L  S  A  W  V  C  P  N  R  T
L  P  L  F  L  H  G  .  V  P  G  F  V  L  I  E  L
  C  H  C  S  C  M  A  K  C  L  G  L  S  .  .  N

TGAACACTGG TCACTGGGTT CCATGGTTCT CTTCCATGAC CCACGGCTTC   1150
 E  H  W  S  L  G  S  M  V  L  F  H  D  P  R  L  L
N  T  G  H  W  V  P  W  F  S  S  M  T  H  G  F
  .  T  L  V  T  G  F  H  G  S  L  P  .  P  T  A  S

TAATAGAGCT ATAACACTCA CCGCATGGCC CAAGATTCCA TTCCTTGGTA   1200
 I  E  L  .  H  S  P  H  G  P  R  F  H  S  L  V
.  .  S  Y  N  T  H  R  M  A  Q  D  S  I  P  W  Y
  N  R  A  I  T  L  T  A  W  P  K  I  P  F  L  G  I

TCTGTGAGGC CAAGAACCCC AGGTCAGAGA ANGTGAGGCT TGCCACCATT   1250
 S  V  R  P  R  T  P  G  Q  R  X  .  G  L  P  P  F
L  .  G  Q  E  P  Q  V  R  E  X  E  A  C  H  H  L
  C  E  A  K  N  P  R  S  E  X  V  R  L  A  T  I

TGGGAAGTGG CCCACTGCCA TTTTGGTAGC GGCCCACCAC CATCTTGGGA   1300
 G  K  W  P  T  A  I  L  V  A  A  H  H  H  L  G  S
G  S  G  P  L  P  F  W  .  R  P  T  T  I  L  G
  W  E  V  A  H  C  H  F  G  S  G  P  P  P  S  W  E

GCTGTGGGAG CAAGGATCCC CCAGTAACA                          1329
 C  G  S  K  D  P  P  V  T
A  V  G  A  R  I  P  Q  .
  L  W  E  Q  G  S  P  S  N
```

Fig. 6A

```
         10         20         30         40         50
1234567890 1234567890 1234567890 1234567890 1234567890
CCTAGAACGT ATTCTGGAGA ATTGGACCA  ATGTGACACT CAGACGCTAA    50
 P  R  T  Y  S  G  E   L  G  P   M  .  H   S  D  A  K
  L  E  R  I  L  E  N  W  D  Q   C  D  T   Q  T  L  R
   .  N  V  F  W  R   I  G  T  N  V  T  L   R  R  .

GAAAGAAACG ATTTATATTC TTCTGCAGTA CCGCCTGGCC ACAATATCCT    100
 K  E  T  I  Y  I  L   L  Q  Y   R  L  A   T  I  S  S
  K  K  R  F  I  F   F  C  S  T   A  W  P   Q  Y  P
   E  R  N  D  L  Y  S  S  A  V   P  P  G   H  N  I  L

CTTCAAGGGA GAGAAACCTG GCTTCCTGAG GAAGTATAA  ATTATAACAT    150
 S  R  E  R  N  L  A  S  .  G   K  Y  K   L  .  H
  L  Q  G  R  E  T  W  L  P  E   G  S  I  N  Y  N  I
   F  K  G  E  K  P   G  F  L  R  E  V  .   I  I  T  S

CATCTTACAG CTAGACCTCT TCTGTAGAAA GGAGGGCAAA TGGAGTGAAG    200
 H  L  T  A  R  P  L   L  .  K   G  G  Q   M  .  S
  I  L  Q  L  D  L  F   C  R  K   E  G  K   W  S  E  V
   S  Y  S  .  T  S   S  V  E  R  R  A  N   G  V  K

TGCCATATGT GCAAACTTTC TTTTCATTAA GAGACAACTC ACAATTATGT    250
 A  I  C  N  F  L   F  I  K   R  Q  L   T  I  M  .
  P  Y  V  Q  T  F   F  S  L  R   D  N  S   Q  L  C
   C  H  M  C  K  L  S  F  H  .   E  T  T   H  N  Y  V

AAAAAGTGTG GTTATGCCC  TACAGGAAGC CCTCAGAGTC CACCTCCTTA    300
 K  V  W  F  M  P   Y  R  K  P   S  E  S   T  S  L
  K  K  C  G  L  C  P  T  G  S   P  Q  S  P   P  P  Y
   K  S  V  V  Y  A  L  Q  E  A   L  R  V   H  L  P  T

CCCCAGCGTC CCCTCCCGA  CTCCTTCCTC AACTAATAAG GACCCCCCTT    350
 P  Q  R  P  L  P  D   S  F  L   N  .  .   G  P  P  F
  P  S  V  P  S  P  T   P  S  S   T  N  K   D  P  P  L
   P  A  S  P  P  R   L  L  P  Q  L  I  R   T  P  L

TAACCCAAAC GGTCCAAAAG GAGATAGACA AAGGGGTAAA CAATGAACCA    400
 N  P  N  G  P  K  G   D  R  Q   R  G  K   Q  .  T  K
  T  Q  T  V  Q  K   E  I  D  K   G  V  N   N  E  P
   .  P  K  R  S  K  R  R  .  T   K  G  .   T  M  N  Q

AAGAGTGCCA ATATTCCCCG ATTATGCCCC CTCCAAGCAG TGAGAGGAGG    450
 E  C  Q  Y  S  P   I  M  P  P   P  S  S   E  R  R
  K  S  A  N  I  P  R   L  C  P  L  Q  A  V   R  G  G
   R  V  P  I  F  P  D  Y  A  P   S  K  Q   .  E  E  E

AGAATTCGGC CCAGCCAGAG TGCCTGTACC TTTTTCTCTC TCAGACTTAA    500
 R  I  R  P  S  Q  S   A  C  T   F  F  S  L  R  L  K
  E  F  G  P  A  R  V  P  V  P   F  S  L   S  D  L  K
   N  S  A  Q  P  E   C  L  Y  L  F  L  S   Q  T  .
```

Fig. 6B

```
          10         20         30         40         50
 1234567890 1234567890 1234567890 1234567890 1234567890
AGCAAATTAA AATAGACCTA GGTAAATTCT CAGATAACCC TGACGGCTAT     550
  A N . N R P R . I L R . P . R L Y
 Q I K I D L G K F S D N P D G Y
S K L K . T . V N S Q I T L T A I

ATTGATGTTT TACAAGGGTT AGGACAATCC TTTGATCTGA CATGGAGAGA     600
  . C F T R V R T I L . S D M E R
 I D V L Q G L G Q S F D L T W R D
L M F Y K G . D N P L I . H G E I

TATAATGTTA CTACTAAATC AGACACTAAC CCCAAATGAG AGAAGTGCCG     650
  Y N V T T K S D T N P K . E K C R
 I M L L L N Q T L T P N E R S A A
. C Y Y . I R H . P Q M R E V P

CTGTAACTGC AGCCCGAGAG TTTGGCGATC TTTGGTATCT CAGTCAGGCC     700
  C N C S P R V W R S L V S Q S G Q
 V T A A R E F G D L W Y L S Q A
L . L Q P E S L A I F G I S V R P

AACAATAGGA TGACAACAGA GGAAGAACA ACTCCCACAG GCCAGCAGGC      750
  Q . D D N R G K N N S H R P A G
 N N R M T T E E R T T P T G Q Q A
T I G . Q Q R K E Q L P Q A S R Q

AGTTCCCAGT GTAGACCCTC ATTGGGACAC AGAATCAGAA CATGGAGATT     800
  S S Q C R P S L G H R I R T W R L
 V P S V D P H W D T E S E H G D W
F P V . T L I G T Q N Q N M E I

GGTGCCACAA ACATTTGCTA ACTTGCGTGC TAGAAGGACT GAGGAAAACT     850
  V P Q T F A N L R A R R T E E N .
 C H K H L L T C V L E G L R K T
G A T N I C . L A C . K D . G K L

AGGAAGAAGC CTATGAATTA CTCAATGATG TCCACTATAA CACAGGGAAA     900
  E E A Y E L L N D V H Y N T G K
 R K K P M N Y S M M S T I T Q G K
G R S L . I T Q . C P L . H R E R

GGAAGAAAAT CTTACTGCTT TTCTGGACAG ACTAAGGGAG GCATTGAGGA     950
  G R K S Y C F S G Q T K G G I E E
 E E N L T A F L D R L R E A L R K
K K I L L L F W T D . G R H . G

AGCATACCTC CCTGTCACCT GACTCTATTG AAGGCCAACT AATCTTAAAG     1000
  A Y L P V T . L Y . R P T N L K G
 H T S L S P D S I E G Q L I L K
S I P P C H L T L L K A N . S . R
```

Fig. 6C

```
              10         20         30         40         50
     1234567890 1234567890 1234567890 1234567890 1234567890
     GATAAGTTTA TCACTCAGTC AGCTGCAGAC ATTAGAAAAA ACTTCAAAAG    1050
      . V Y  H S V   S C R H    . K K    L Q K
      D K F I  T Q S   A A D    I R K N   F K S
      I S L  S L S Q   L Q T    L E K    T S K V

TCTGCCTTAG GCCCGGAGCA GAACTTAGAA ACCCTATTTA ACTTGGCATC    1100
      S A L G   P E Q N L E   T L F N   L A S
      L P . A  R S R T . K    P Y L    T W H P
      C L R  P G A   E L R N   P I .   L G I

CTCAGTTTTT TATAATAGAG ATCAGGAGGA GCAGGCGAAA CGGGACAAAC    1150
      S V F  Y N R D   Q E E    Q A K    R D K R
      Q F F  I I E    I R R S   R R N   G T N
      L S F L   . . R   S G G   A G E T   G Q T

GGGATAAAAA AAAAAGGGGG GGTCCACTAC TTTAGTCATG GCCCTCAGGC    1200
      D K K   K R G   G P L L   . S W   P S G
      G I K K   K G G   V H Y   F S H G   P Q A
      G . K   K K G G   S T T   L V M    A L R Q

AAGCAGACTT TGGAGGCTCT GCAAAAGGGA AAAGCTGGGC AAATCAAATG    1250
      K Q T L   E A L   Q K G   K A G Q   I K C
      S R L   W R L C   K R E   K L G   K S N A
      A D F   G G S   A K G K   S W A   N Q M

CCTAATAGGG CTGGCTTCCA GTGCGGTCTA CAAGGACACT TTAAAAAGA     1300
      L I G   L A S S   A V Y   K D T   L K K I
      . . G   W L P   V R S T   R T L   . K R
      P N R A   G F Q   C G L   Q G H F   K K D

TTATCCAAGT AGAAATAAGC CGCCCCCTTG TCCATGCCCC TTACGTCAAG    1350
      I Q V   E I S   R P L V   H A P   Y V K
      L S K .   K . A   A P L   S M P L   T S R
      Y P S   R N K P   P P C   P C P   L R Q G

GGAATCACTG GAAGGCCCAC TGCCCCAGGG GATGAAGATA CTCTGAGTCA    1400
      G I T G   R P T   A P G   D E D T   L S Q
      E S L   E G P L   P Q G   M K I   L . V R
      N H W   K A H   C P R G   . R Y   S E S

GAAGCCATTA ACCAGATGAT CCAGCAGCAG GACTGAGGGT GCCGGGGCG     1450
      K P L   T R . S   S S R   T E G   A R G E
      S H .   P D D   P A A G   L R V   P G A
      E A I N   Q M I   Q Q Q   D . G C   P G R

AGCGCCAGCC CATGCCATCA CCCTCACAGA GCCCCGGGTA TGTTTGACCA    1500
      R Q P   M P S   P S Q S   P G Y   V . P
      S A S P   C H H   P H R   A P G M   F D H
      A P A   H A I T   L T E   P R V   C L T I
```

Fig. 6D

```
         10         20         30         40         50
1234567890 1234567890 1234567890 1234567890 1234567890
TTGAGAGCCA A                                              1511
L  R   A
.  E   P
E  S   Q
```

Fig. 7A

```
          10         20         30         40         50
  1234567890 1234567890 1234567890 1234567890 1234567890
  ATGGGCAGCA GCCATCATCA TCATCATCAC AGCAGCGGCC TGGTGCCGCG    50
   M  G  S   S  H  H   H  H  H   S  S  G   L  V  P  R

CGGCAGCCAT ATGGCTAGCA TGACTGGTGG ACAGCAAATG GGTCGGATCC   100
   G  S  H   M  A  S   M  T  G  G  Q  Q  M   G  R  I  L

TAGAACGTAT TCTGGAGAAT TGGGACCAAT GTGACACTCA GACGCTAAGA   150
   E  R  I   L  E  N   W  D  Q   C  D  T  Q   T  L  R

AAGAAACGAT TTATATTCTT CTGCAGTACC GCCTGGCCAC AATATCCTCT   200
   K  K  R  F   I  F  F   C  S  T   A  W  P  Q   Y  P  L

TCAAGGGAGA GAAACCTGGC TTCCTGAGGG AAGTATAAAT TATAACATCA   250
   Q  G  R   E  T  W  L   P  E  G   S  I  N   Y  N  I  I

TCTTACAGCT AGACCTCTTC TGTAGAAAGG AGGGCAAATG GAGTGAAGTG   300
   L  Q  L   D  L  F   C  R  K  E   G  K  W   S  E  V

CCATATGTGC AAACTTTCTT TTCATTAAGA GACAACTCAC AATTATGTAA   350
   P  Y  V  Q   T  F  F   S  L  R   D  N  S  Q   L  C  K

AAAGTGTGGT TTATGCCCTA CAGGAAGCCC TCAGAGTCCA CCTCCCTACC   400
   K  C  G   L  C  P  T   G  S  P   Q  S  P   P  P  Y  P

CCAGCGTCCC CTCCCCGACT CCTTCCTCAA CTAATAAGGA CCCCCCTTTA   450
   S  V  P   S  P  T   P  S  S   T  N  K  D   P  P  L

ACCCAAACGG TCCAAAAGGA GATAGACAAA GGGGTAAACA ATGAACCAAA   500
   T  Q  T  V   Q  K  E   I  D  K   G  V  N  N   E  P  K

GAGTGCCAAT ATTCCCCGAT TATGCCCCCT CCAAGCAGTG AGAGGAGGAG   550
   S  A  N   I  P  R  L   C  P  L   Q  A  V   R  G  G  E

AATTGGCCCC AGCCAGAGTG CCTGTACCTT TTTCTCTCTC AGACTTAAAG   600
   F  G  P   A  R  V   P  V  P  F   S  L  S   D  L  K

CAAATTAAAA TAGACCTAGG TAAATTCTCA GATAACCCTG ACGGCTATAT   650
   Q  I  K  I   D  L  G   K  F  S   D  N  P  D   G  Y  I

TGATGTTTTA CAAGGGTTAG GACAATCCTT TGATCTGACA TGGAGAGATA   700
   D  V  L   Q  G  L  G   Q  S  F   D  L  T   W  R  D  I

TAATGTTACT ACTAAATCAG ACACTAACCC CAAATGAGAG AAGTGCCGCT   750
   M  L  L   N  Q  T   L  T  P   N  E  R   S  A  A
```

Fig. 7B

```
            10          20          30          40          50
    1234567890  1234567890  1234567890  1234567890  1234567890
    GTAACTGCAG  CCCGAGAGTT  TGGCGATCTT  TGGTATCTCA  GTCAGGCCAA      800
      V  T  A  A  R  E  F  G  D  L  W  Y  L  S  Q  A  N

CAATAGGATG  ACAACAGAGG  AAAGAACAAC  TCCCACAGGC  CAGCAGGCAG      850
      N  R  M  T  T  E  E  R  T  T  P  T  G  Q  Q  A  V

TTCCCAGTGT  AGACCCTCAT  TGGACACAG  AATCAGAACA  TGGAGATTGG       900
       P  S  V  D  P  H  W  D  T  E  S  E  H  G  D  W

TGCCACAAAC  ATTTGCTAAC  TTGCGTGCTA  GAAGGACTGA  GGAAAACTAG      950
      C  H  K  H  L  L  T  C  V  L  E  G  L  R  K  T  R

GAAGAAGCCT  ATGAATTACT  CAATGATGTC  CACTATAACA  CAGGGAAAGG     1000
      K  K  P  M  N  Y  S  M  M  S  T  I  T  Q  G  K  E

AAGAAAATCT  TACTGCTTTT  CTGGACAGAC  TAAGGGAGGC  ATTGAGGAAG     1050
      E  N  L  T  A  F  L  D  R  L  R  E  A  L  R  K

CATACCTCCC  TGTCACCTGA  CTCTATTGAA  GGCCAACTAA  TCTTAAAGGA     1100
      H  T  S  L  S  P  D  S  I  E  G  Q  L  I  L  K  D

TAAGTTTATC  ACTCAGTCAG  CTGCAGACAT  TAGAAAAAAC  TTCAAAAGTC     1150
      K  F  I  T  Q  S  A  A  D  I  R  K  N  F  K  S  L

TGCCTAAGCT  TGCGGCCGCA  CTCGAGCACC  ACCACCACCA  CCACTGAGAT     1200
      P  K  L  A  A  A  L  E  H  H  H  H  H  H  .  D

CCGGCTGCTA  ACAAAGCCCG  AAAGGAAGCT  GAGTTGGCTN  GTGGCNA        1247
      P  A  A  N  K  A  R  K  E  A  E  L  A  X  G
```

Fig. 8A

```
          10         20         30         40         50
 1234567890 1234567890 1234567890 1234567890 1234567890
ATGGCTAGCA TGACTGGTGG ACAGCAAATG GGTCGGATCC TAGAACGTAT        50
 M  A  S  M  T  G  G  Q  Q  M  G  R  I  L  E  R  I

TCTGGAGAAT TGGACCAAT GTGACACTCA GACGCTAAGA AAGAAACGAT        100
 L  E  N  W  D  Q  C  D  T  Q  T  L  R  K  K  R

TTATATTCTT CTGCAGTACC GCCTGGCCAC AATATCCTCT TCAAGGGAGA       150
 I  F  F  C  S  T  A  W  P  Q  Y  P  L  Q  G  R

GAAACCTGGC TTCCTGAGGG AAGTATAAAT TATAACATCA TCTTACAGCT       200
 E  T  W  L  P  E  G  S  I  N  Y  N  I  I  L  Q  L

AGACCTCTTC TGTAGAAAGG AGGGCAAATG GAGTGAAGTG CCATATGTGC       250
 D  L  F  C  R  K  E  G  K  W  S  E  V  P  Y  V  Q

AAACTTTCTT TTCATTAAGA GACAACTCAC AATTATGTAA AAGTGTGGT       300
 T  F  F  S  L  R  D  N  S  Q  L  C  K  K  C  G

TTATGCCCTA CAGGAAGCCC TCAGAGTCCA CCTCCCTACC CCAGCGTCCC       350
 L  C  P  T  G  S  P  Q  S  P  P  P  Y  P  S  V  P

CTCCCCGACT CCTTCCTCAA CTAATAAGGA CCCCCCTTTA ACCCAAACGG       400
 S  P  T  P  S  S  T  N  K  D  P  P  L  T  Q  T  V

TCCAAAAGGA GATAGACAAA GGGGTAAACA ATGAACCAAA GAGTGCCAAT       450
 Q  K  E  I  D  K  G  V  N  N  E  P  K  S  A  N

ATTCCCCGAT TATGCCCCCT CCAAGCAGTG AGAGGAGGAG AATTCGGCCC       500
 I  P  R  L  C  P  L  Q  A  V  R  G  G  E  F  G  P

AGCCAGAGTG CCTGTACCTT TTCTCTCTC AGACTTAAAG CAAATTAAAA       550
 A  R  V  P  V  P  F  S  L  S  D  L  K  Q  I  K  I

TAGACCTAGG TAAATTCTCA GATAACCCTG ACGGCTATAT TGATGTTTTA       600
 D  L  G  K  F  S  D  N  P  D  G  Y  I  D  V  L

CAAGGGTTAG GACAATCCTT TGATCTGACA TGGAGAGATA TAATGTTACT       650
 Q  G  L  G  Q  S  F  D  L  T  W  R  D  I  M  L  L

ACTAAATCAG ACACTAACCC CAAATGAGAG AAGTGCCGCT GTAACTGCAG       700
 L  N  Q  T  L  T  P  N  E  R  S  A  A  V  T  A  A

CCCGAGAGTT TGGCGATCTT TGGTATCTCA GTCAGGCCAA CAATAGGATG       750
 R  E  F  G  D  L  W  Y  L  S  Q  A  N  N  R  M
```

ACAACAGAGG AAAGAACAAC TCCCACAGGC CAGCAGGCAG TTCCCAGTGT    800
   T  T  E  R  T  T    P  T  G    Q  Q  A    V  P  S  V

AGACCCTCAT TGGACACAG AATCAGAACA TGGAGATTGG TGCCACAAAC     850
   D  P  H  W  D  T  E  S  E  H   G  D  W    C  H  K  H

ATTTGCTAAC TTGCGTGCTA GAAGGACTGA GGAAAACTAG GAAGAAGCCT    900
   L  L  T   C  V  L   E  G  L    R  K  T  R  K  K  P

ATGAATTACT CAATGATGTC CACTATAACA CAGGGAAAGG AAGAAAATCT    950
   M  N  Y  S  M  M  S  T  I  T   Q  G  K  E   E  N  L

TACTGCTTTT CTGGACAGAC TAAGGGAGGC ATTGAGGAAG CATACCTCCC    1000
   T  A  F   L  D  R  L  R  E  A   L  R  K   H  T  S  L

TGTCACCTGA CTCTATTGAA GGCCAACTAA TCTTAAAGGA TAAGTTTATC    1050
   S  P  D   S  I  E   G  Q  L  I   L  K  D   K  F  I

ACTCAGTCAG CTGCAGACAT TAGAAAAAAC TTCAAAAGTC TGCCTAAGCT    1100
   T  Q  S  A  A  D  I  R  K  N   F  K  S  L  P  K  L

TGCGGCCGCA CTCGAGCACC ACCACCACCA CCACTGAGAT CCGGCTGCTA    1150
   A  A  A   L  E  H  H  H  H  H   H  .  D   P  A  A  N

ACAAAGCCCG AAAGGAAGCT GAGTTGGCTG GTGGCA                   1186
   K  A  R   K  E  A   E  L  A  G   G
```

Fig. 9A

```
            10         20         30         40         50
     1234567890 1234567890 1234567890 1234567890 1234567890
     TGTCCGCTGT GCTCCTGATC CAGCACAGGC GCCCATTGCC TCTCCCAATT    50
     C P L C    S . S      S T G      A H C L    S Q L
      V R C      A P D P    A Q A      P I A      S P N W
       S A V      L L I      Q H R      R P L      P L P I

GGGCTAAAGG CTTGCCATTG TTCCTGCACA GCTAAGTGCC TGGGTTCATC   100
     G . R      L A I V    P A Q      L S A      W V H P
      A K G      L P L      F L H S    . V P      G F I
       G L K A    C H C      S C T      A K C L    G S S

CTAATCGAGC TGAACACTAG TCACTGGGTT CCACGGTTCT CTTCCATGAC   150
     N R A      E H .      S L G S    T V L      F H D
      L I E L    N T S      H W V      P R F S    S M T
       . S S      . T L V    T G F      H G S      L P . P

CCATGGCTTC TAATAGAGCT ATAACACTCA CTGCATGGTC CAAGATTCCA   200
     P W L L    I E L      . H S      L H G P    R F H
      H G F      . . S Y    N T H      C M V      Q D S I
       M A S      N R A      I T L T    A W S      K I P

TTCCTTGGAA TCCGTGAGAC CAAGAACCCC AGGTCAGAGA ACACAAGGCT   250
     S L E      S V R P    R T P      G Q R      T Q G L
      P W N      P . D      Q E P Q    V R E      H K A
       F L G I    R E T      K N P      R S E N    T R L

TGCCACCATG TTGGAAGCAG CCCACCACCA TTTTGGAAGC AGCCCGCCAC   300
     P P C      W K Q      P T T I    L E A      A R H
      C H H V    G S S      P P P      F W K Q    P A T
       A T M      L E A A    H H H      F G S      S P P L

TATCTTGGGA GCTCTGGGAG CAAGGACCCC AGGTAACAAT TTGGTGACCA   350
     Y L G S    S G S      K D P R    . Q F      G D H
      I L G      A L G A    R T P      G N N      L V T T
       S W E      L W E      Q G P Q    V T I      W . P

CGAAGGGACC TGAATCCGCA ACCATGAAGG GATCTCCAAA GCAATTGGAA   400
     E G T      . I R N    H E G      I S K      A I G N
      R G P      E S A      T M K G    S P K      Q L E
       R R D L    N P Q      P . R      D L Q S    N W K
```

ATGTTCCTCC CAAGGCAAAA ATGCCCCTAA GATGTATTCT GGAGAATTGG       450
  V  P  P   K  A  K   M  P  L     R  C  I  L    E  N  W
M  F  L  P   R  Q  K   C  P  .    D  V  F  W   R  I  G
 C  S  S   Q  G  K  N   A  P  K   M  Y  S    G  E  L  G

GACCAATTTG ACCCTCAGAC AGTAAGAAAA AAATGACTTA TATTCTTCTG       500
  D  Q  F   D  P  Q  T   V  R  K    .  L  I   F  F  C
T  N  L   T  L  R  Q    .  E  K   N  D  L    Y  S  S  A
  P  I   .  P  S  D    S  K  K  K   M  T  Y    I  L  L

CAGTACCGCC CTGGCCACGA TATCCTCTTC AAGGGGGAGA AACCTGGCCT       550
  S  T  A   L  A  T  I   S  S  S    R  G  R   N  L  A  S
V  P  P   W  P  R   Y  P  L  Q    G  G  E   T  W  P
 Q  Y  R  P   G  H  D   I  L  F   K  G  E  K   P  G  L

CCTGAGGGAA GTATAAATTA TAACACCATC TTACAGCTAG ACCTGTTTTG       600
  .  G  K   Y  K  L   .  H  H  L    T  A  R   P  V  L
P  E  G  S   I  N  Y   N  T  I   L  Q  L  D   L  F  C
 L  R  E   V  .  I  I   T  P  S   Y  S  .    T  C  F  V

TAGAAAAGGA GGCAAATGGA GTGAAGTGCC ATATTTACAA ACTTTCTTTT       650
  .  K  R  R   Q  M  E    .  S  A   I  F  T   N  F  L  F
R  K  G   G  K  W  S   E  V  P   Y  L  Q    T  F  F  S
 E  K  E   A  N  G   V  K  C  H   I  Y  K   L  S  F

CATTAAAAGA CAACTCGCAA TTATGTTAAC AGTGTGATTT GTGTTCCTAC       700
  I  K  R   Q  L  A  I   M  L  T    V  .  F   V  F  L  H
L  K  D   N  S  Q   L  C  .  Q    C  D  L   C  S  Y
 H  .  K  T   T  R  N   Y  V  N   S  V  I  C   V  P  T

ACGGAAGCCC TCAGATTCTA CTCCCCACCC CCGGCATCTC CCCTGAATCC       750
  G  S  P   Q  I  L   L  P  T  P    G  I  S   P  E  S
T  E  A  L   R  F  Y   S  P  P   P  A  S  P   L  N  P
 R  K  P   S  D  S  T   P  H  P   R  H  L    P  .  I  P

CTCCCCAACT TATT                                              764
  L  P  N  L
S  P  T   Y
 P  Q  L   I
```

Fig. 10A

```
          10         20         30         40         50
 1234567890 1234567890 1234567890 1234567890 1234567890
TGTCCGCTGT GCTCCTGATC CAGCACAGGC GCCCATTGCC TCTCCCAATT    50
 C  P  L  C  S  .  S   S  T  G   A  H  C  L  S  Q  L
  V  R  C   A  P  D  P  A  Q  A   P  I  A   S  P  N  W
   S  A  V   L  L  I   Q  H  R  R   P  L  P   L  P  I

GGGCTAAAGG CTTGCCATTG TTCCTGCACA GCTAAGTGCC TGGGTTCATC   100
 G  .  R  L  A  I  V   P  A  Q   L  S  A   W  V  H  P
  A  K  G   L  P  L   F  L  H  S   .  V  P   G  F  I
   G  L  K   A  C  H   C  S  C  T   A  K  C   L  G  S  S

CTAATCGAGC TGAACACTAG TCACTGGGTT CCACGGTTCT CTTCCATGAC   150
 N  R  A  E  H  .  S   L  G  S   T  V  L   F  H  D
  L  I  E  L  N  T  S   H  W  V   P  R  F  S   S  M  T
   .  S  S   .  T  L  V   T  G  F   H  G  S   L  P  .  P

CCATGGCTTC TAATAGAGCT ATAACACTCA CTGCATGGTC CAAGATTCCA   200
 P  W  L  L  I  E  L   .  H  S   L  H  G  P   R  F  H
  H  G  F   .  .  S  Y   N  T  H   C  M  V   Q  D  S  I
   M  A  S   N  R  A   I  T  L  T   A  W  S   K  I  P

TTCCTTGGAA TCCGTGAGAC CAAGAACCCC AGGTCAGAGA ACACAAGGCT   250
 S  L  E   S  V  R  P   R  T  P   G  Q  R   T  Q  G  L
  P  W  N   P  .  D   Q  E  P  Q   V  R  E   H  K  A
   F  L  G  I   R  E  T   K  N  P   R  S  E  N   T  R  L

TGCCACCATG TTGGAAGCAG CCCACCACCA TTTTGGAAGC GGCCCGCCAC   300
 P  P  C  W  K  Q   P  T  T  I   L  E  A  A   R  H
  C  H  H  V   G  S  S   P  P  P   F  W  K  R   P  A  T
   A  T  M   L  E  A  A   H  H  H   F  G  S   G  P  P  L

TATCTTGGGA GCTCTGGGAG CAAGGACCCC CAGGTAACAA TTTGGTGACC   350
 Y  L  G  S   S  G  S   K  D  P   Q  V  T   I  W  .  P
  I  L  G   A  L  G  A   R  T  P   R  .  Q   F  G  D  H
   S  W  E   L  W  E   Q  G  P  P   G  N  N   L  V  T

ACGAAGGGAC CTGAATCCGC AACCATGAAG GGATCTCCAA AGCAATTGGA   400
 R  R  D   L  N  P  Q   P  .  R   D  L  Q   S  N  W  K
  E  G  T   .  I  R   N  H  E  G   I  S  K   A  I  G
   T  K  G  P   E  S  A   T  M  K   G  S  P  K   Q  L  E
```

Fig. 10B

```
         10         20         30         40         50
1234567890 1234567890 1234567890 1234567890 1234567890
AATGTTCCTC CCAAGGCAAA AATGCCCCTA AGATGTATTC TGGAGAATTG      450
  C  S  S    Q  G  K    N  A  P    K  M  Y  S    G  E  L
 N  V  P  P    K  A  K    M  P  L    R  C  I  L    E  N  W
M  F  L      P  R  Q  K    C  P  .    D  V  F      W  R  I  G

GGACCAATCT GACCCTCAGA CAGTAAGAAA AAAAATGACT TATATTCTTC      500
  G  P  I  .    P  S  D    S  K  K    K  N  D  L    Y  S  S
 D  Q  S    D  P  Q  T    V  R  K    K  M  T      Y  I  L  L
T  N  L      T  L  R    Q  .  E  K    K  .  L      I  F  F

TGCAGTACCG CCTGGCCACG GATATCCTCT TCAAGGGGGA GAAACCTGGC      550
  A  V  P    P  G  H  G    Y  P  L    Q  G  G      E  T  W  P
 Q  Y  R    L  A  T      D  I  L  F    K  G  E      K  P  G
C  S  T  A    W  P  R      I  S  S    S  R  G      N  L  A

CTCCTGAGGG AAGTATAAAT TATAACACCA TCTTACAGCT AGACCTGTTT      600
  P  E  G    S  I  N      Y  N  T  I    L  Q  L    D  L  F
 L  L  R  E  V  .  I      I  T  P      S  Y  S  .    T  C  F
S  .  G      K  Y  K  L    .  H  H      L  T  A      R  P  V  L

TGTAGAAAAG GAGGCAAATG GAGTGAAGTG CCATATTTAC AAACTTTCTT      650
  C  R  K  G    G  K  W      S  E  V    P  Y  L  Q    T  F  F
 V  E  K      E  A  N  G    V  K  C    H  I  Y      K  L  S  F
.  K  R      R  Q  M      E  .  S  A    I  F  T      N  F  L

TTCATTAAAA GACAACTCGC AATTATGTAA ACAGTGTGAT TTGTGTCCTA      700
  S  L  K      D  N  S  Q    L  C  K    Q  C  D      L  C  P  T
 H  .  K      T  T  R      N  Y  V  N    S  V  I      C  V  L
F  I  K  R    Q  L  A      I  M  .      T  V  .      F  V  S  Y

CAGGAAGCCC TCAGATCTAC CTCCCTACCC CGGCATCTCC CTGACTCCTT      750
  G  S  P    Q  I  Y      L  P  T  P    A  S  P    .  L  L
 Q  E  A  L    R  S  T      S  L  P    R  H  L      P  D  S  F
R  K  P      S  D  L  P    P  Y  P      G  I  S      L  T  P  S

CCCCAACTAA TAAGGACCCA CTTCAGCCCA AACAGTCCAA AAGGACATAG      800
  P  Q  L  I    R  T  H      F  S  P    N  S  P  K    G  H
 P  N  .      .  G  P  T    S  A  Q    T  V  Q      K  D  I
  P  T  N    K  D  P      L  Q  P  K    Q  S  K      R  T  .
```

Fig. 11A

```
         10         20         30         40         50
1234567890 1234567890 1234567890 1234567890 1234567890
GGCATTGATA GCACCCATCA GATGGCCAAA TCATTATTTA CTGGACCAGG        50
 G  I  D   S  T  H  Q  M  A  K   S  L  F  T  G  P  G
A  L  I   A  P  I  R  W  P  N   H  Y  L   L  D  Q  A
 H  .  .   H  P  S   D  G  Q   I  I  Y   W  T  R

CCTTTTCAAA ACTATCAAGC AGATAGGGCC CGTGAAGCAT GCCAAAGAAA       100
 L  F  K   T  I  K  Q  I  G  P   V  K  H   A  K  E  I
F  S  K   L  S  S  R   .  G  P   .  S  M   P  K  K
 P  F  Q  N  Y  Q  A   D  R  A   R  E  A  C  Q  R  N

TAATCCCCTG CCTTATCGCC ATGTTCCTTC AGGAGAACAA AGAACAGGCC       150
  .  P  C   L  I  A   M  F  L  Q  E  N  K  E  Q  A
 .  S  P  A  L  S  P  C  S  F   R  R  T  K  N  R  P
N  P  L   P  Y  R  H  V  P  S   G  E  Q   R  T  G  H

ATTACCCAGG GGAAGACTGG CAACTAGATT TTACCCACAT GGCCAAATGT       200
 I  T  Q  G  K  T  G   N  .  I   L  P  T  W  P  N  V
L  P  R   G  R  L  A   T  R  F   Y  P  H   G  Q  M  S
 Y  P  G   E  D  W  Q  L  D  F   T  H  M   A  K  C

CAGGGATTTC AGCATCTACT AGTCTGGGCA GATACTTTCA CTGGTTGGGT       250
 R  D  F   S  I  Y  .  S  G  Q   I  L  S   L  V  G  W
 G  I  S   A  S  T   S  L  G  R   Y  F  H  W  L  G
Q  G  F  Q  H  L  L   V  W  A   D  T  F  T  G  W  V

GGAGTCTTCT CCTTGTAGGA CAGAAAAGAC CCAAGAGGTA ATAAAGGCAC       300
 S  L  L   L  V  G   Q  K  R  P   K  R  .  .  R  H
G  V  F  S  L  .  D  R  K  D   P  R  G  N  K  G  T
 E  S  S   P  C  R  T  E  K  T   Q  E  V   I  K  A  L

TAATGAAATA ATTCCCAGAT TGGACTTCC CCCAGGATTA CAGGGTGACA        350
 .  .  N  N  S  Q  I   W  T  S   P  R  I  T  G  .  Q
N  E  I   I  P  R  F   G  L  P   P  G  L   Q  G  D  N
 M  K  .   F  P  D   L  D  F  P   Q  D  Y   R  V  T
```

Fig. 11B

```
          10         20         30         40         50
  1234567890 1234567890 1234567890 1234567890 1234567890
  ATGGCCCCGC TTTCAAGGCT GCAGTAACCC AGGGAGTATC CCAGGTGTTA    400
   W  P  R   F  Q  G    C  S  N  P   G  S  I   P  G  V  R
    G  P  A   F  K  A   A  V  T  Q   G  V  S   Q  V  L
  M  A  P  L   S  R  L   Q  .  P   R  E  Y  P   R  C  .

GGCATACAAT ATCACTTACA CTGTGCCTGG AGGCCACAAT CCTCCAGAAA    450
     H  T  I   S  L  T   L  C  L  E   A  T  I   L  Q  K
    G  I  Q  Y   H  L  H   C  A  W   R  P  Q  S   S  R  K
   A  Y  N   I  T  Y  T   V  P  G   H  N   P  P  E  K

AGTCAAGAAA ATGAATGAAA CACTCAAAGA TCTAAAAAAG CTAACCCAAG    500
   S  Q  E   N  .  N   T  Q  R   S  K  K   A  N  P  R
    V  K  K   M  N  E   T  L  K  D   L  K  K   L  T  Q  E
     S  R  K   .  M  K   H  S  K  I   .  K  S   .  P  K

AAACCCACAT TGCATGACCT GTTCTGTTGC CTATAACCTT ACTAAGAATC    550
   N  P  H   C  M  T  C   S  V  A   Y  N  L   T  K  N  P
    T  H  I   A  .  P   V  L  L  P   I  T  L   L  R  I
   K  P  T  L   H  D  L   F  C  C   L  .  P  Y   .  E  S

CATAACTATC CCCCAAAAAG CAGGACTTAG CCCATACGAG ATGCTATATG    600
   .  L  S   P  K  K   Q  D  L  A   H  T  R   C  Y  M
    H  N  Y  P   P  K  S   R  T  .   P  I  R  D   A  I  W
     I  T  I   P  Q  K  A   G  L  S   P  Y  E   M  L  Y  G

GATGGCCTTT CCTAACCAAT GACCTTGTGC TTGACTGAGA AATGGCCAAC    650
   D  G  L   S  .  P  M   T  L  C   L  T  E  K   W  P  T
    M  A  F   P  N  Q  .   P  C  A   .  L  R   N  G  Q  L
     W  P  F   L  T  N   D  L  V  L   D  .  E   M  A  N

TTAGTTGCAG ACATCACCTC CTTAGCCAAA TATCAACAAG TTCTTAAAAC    700
   .  L  Q   T  S  P  P   .  P  N   I  N  K   F  L  K  H
    S  C  R   H  H  L   L  S  Q  I   S  T  S  S   .  N
   L  V  A  D   I  T  S   L  A  K   Y  Q  Q  V   L  K  T
```

Fig. 11C

```
          10         20         30         40         50
 1234567890 1234567890 1234567890 1234567890 1234567890
 ATCACAGGGA ACCTGTCCCC GAGAGGAGGG AAAGGAACTA TTCCACCCTG    750
   H  R  E    P  V  P    E  R  R    E  R  N    Y  S  T  L
  I  T  G  N   L  S  P   R  G  G    K  G  T  I   P  P  W
   S  Q  G    T  C  P  R   E  E  G    K  E  L    F  H  P  G

GTGACATG                                                  758
  V  T
   .  H
    D  M
```

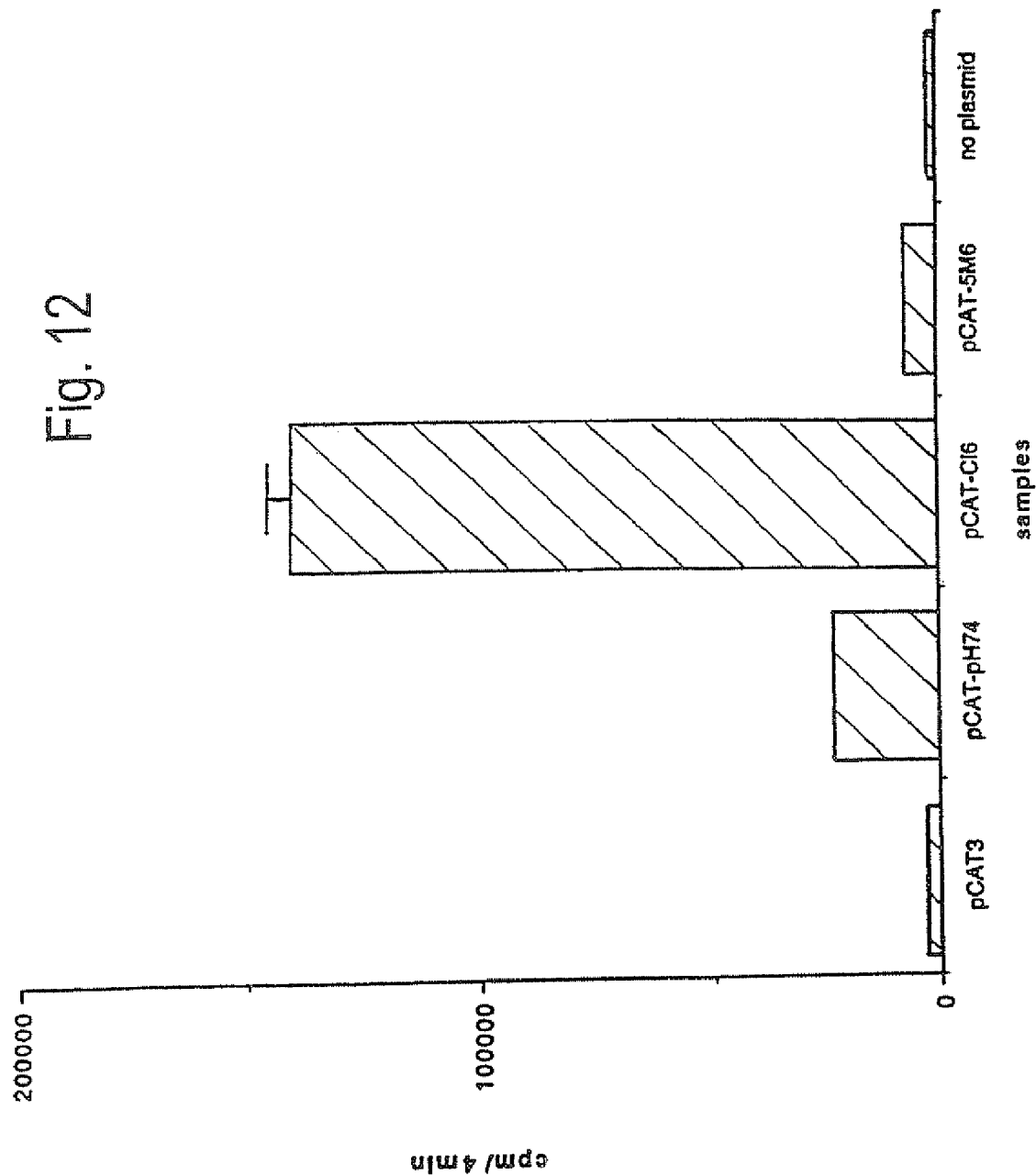

```
GGACCCGTAG TATGGGGTAA TCCCCTCCGG GAAACCAAGC CCAGTACTC AGAAGAAGAA ATAGAATGGG GAACCTCACG AGGACATGGT TTCCTCCCT    100
 G  P  V  V  W  G  N  P  L  R  E  T  K  P  Q  Y  S  E  E  E  I  E  W  G  T  S  R  G  H  G  F  L  P  S         34

CAGGATGGCT AGCCACTGAA GAAGAAAAA TACTTTGCT GGCAGCTAAC CCTTCAGCAA CAATGAAAT TACTTAAAAC CCTTCAGCAA ACCTTCCACT TAGGCATTGA    200
 G  W  L  A  T  E  E  G  K  I  L  L  L  A  A  N  Q  W  K  L  K  T  L  Q  Q  T  F  M  L  G  I  D                 67

TAGGCACCAT CAGATAGCCA AATCATTATT TACTGGACCA GGCCTTTCA AAACTATCAA GCAGATAGTC AGGGCCGTG AAGTGCCA AAGAAATAT    300
 S  T  M  Q  I  A  K  S  L  F  T  G  P  G  L  F  K  T  I  K  Q  I  V  R  A  C  E  V  C  Q  R  N  N            100

CCCCTGCCTT ATGCCAAGC TCCTTCAGGA GAACAAGAA CAGGCAATTA CCCAAGAAGA GACTGGCAAC TAGATTTTAT CCACATGCCA AAATCACAGG    400
 P  L  P  Y  R  Q  A  P  S  G  E  Q  R  T  G  N  Y  P  R  E  D  W  Q  L  D  P  I  H  M  P  K  S  Q  G        134

GATTTCAGTG TCTACTAGTC TGGGTAGATA CTTTCACTGG CTGAGGCTA CAGAGTGACA AAGTTCCAA GCCTTCCCT GTAGGACAGA AGGGAGTATC AGGCACTAGT    500
 F  Q  C  L  L  V  W  V  D  T  F  T  G  W  A  E  A  P  P  C  R  T  E  K  F  Q  E  V  I  K  A  L  V           167

TCATGAAGTA ATTCCCAGAT TCGGACTTCC CTGAGGCTA CAGAGTGACA CCTCAGGGAA GTTGAGAGAA ATGAATACAC TCTAAACAGA CTACCCAGG    600
 H  E  V  I  P  R  F  G  L  P  .  G  L  Q  S  D  N  G  P  A  F  K  A  T  V  T  Q  G  V  S  Q  A  L           200

GGTATAGAAT ATCACTTACA CTGCACCTAG AGGCCACAAT CCTCAGGGAA GTTGAGAGAA ATGAATACAC TCTAAACAGA CTACCCAGG    700
 G  I  E  Y  H  L  H  C  T  .  R  P  Q  S  G  K  V  E  K  M  K  T  L  K  R  H  L  N  K  L  T  Q  R         234

AAACCCACCT CTAACCAATG ACCTTCGTCT GTCTGTGT CTATAGAATC CAAACTCTC CCCAAAGGC AGACTTAGC CCATACAGAA TGCTGTATGG    800
 T  H  L  A  W  S  A  L  S  I  A  L  L  R  I  Q  N  S  P  Q  K  A  G  L  S  P  Y  R  M  L  Y  G             267

ACGGTCCTTC CTAACCAGTG ACCTTCGTCT TGAACAAGAG ATGGCCAACT TAGTGCAGA CATCACCTCC TTAGCAAAT ATCACCAAGT TCTTAAACA    900
 R  S  F  L  T  W  D  L  L  L  D  Q  E  M  A  N  L  V  A  D  I  T  S  L  A  K  Y  Q  Q  V  L  K  T          300

TTACAAGGAG CCCTGCCCGT AGAGGAGGGA AAGAAATAT TCCAGTCGGT TGTCATGTA AAGTGGCTG GAGTGGAGTC TGGATCAT CACACTGAA TCCCTAGCA    1000
 L  Q  G  A  C  P  R  E  E  G  K  E  I  F  K  P  G  V  K  V  L  V  K  S  L  P  S  M  S  P  S  L  D  T       334

CATCTGGGG AGGACCCTAC CCAGTCATTT TATCTATCCC AACTGCGGTT AAGTGGAGTG GAGTGGAGTC TGGATCAT CACACTCGAA TCTAACCCTG    1100
 S  N  G  G  P  Y  P  V  I  L  S  I  P  T  A  V  K  V  A  G  V  E  S  M  H  T  R  I  K  P  W                367

GATACTGCCG AAGGAACCCG AAAATCCAGG GGACAACCCT AGCTATTTCT TTGAACCTCT AGAAGACCTG TCCCTGCTCT TCAAGCAACA ACCTGA         1197
 I  L  P  K  E  F  E  N  P  G  D  N  A  S  Y  F  F  E  D  L  C  L  L  F  K  Q  Q  P  .                     398
```

Fig. 16

ISOLATED MULTIPLE SCLEROSIS (MS)-ASSOCIATED RETROVIRUS (MSRV) NUCLEIC ACIDS CORRESPONDING TO THE GAG REGION

CROSS-REFERENCE TO PRIOR APPLICATIONS

This is a divisional of application Ser. No. 09/319,156 filed Nov. 2, 1999, which issued as U.S. Pat. No. 7,771,927 on Aug. 10, 2010, which is a National Stage Application of PCT/FR98/01460 filed Jul. 7, 1998, and claims the benefit of French Application No 9708816 filed Jul. 7, 1997. The entire disclosure of the prior applications are hereby incorporated by reference in its entirety.

BACKGROUND OF THE INVENTION

Multiple sclerosis (MS) is a demyelinizing disease of the central nervous system (CNS) of which the complete cause still remains unknown.

Numerous studies have supported the hypothesis for a viral etiology of the disease, but none of the known viruses tested has proved to be the causative agent tested for: a review of the viruses tested in MS for many years has been carried out by E. Norrby and R. T. Johnson.

Recently, a retrovirus, different from the known human retroviruses, was isolated from patients suffering from MS. The authors were able to show that this retrovirus could be transmitted in vitro, that patients suffering from MS produced antibodies capable of recognizing proteins associated with the infection of the leptomeningeal cells by this retrovirus, and that the expression of the latter could be greatly stimulated by the immediate-early genes of some herpesviruses.

All these results argue in favor of the role in MS of at least one unknown retrovirus or of a virus having a reverse transcriptase (RT) activity which is detectable by the method published by H. Perron and termed "LM7-type RT" activity.

The studies by the applicant have made it possible to obtain two continuous cell lines infected with natural isolates obtained from two different patients suffering from MS, by a culture method as described in the document WO-A-93 20188, whose content is incorporated by reference into the present description. These two lines derived from cells of human choroid plexus, called LM7PC and PLI-2, were deposited at the E.C.A.C.C. on 22 Jul. 1992 and 8 Jan. 1993, respectively, under numbers 92 072201 and 93 010817, in accordance with the provisions of the Treaty of Budapest. Moreover, the viral isolates possessing an LM7-type RT activity have also been deposited at the E.C.A.C.C. under the overall name of "strains". The "strain" or isolate harbored by the PLI-2 line, called POL-2, was deposited at the E.C.A.C.C. on 22 Jul. 1992 under No. V92072202. The "strain" or isolate harbored by the LM7PC line, called MS7PG, was deposited at the E.C.A.C.C. on 8 Jan. 1993 under No. V93010816.

Using the above-mentioned cultures and isolates, characterized by biological and morphological criteria, efforts were then made to characterize the genetic material associated with the viral particles produced in these cultures.

The proportions of genome already characterized were used to develop molecular detection tests for the viral genome and immunoserological tests, using the amino acid sequences encoded by the nucleotide sequences of the viral genome, in order to detect the immune response directed against epitopes associated with the viral infection and/or expression.

These tools have already made it possible to confirm an association between MS and the expression of the sequences identified in the patents cited further on. However, the viral system discovered by the applicant is related to a complex retroviral system. Indeed, the sequences which are found to be encapsidated in the extracellular viral particles produced by the different cultures of cells of patients suffering from MS show clearly that there is co-encapsidation of retroviral genomes which are related but different from the "wild-type" retroviral genome which produces the infectious viral particles. This phenomenon was observed between replicative retroviruses and endogenous retroviruses belonging to the same family, or even heterologous retroviruses. The concept of endogenous retrovirus is very important in the context of our discovery because, in the case of MSRV-1, it has been observed that endogenous retroviral sequences comprising sequences homologous to the MSRV-1 genome exist in normal human DNA. The existence of endogenous retroviral elements (ERV) related to MSRV-1 through all or part of their genome explains the fact that the expression of the MSRV-1 retrovirus in human cells can interact with related endogenous sequences. These interactions are found in the case of pathogenic and/or infectious endogenous retroviruses (for example some ecotropic strains of the Murine Leukemia virus), in the case of exogenous retroviruses whose nucleotide sequence may be found partially or completely in the form of ERVs, in the genome of the host animal (e.g. mouse mammary tumor exogenous virus transmitted via milk). These interactions consist mainly of (i) a transactivation or co-activation of ERVs by the replicative retrovirus, (ii) an "illegitimate" encapsidation of related RNAs of ERVs, or of ERVs—or even of cellular RNAs—simply possessing compatible encapsidation sequences, into the retroviral particles produced by the expression of the replicative strain, which are sometimes transmissible and sometimes with an inherent pathogenicity, and (iii) relatively high recombinations between the co-encapsidated genomes, in particular in the reverse transcription phases, which lead to the formation of hybrid genomes, which are sometimes transmissible and sometimes with an inherent pathogenicity.

Thus, (i) various MSRV-1-related sequences have been found in purified viral particles; (ii) molecular analysis of the various regions of the MSRV-1 retroviral genome should be carried out by systematically analyzing the co-encapsidated, interfering and/or recombinant sequences which are generated by the infection and/or expression of MSRV-1; furthermore, some clones may have portions of defective sequences produced by the retroviral replication and the template and/or transcription errors caused by reverse transcriptase; (iii) the families of sequences related to the same retroviral genomic region are the supports for an overall diagnostic detection which may be optimized by the identification of invariable regions among the clones expressed and by the identification of reading frames responsible for the production of antigenic and/or pathogenic polypeptides which may only be produced by a portion, or even only one, of the clones expressed and under these conditions, the systematic analysis of the clones expressed in one region of a given gene makes it possible to evaluate the frequency of variation and/or recombination of the MSRV-1 genome in this region and to define the optimum sequences for the applications, in particular the diagnostic applications; (iv) the pathology caused by a retrovirus such as MRSV-1 may be a direct effect of its expression and of the proteins or peptides produced as a result, but also an effect of the activation, encapsidation, recombination of related or heterologous genomes and proteins or peptides produced as a result; thus, these genomes associated with the expression and/or infection by MSRV-1 are an integral part of the potential pathogenicity of this virus and therefore constitute diagnostic detection supports and particular therapeutic targets.

Likewise, any agent which is associated with, or which is a cofactor for these interactions responsible for the pathogenicity in question, such as MSRV-2 or the gliotoxic factor described in the patent application published under the No. FR-2,716,198, can participate in the development of an overall and very effective strategy for therapeutic diagnosis, prognosis, monitoring and/or integrated therapy for MS in particular, but also for any other disease associated with the same agents.

In this context, a parallel discovery has been made in another autoimmune disease, rheumatoid arthritis (RA), which has been described in the French patent application published under the No. FR-2,731,356. This discovery shows that, by applying methodological approaches similar to those which were used in the studies by the applicant on MS, it has been possible to identify a retrovirus expressed in RA which shares the sequences described for MSRV-1 in MS and also the coexistence of an MSRV-2-associated sequence which is also described in MS. As regards MSRV-1, the sequences commonly detected in MS and RA relate to the pol and gag genes. On the basis of current knowledge, it is possible to combine the gag and pol sequences described with the MSRV-1 strains expressed in these two diseases.

The present patent application has as its object various results, supplementary in relation to those already protected by the French patent applications:

No. 92/04322 of 3 Apr. 1992, published under No. 2,689,519;

No. 92/13447 of 3 Nov. 1992, published under No. 2,689,521;

No. 92/13443 of 3 Nov. 1992, published under No. 2,689,520;

No. 94/01529 of 4 Feb. 1994, published under No. 2,715,936;

No. 94/01531 of 4 Feb. 1994, published under No. 2,715,939;

No. 94/01530 of 4 Feb. 1994, published under No. 2,715,938;

No. 94/01532 of 4 Feb. 1994, published under No. 2,715,937;

No. 94/14322 of 24 Nov. 1994, published under No. 2,727,428;

No. 94/15810 of 23 Dec. 1994, published under No. 2,728,585; and

Patent Application WO 97/06260.

SUMMARY OF THE INVENTION

The present invention relates, first of all, to a nucleic material, which may consist of a retroviral material, in isolated or purified state, which may be understood or characterized in various ways:

it comprises a nucleotide sequence chosen from the group which consists of (i) the sequences SEQ ID NO: 4, SEQ ID NO: 6, SEQ ID NO: 9, SEQ ID NO: 12, SEQ ID NO: 16, SEQ ID NO: 21, SEQ ID NO: 30 and SEQ ID NO: 31; (ii) the sequences complementary to sequences (i); and (iii) the sequences equivalent to sequences (i) or (ii), in particular the sequences having, for every series of 100 contiguous monomers, at least 50%, and preferentially at least 70% homology with sequences (i) or (ii) respectively;

it encodes a polypeptide having, for every contiguous series of at least 30 amino acids, at least 50%, and preferably at least 70% homology with a peptide sequence chosen from the group which consists of SEQ ID NO: 5, SEQ ID NO: 7, SEQ ID NO: 10, SEQ ID NO: 13, SEQ ID NO: 25 and SEQ ID NO: 26;

its pol gene comprises a nucleotide sequence identical or equivalent to a sequence chosen from the group which consists of SEQ ID NO: 4, SEQ ID NO: 16 and their complementary sequences;

the 5' end of its pol gene starts at nucleotide 1419 of SEQ ID NO: 21;

its pol gene encodes a polypeptide having, for every contiguous series of at least 30 amino acids, at least 50%, and preferably at least 70% homology with the peptide sequence SEQ ID NO: 5;

the 3' end of its gag gene ends at nucleotide 1418 of SEQ ID NO: 21;

its env gene comprises a nucleotide sequence identical or equivalent to a sequence chosen from the group which consists of SEQ ID NO: 9, and its complementary sequences;

its env gene comprises a nucleotide sequence which starts at nucleotide 1 of SEQ ID NO: 9 and ends at nucleotide 233 of SEQ ID NO: 6;

its env gene encodes a polypeptide having, for every contiguous series of at least 30 amino acids, at least 50%, and preferably at least 70% homology with the sequence SEQ ID NO: 10;

the U3R region of its 3' LTR comprises a nucleotide sequence which ends at nucleotide 617 of SEQ ID NO: 6;

the RU5 region of its 5' LTR comprises a nucleotide sequence which starts at nucleotide 755 of SEQ ID NO: 12 and ends at nucleotide 337 of SEQ ID NO: 30 or SEQ ID NO: 31;

a retroviral nucleic material comprising a sequence which starts at nucleotide 755 of SEQ ID NO: 12 and which ends at nucleotide 617 of SEQ ID NO: 6;

the retroviral nucleic material as defined above is in particular associated with at least one autoimmune disease such as multiple sclerosis or rheumatoid arthritis.

The invention also relates to a nucleotide fragment which corresponds to at least one of the following definitions:

it comprises or consists of a nucleotide sequence chosen from the group which consists of (i) the sequences SEQ ID NO: 4, SEQ ID NO: 6, SEQ ID NO: 9, SEQ ID NO: 12, SEQ ID NO: 16, SEQ ID NO: 21, SEQ ID NO: 30 and SEQ ID NO: 31; (ii) the sequences complementary to sequences (i); and (iii) the sequences equivalent to sequences (i) or (ii), in particular the sequences having, for every series of 100 contiguous monomers, at least 50%, and preferentially at least 70% homology with sequences (i) or (ii) respectively;

it comprises or consists of a nucleotide sequence encoding a polypeptide having, for every contiguous series of at least 30 amino acids, at least 50%, and preferably at least 70% homology with a peptide sequence chosen from the group which consists of SEQ ID NO: 5, SEQ ID NO: 7, SEQ ID NO: 10, SEQ ID NO: 13, SEQ ID NO: 25 and SEQ ID NO: 26.

Other subjects of the present invention are the following:

a nucleic probe for the detection of a retrovirus associated with multiple sclerosis and/or rheumatoid arthritis, capable of hybridizing specifically with any fragment defined above and belonging to the genome of said retrovirus; it advantageously possesses from 10 to 100 nucleotides, preferably from 10 to 30 nucleotides;

a primer for the amplification, by polymerization, of an RNA or of a DNA of a retrovirus associated with multiple sclerosis and/or rheumatoid arthritis, which comprises a nucleotide sequence identical or equivalent to at least a portion of the nucleotide sequence of a fragment defined above, in particular a nucleotide sequence having, for every series of 10 contiguous monomers, at least 50%, preferably at least 70% homology with at least said portion of said fragment; preferably the nucleotide sequence of a primer of the invention is chosen from SEQ ID NO: 8, SEQ ID NO: 11, SEQ ID NO: 14, SEQ ID NO: 15, SEQ ID NO: 17, SEQ ID NO: 18, SEQ ID NO: 19, SEQ ID NO: 20, SEQ ID NO: 23, and SEQ ID NO: 24;

an RNA or a DNA and in particular a replication and/or expression vector, comprising a genomic fragment of the nucleic material or a fragment defined above;

a peptide encoded by any open reading frame belonging to a nucleotide fragment defined above, in particular a polypeptide, for example oligopeptide forming or comprising an antigenic determinant recognized by sera of patients infected with the MSRV-1 virus, and/or in whom the MSRV-1 virus has been reactivated; a preferential peptide comprises a sequence identical, partially or completely, or equivalent to a sequence chosen from SEQ ID NO: 5, SEQ ID NO: 7, SEQ ID NO: 10, SEQ ID NO: 13, SEQ ID NO: 25 and SEQ ID NO: 26;

a diagnostic, prophylactic or therapeutic composition, in particular for inhibiting the expression of at least one retrovirus associated with multiple sclerosis and/or rheumatoid arthritis, comprising a nucleotide fragment defined above;

a method for detecting a retrovirus associated with multiple sclerosis and/or rheumatoid arthritis, in a biological sample, comprising the steps consisting of bringing an RNA and/or a DNA assumed to belong to or obtained from said retrovirus, or their complementary RNA and/or DNA, into contact with a composition comprising a nucleotide fragment defined above.

DEFINITIONS

Before detailing the invention, various terms used in the description and the claims are now defined.

Strain or isolate is understood to mean any infectious and/or pathogenic biological fraction containing, for example, viruses and/or bacteria and/or parasites, generating a pathogenic and/or antigenic power, harbored by a culture or a live host; by way of example, a viral strain according to the preceding definition may contain a co-infectious agent, for example a pathogenic protist.

The term "MSRV" used in the present description designates any pathogenic and/or infectious agent, as associated with MS, in particular a viral species, the attenuated strains of said viral species, or the interfering defective particles or particles containing co-encapsidated genomes or alternatively genomes recombined with a portion of the MSRV-1 genome, which are derived from this species. It is known that viruses and particularly viruses containing RNA exhibit variability, following in particular relatively high rates of spontaneous mutation, which will be taken into account below to define the concept of equivalence.

Human virus is understood to mean a virus capable of infecting or of being harbored by human beings.

Given all the natural or induced variations and/or recombination which may be encountered in practice in the present invention, the objects thereof, defined above and in the claims, have been expressed by comprising the equivalents or derivatives of the various biological materials defined below, in particular homologous nucleotide or peptide sequences.

The variant of a virus or of a pathogenic and/or infectious agent according to the invention comprises at least one antigen recognized by at least one antibody directed against at least one corresponding antigen of said virus and/or of said pathogenic and/or infectious agent, and/or a genome in which any portion is detected by at least one hybridization probe, and/or at least one nucleotide amplification primer specific for said virus and/or pathogenic and/or infectious agent, under defined hybridization conditions well known to persons skilled in the art.

According to the invention, a nucleotide fragment or an oligonucleotide or a polynucleotide is a stretch of monomers, or a biopolymer, characterized by the informational sequence of the natural nucleic acids, which is capable of hybridizing to any other nucleotide fragment under predefined conditions, it being possible for the stretch to contain monomers of different chemical structures and to be obtained from a natural nucleic acid molecule and/or by genetic recombination and/or by chemical synthesis; a nucleotide fragment may be identical to a genomic fragment of the MSRV-1 virus considered by the present invention, in particular a gene of the latter, for example pol or env in the case of said virus.

Thus, a monomer may be a natural nucleic acid nucleotide in which the constituent components are a sugar, a phosphate group and a nitrogen base; in RNA, the sugar is ribose; in DNA, the sugar is 2-deoxyribose; depending on whether DNA or RNA is involved, the nitrogen base is chosen from adenine, guanine, uracil, cytosine, thymine; or the nucleotide may be modified in at least one of the three constituent components; by way of example, the modification may occur at the level of the bases, generating modified bases such as inosine, 5-methyl-deoxycytidine, deoxyuridine, 5-dimethylaminodeoxyuridine, 2,6-diaminopurine, 5-bromodeoxyuridine and any other modified base promoting hybridization; at the level of the sugar, the modification may consist in the replacement of at least one deoxyribose with a polyimide, and at the level of the phosphate group, the modification may consist in its replacement with esters, in particular chosen from the esters of diphosphate, of alkyl and arylphosphonate and of phosphorothioate.

"Informational sequence" is understood to mean any ordered series of monomers, whose chemical nature and in which the order in a reference direction, constitute or otherwise a functional information of the same quality as that for the natural nucleic acids.

Hybridization is understood to mean the process during which, under appropriate operating conditions, two nucleotide fragments, having sufficiently complementary sequences, become annealed to form a complex, in particular a double or triple, structure, preferably in helical form.

A probe comprises a nucleotide fragment synthesized by the chemical route or obtained by digestion or enzymatic cleavage of a longer nucleotide fragment, comprising at least six monomers, advantageously from 10 to 100 monomers, preferably 10 to 30 monomers, and possessing a hybridization specificity under defined conditions; preferably, a probe possessing less than 10 monomers is not used alone, but is used in the presence of other probes which are equally short in length or otherwise; under certain specific conditions, it may be useful to use probes which are greater than 100 monomers in size; a probe may be used in particular for diagnostic purposes, and it may be, for example, capture and/or detection probes.

The capture probe may be immobilized on a solid support by any appropriate means, that is to say directly or indirectly, for example by covalent bonding or passive adsorption.

The detection probe may be labeled by means of a marker chosen in particular from radioactive isotopes, enzymes chosen in particular from peroxidase and alkaline phosphatase and those capable of hydrolyzing a chromogenic, fluorigenic or luminescent substrate, chromophoric chemical compounds, chromogenic, fluorigenic or luminescent compounds, analogs of nucleotide bases, and biotin.

The probes used for diagnostic purposes of the invention may be used in all known hybridization techniques, and in particular the so-called "DOT-BLOT" technique, "SOUTHERN BLOT" technique, "NORTHERN BLOT" technique which is a technique identical to the "SOUTHERN BLOT" technique but which uses RNA as target, the SANDWICH technique; advantageously, the SANDWICH technique is used in the present invention, comprising a specific capture probe and/or a specific detection probe, it being understood that the capture probe and the detection probe must have a nucleotide sequence which is at least partially different.

Any probe according to the present invention may hybridize in vivo or in vitro with the RNA and/or with the DNA, in order to block the replication, in particular translation and/or transcription, phenomena and/or to degrade said DNA and/or RNA.

A primer is a probe comprising at least six monomers, and advantageously from 10 to 30 monomers, possessing hybridization specificity under defined conditions, for the initiation of an enzymatic polymerization, for example in an amplification technique such as PCR (Polymerase Chain Reaction), in an extension method such as sequencing, in a reverse transcription method and the like.

Two nucleotide or peptide sequences are said to be equivalent or derived with respect to each other, or with respect to a reference sequence, if functionally the corresponding biopolymers can play substantially the same role, without being identical, in relation to the application or use considered, or in the technique in which they are involved; particularly equivalent are two sequences obtained because of the natural variability, in particular spontaneous mutation, of the species from which they were identified, or induced mutation, as well as two homologous sequences, the homology being defined below.

"Variability" is understood to mean any spontaneous or induced modification of a sequence, in particular by substitution, and/or insertion, and/or deletion of nucleotides and/or of nucleotide fragments, and/or extension and/or shortening of the sequence at least at one of the ends; a nonnatural variability may result from the genetic engineering techniques used, for example from the choice of the degenerate or nondegenerate synthetic primers selected to amplify a nucleic acid; this variability may result in modifications of any starting sequence, considered as a reference, and which may be expressed by a degree of homology with respect to said reference sequence.

Homology characterizes the degree of identity of two compared nucleotide or peptide fragments; it is measured by the percentage identity which is in particular determined by direct comparison of nucleotide or peptide sequences, with respect to reference nucleotide or peptide sequences.

Any nucleotide fragment is said to be equivalent to or derived from a reference fragment if it has a nucleotide sequence equivalent to the sequence of the reference fragment; according to the preceding definition, in particular equivalent to a reference nucleotide fragment are:

(a) any fragment capable of hybridizing, at least partially, with the complementary to the reference fragment, (b) any fragment whose alignment with the reference fragment leads to the identification of identical contiguous bases, in a greater number than with any other fragment obtained from another taxonomic group, (c) any fragment resulting or capable of resulting from the natural variability of the species from which it is obtained, (d) any fragment which may result from genetic engineering techniques applied to the reference fragment, (e) any fragment, containing at least eight contiguous nucleotides, encoding a peptide homologous or identical to the peptide encoded by the reference fragment, (f) any fragment different from the reference fragment through insertion, deletion, substitution of at least one monomer, extension, or shortening at least at one of its ends; for example, any fragment corresponding to the reference fragment, flanked at least at one of its ends by a nucleotide sequence not encoding a polypeptide.

Polypeptide is understood to mean in particular any peptide of at least two amino acids, in particular oligopeptide, protein, extracted, separated, or substantially isolated or synthesized, through the involvement of humans, in particular those obtained by chemical synthesis, or through expression in a recombinant organism.

Polypeptide partially encoded by a nucleotide fragment is understood to mean a polypeptide having at least three amino acids encoded by at least nine contiguous monomers included in said nucleotide fragment.

An amino acid is said to be analogous to another amino acid when their respective physicochemical characteristics, such as polarity, hydrophobicity and/or basicity, and/or acidity, and/or neutrality, are substantially the same; thus, a leucine is analogous to an isoleucine.

Any polypeptide is said to be equivalent to or derived from a reference polypeptide if the polypeptides compared have substantially the same properties, and in particular the same antigenic, immunological, enzymatic and/or molecular recognition properties; in particular equivalent to a reference polypeptide is:

(a) any polypeptide possessing a sequence in which at least one amino acid has been replaced by an analogous amino acid, (b) any polypeptide having an equivalent peptide sequence, obtained by natural or induced variation of said reference polypeptide, and/or of the nucleotide fragment encoding said polypeptide, (c) a mimotope of said reference polypeptide, (d) any polypeptide from whose sequence one or more amino acids of the L series are replaced by an amino acid of the D series, and vice versa, (e) any polypeptide into whose sequence a modification of the side chains of the amino acids has been introduced, such as for example an acetylation of the amine-containing functions, a carboxylation of the thiol functions, an esterification of the carboxyl functions, (f) any polypeptide in whose sequence one or more peptide bonds have been modified, such as for example the carba, retro, inverso, retro-inverso, reduced, and methylene-oxy bonds, (g) any polypeptide in which at least one antigen is recognized by an antibody directed against a reference polypeptide.

The percentage identity characterizing the homology between two peptide fragments compared is according to the present invention at least 50% and preferably at least 70%.

Given that a virus possessing a reverse transcriptase enzymatic activity may be genetically characterized both in RNA and DNA form, both the viral DNA and RNA will be mentioned in order to characterize the sequences relative to a virus possessing such a reverse transcriptase activity, termed MSRV-1 according to the present description.

The expressions of order which are used in the present description and the claims, such as "first nucleotide sequence", are not selected to express a particular order, but to define the invention more clearly.

Detection of a substance or agent is understood below to mean an identification, a quantification or a separation or isolation of said substance or of said agent.

BRIEF DESCRIPTION OF THE DRAWINGS

The invention will be understood more clearly on reading the detailed description which follows which is made with reference to the appended Figures.

FIG. 2 represents the nucleotide sequence of the clone called CL6-5' (SEQ ID NO: 4) and three potential reading frames in amino acids presented under the nucleotide sequence.

FIG. 3 represents the nucleotide sequence of the clone called CL6-3' (SEQ ID NO: 6) and three potential reading frames in amino acids presented under the nucleotide sequence.

FIG. 4 represents the nucleotide sequence of the clone called C15 (SEQ ID NO: 9) and three potential reading frames in amino acids presented under the nucleotide sequence.

FIG. 5 represents the nucleotide sequence of the clone called 5M6 (SEQ ID NO: 12) and three potential reading frames in amino acids presented under the nucleotide sequence.

FIG. 6 represents the nucleotide sequence of the clone called CL2 (SEQ ID NO: 21) and three potential reading frames in amino acids presented under the nucleotide sequence.

FIG. 7 represents a potential reading frame in amino acids expressed by pET28C-clone 2 (SEQ ID NO: 40) and presented under the nucleotide sequence.

FIG. 8 represents a potential reading frame in amino acids expressed by pET21C-clone 2 (SEQ ID NO: 41) and presented under the nucleotide sequence.

FIG. 9 represents the nucleotide sequence of the clone called LB13 (SEQ ID NO: 30) and three potential reading frames in amino acids presented under the nucleotide sequence.

FIG. 10 represents the nucleotide sequence of the clone called LA15 (SEQ ID NO: 31) and three potential reading frames in amino acids presented under the nucleotide sequence.

FIG. 11 represents the nucleotide sequence of the clone called LB16 (SEQ ID NO: 16) and three potential reading frames in amino acids presented under the nucleotide sequence.

FIG. 12 represents the promoter activity expressed in cpm/4 min of the U3R sequences subcloned from LTRs of different origins into the plasmid PCAT3. PCAT3 means plasmid alone, PCAT-PH74 means plasmid plus endogenous U3R clone expressed in the placenta, PCATc16 means plasmid plus U3R clone amplified in the RNA of an MS plasma, PCAT-5M6 means plasmid plus U3R region amplified in the cellular DNA, "no plasmid" means absence of plasmid in the test.

FIG. 13 represents the MSRV1 env and 3' LTR sequences (which together form SEQ ID NO: 42). The horizontal arrows indicate the start of the env, U3 and R regions. In the env region, the signal peptide and the potential immunosuppressive region are underlined, the potential glycosilation sites are boxed and the potential cleavage sites are indicated by vertical arrows. In the U3R region: the regulatory element CART and the TATA Box are underlined, the "cap" site and the polyadenylation signal are also indicated.

FIG. 14 represents the 5' LTR(RU5) region followed by a PBS site (primer binding site) complementary to the Trp tRNA and by a gag gene encoding a protein of about 487 amino acids (which together form SEQ ID NO: 43). The amino acids conserved in the nucleocapsid are underlined twice. The amino acids defining the region of greatest homology in the capsid are in bold and underlined once. The / symbols in the amino acid sequence indicate variations observed depending on the clones and, in the nucleotide sequence, they indicate frame jumps in some clones. The boxed regions correspond to epitopes identified by peptide analysis of the C-terminal region.

FIG. 15 represents the integrase region of MSRV1 (SEQ ID NO: 44), the nucleotide sequence and the amino acid sequence deduced from the integrase region corresponding to clone 87-23. In FIG. 15, // means a frame jump which has been suppressed in order to restore the potential ORF. The letters in underlined bold characters represent the conserved amino acids in the retroviral integrases.

FIG. 16 describes the nucleotide and peptide sequences of clone B13 (identical to clone FBd13 described in previous applications) with indication of the ORFs and stop codons represented by a dot (SEQ ID NO: 45). The underlined region in bold represents the potential immunosuppressive domain. The single underlined domain represents the start of the 3' LTR.

DETAILED DESCRIPTION OF PREFERRED EMBODIMENTS

Example 1

Figure 1:
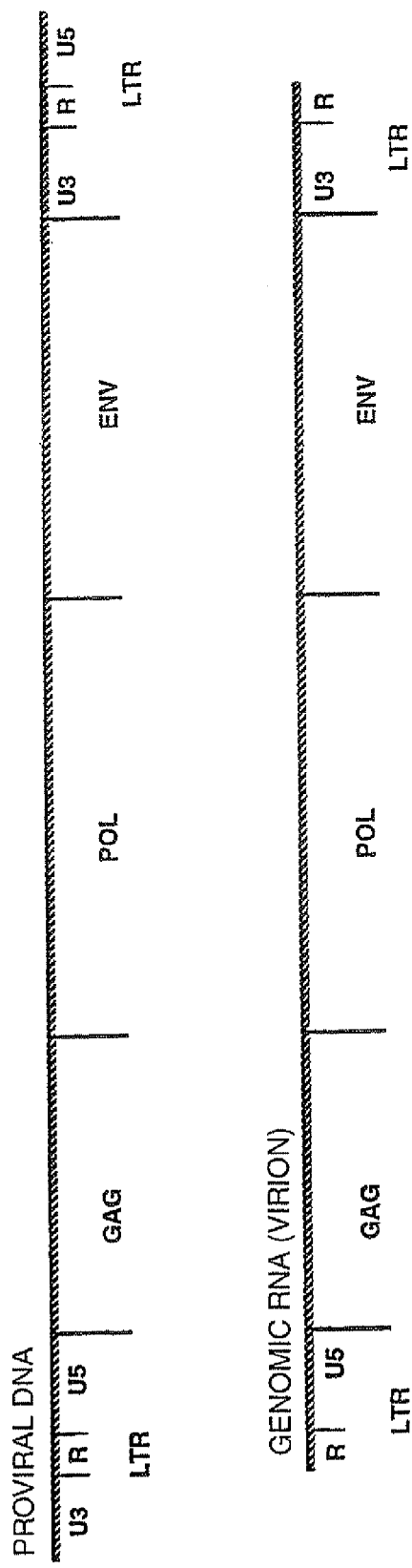
FIG. 1 represents the general structure of the proviral DNA and the genomic RNA of MSRV-1.

Preparation of a CL6-5' Region Encoding the N-Terminal End of Integrase and of a CL6-3' Region Containing the 3' Terminal Sequence of the MSRV-1 Genome A 3' RACE was carried out on the total RNA extracted from plasma from a patient suffering from MS. A healthy control plasma, treated under the same conditions, was used as negative control. The synthesis of cDNA was carried out with an oligo dT primer identified by SEQ ID NO: 1 (5' GAC TCG CTG CAG ATC GAT TTT TTT TTT TTT TTT T 3') and the reverse transcriptase "Expand™ RT" from Boehringer according to the conditions recommended by the company. A PCR was carried out with the enzyme Klentaq (Clontech) under the following conditions: 94° C. 5 min then 93° C. 1 min, 58° C. 1 min, 68° C. 3 min over 40 cycles and 68° C. for 8 min, with a final reaction volume of 50 µl.

Primers used for the PCR:

5' primer, identified by SEQ ID NO: 2

5' GCC ATC AAG CCA CCC AAG AAC TCT AA CTT 3';

3' primer, identified by SEQ ID NO: 1

A second so-called "seminested" PCR was carried out with a 5' primer situated inside the region already amplified. This second PCR was carried out under the same experimental conditions as those used for the first PCR, using 10 µl of the amplification product derived from the first PCR.

Primers used for the seminested PCR:
5' primer, identified by SEQ ID NO: 3

```
5' CCA ATA GCC AGA CCA TTA TAT ACA CTA ATT 3';
```

3' primer, identified by SEQ ID NO: 1

The primers SEQ ID NO: 2 and SEQ ID NO: 3 are specific for the pol region of MRSV-1.

An amplification product of 1.9 Kb was obtained for the plasma of the MS patient. The corresponding fragment was not observed for the healthy control plasma. This amplification product was cloned in the following manner:

The amplified DNA was inserted into a plasmid with the aid of the TA Cloning Kit®. The 2 µl of DNA solution were mixed with 5 µl of sterile distilled water, 1 µl of a 10 times concentrated ligation buffer "10× LIGATION BUFFER", 2 µl of "pCR™ VECTOR" (25 ng/ml) and 1 µl of "T4 DNA LIGASE". This mixture was incubated overnight at 12° C. The next steps were carried out in accordance with the instructions for the TA Cloning kite (Invitrogen). At the end of the procedure, the white colonies of recombinant bacteria (white) were subcultured so as to be cultured and allow the extraction of the plasmids incorporated according to the so-called "miniprep" procedure. The plasmid preparation of each recombinant colony was cut with an appropriate restriction enzyme and analyzed on agarose gel. The plasmids possessing an insert detected under UV light after staining the gel with ethidium bromide were selected for the sequencing of the insert after hybridization with a primer complementary to the Sp6 promoter present on the cloning plasmid of the TA Cloning Kit®. The reaction prior to the sequencing was then carried out according to the method recommended for using the sequencing kit "PRISM™ Ready Reaction AmpliTaq° FS, DyeDeoxy™ Terminator" (Applied Biosystems, ref. 402119) and the automated sequencing was carried out on the Applied Biosystems 373 A and 377 apparatus, according to the manufacturer's instructions.

The clone obtained contains a CL6-5' region encoding the N-terminal end of integrase and a CL6-3' region corresponding to the 3' terminal region of MSRV-1 and making it possible to define the end of the envelope (234 bp) and the U3 and R (401 bp) regions of the MSRV1 retrovirus.

The region corresponding to the N-terminal end of integrase is represented by its nucleotide sequence (SEQ ID NO: 4) in FIG. 2. The three potential reading frames are presented by their amino acid sequence under the nucleotide sequence, and the amino acid sequence of the N-terminal end of integrase is identified by SEQ ID NO: 5.

The C16-3' region is represented by its nucleotide sequence (SEQ ID NO: 6) in FIG. 3. The three potential reading frames are presented by their amino acid sequence under the nucleotide sequence. An amino acid sequence corresponding to the C-terminal end of the MSRV-1 env protein is identified by SEQ ID NO: 7.

In order to evaluate the promoter activity of the LTR obtained from clone 6 (c16), a test of promoter activity using the enzyme CAT (chloramphenicol acetyl transferase) was carried out with the corresponding U3R region. In parallel, a clone containing the same U3R region of endogenous retroviral RNA expressed in normal placenta (PH74) and a clone (5M6) obtained from DNA were tested. The result presented in FIG. 12 shows a very high promoter activity of the LTR derived from MS plasma (c16) and a significantly much lower activity with the sequences of non-MS endogenous origin.

Example 2

Preparation of the C15 Clone Containing the Region Encoding a Portion of the MSRV-1 Retrovirus Envelope A RT-PCR was carried out on the total RNA extracted from virions concentrated by ultra-centrifugation of a synoviocyte culture supernatant obtained from an MS patient. The synthesis of cDNA was carried out with an oligo dT primer and the reverse transcriptase "Expand™ RT" from Boehringer according to the conditions recommended by the company. A PCR was carried out with the Expand™ Long Template PCR System (Boehringer) under the following conditions: 94° C. 5 min then 93° C. 1 min, 60° C. 1 min, 68° C. 3 min over 40 cycles and 68° C. for 8 min and with a final reaction volume of 50 µl.

Primers used for the PCR:
5' primer, identified by SEQ ID NO: 2

```
5' GCC ATC AAG CCA CCC AAG AAC TCT AA CTT 3';
```

3' primer, identified by SEQ ID NO: 8

```
5' TGG GGT TCC ATT TGT AAG ACC ATC TGT AGC TT 3'
```

A second so-called "seminested" PCR was carried out with a 5' primer situated inside the region already amplified. This second PCR was carried out under the same experimental conditions as those used for the first PCR (except that 30 cycles were used instead of 40), using 10 µl of the amplification product derived from the first PCR.

Primers used for the seminested PCR:
5' primer, identified by SEQ ID NO: 3

```
5' CCA ATA GCC AGA CCA TTA TAT ACA CTA ATT 3';
```

3' primer, identified by SEQ ID NO: 8

The primers SEQ ID NO: 2 and SEQ ID NO: 3 are specific for the pol region of MRSV-1. The primer SEQ ID NO: 8 is specific for the sequence FBdl3 (also called B13) and is located in the conserved env region among the oncoretroviruses.

An amplification product of 1932 by was obtained and cloned in the following manner:

the amplified DNA was inserted into a plasmid with the aid of the TA Cloning Kit®. The various steps were carried out in accordance with the instructions for the TA Cloning Kit® (Invitrogen). At the end of the procedure, the white colonies of recombinant bacteria (white) were subcultured so as to be cultured and allow the extraction of the plasmids incorporated according to the so-called "miniprep" procedure. The plasmid preparation of each recombinant colony was cut with an appropriate restriction enzyme and analyzed on agarose gel. The plasmids possessing an insert detected under UV light after staining the gel with ethidium bromide were selected for the sequencing of the insert after hybridization with a primer complementary to the SP6 promoter present on the cloning plasmid of the TA Cloning Kit®. The reaction prior to the sequencing was then carried out according to the method recommended for using the sequencing kit "PRISM™ Ready Reaction AmpliTaqR FS, DyeDeoxy™ Terminator" (Applied Biosystems, ref. 402119) and the automated sequencing was carried out on the Applied Biosystems 373 A and 377 apparatus, according to the manufacturer's instructions.

The C15 clone obtained contains a region corresponding to the region of the MSRV-1 envelope of 1481 bp.

The env region of the C15 clone is represented by its nucleotide sequence (SEQ ID NO: 9) in FIG. 4. The three potential reading frames of this clone are presented by their amino acid sequence under the nucleotide sequence. The reading frame corresponding to an MSRV-1 structural env protein is identified by SEQ ID NO: 10.

Figure 13:
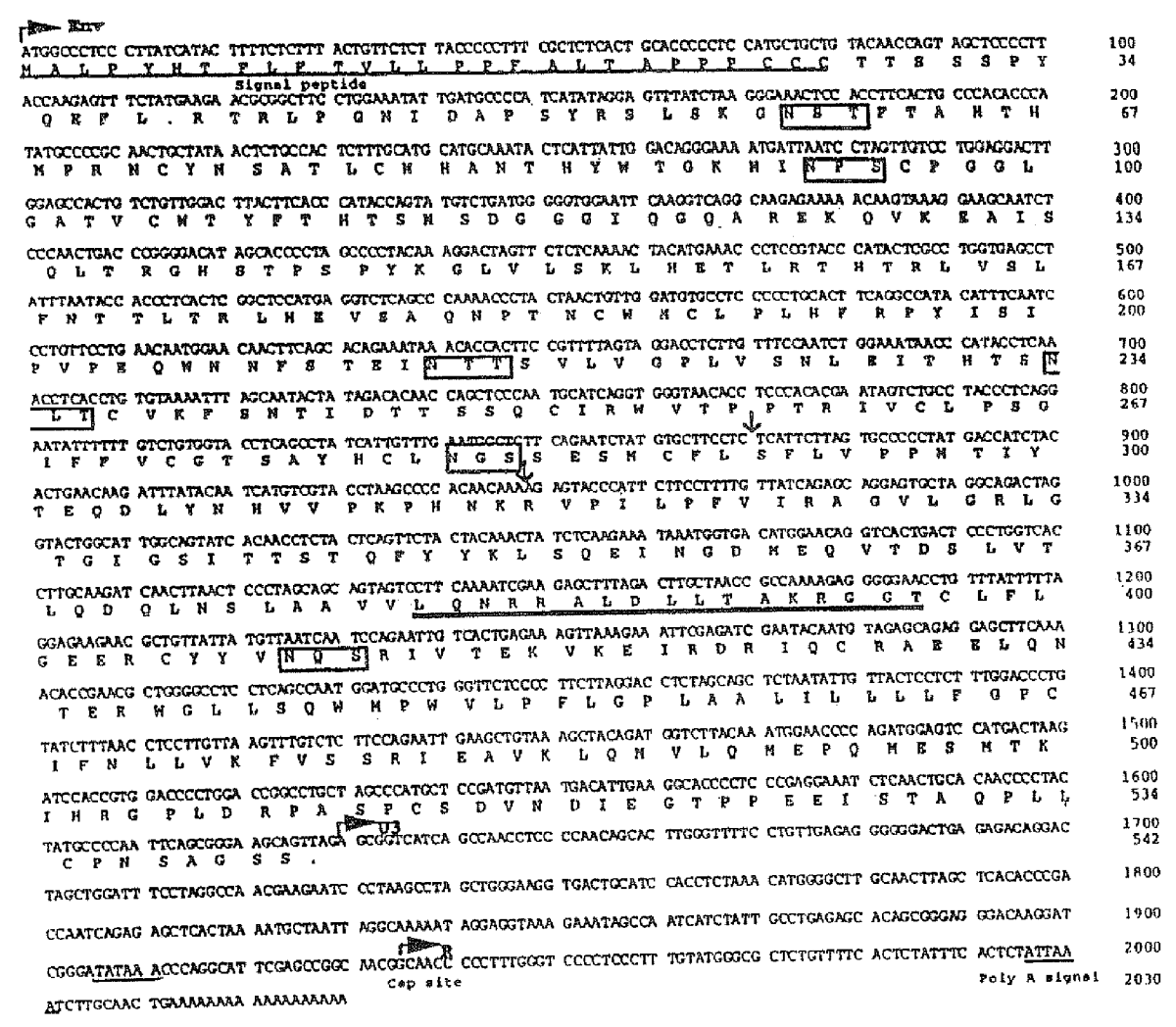

From the defined sequences obtained from clones c16 and C15, it was possible to produce a plasmid construct encoding a complete envelope followed by the 3' LTR, as presented in FIG. 13 with the corresponding reading frame.

Example 3

Preparation of a 5M6 Clone Containing the Sequences of the 3' Terminal Region of the Envelope, Followed by the MSRV-1 Proviral Type U3, R and U5 Sequences A monodirectional PCR was carried out on the DNA extracted from immortalized B lymphocytes in culture from an MS patient. The PCR was carried out with Expand™ Long Template PCR System (Boehringer) under the following conditions: 94° C. 3 min then 93° C. 1 min, 60° C. 1 min, 68° C. 3 min over 10 cycles, then 93° C. 1 min, 60° C. 1 min with 15 sec of extension at each cycle, 68° C. 3 min over 35 cycles and 68° C. for 7 min and with a final reaction volume of 50

The primer used for the PCR identified by SEQ ID NO: 11 is 5' TCA AAA TCG AAG AGC TTT AGA CTT GCT AAC CG 3'.

The primer of SEQ ID NO: 11 is specific for the env region of the C15 clone.

An amplification product of 1673 by was obtained and cloned in the following manner:

the amplified DNA was inserted into a plasmid with the aid of the TA Cloning Kit®. The various steps were carried out in accordance with the instructions for the TA Cloning Kit® (Invitrogen). At the end of the procedure, the white colonies of recombinant bacteria (white) were subcultured so as to be cultured and allow the extraction of the plasmids incorporated according to the so-called "miniprep" procedure. The plasmid preparation of each recombinant colony was cut with an appropriate restriction enzyme and analyzed on agarose gel. The plasmids possessing an insert detected under UV light after staining the gel with ethidium bromide were selected for the sequencing of the insert after hybridization with a primer complementary to the T7 promoter present on the cloning plasmid of the TA Cloning Kit®. The reaction prior to the sequencing was then carried out according to the method recommended for using the sequencing kit "PRISM™ Ready Reaction AmpliTaq° FS, DyeDeoxy™ Terminator" (Applied Biosystems, ref. 402119) and the automated sequencing was carried out on the Applied Biosystems 373 A and 377 apparatus, according to the manufacturer's instructions.

The 5M6 clone obtained contains a region corresponding to the 3' region of the MSRV-1 envelope of 492 by followed by the regions U3, R and U5 (837 bp) of MSRV1.

The 5M6 clone is represented by its nucleotide sequence (SEQ ID NO: 12) in FIG. 5. The three potential reading frames of this clone are presented by their amino acid sequence under the nucleotide sequence. The reading frame corresponding to the C-terminal end of the MSRV-1 env protein is identified by SEQ ID NO: 13.

Example 4

Preparation of the LB16 Clone Containing the Region Encoding the MSRV-1 Retrovirus Integrase An RT-PCR was carried out on the total RNA treated with DNAseI and extracted from a choroid plexus obtained from an MS patient. The synthesis of cDNA was carried out with an oligo dT primer and the reverse transcriptase "Expand™ RT" from Boehringer according to the conditions recommended by the company. A "no RT" control was carried out in parallel on the same material. A PCR was carried out with Taq polymerase (Perkin Elmer) under the following conditions: 95° C. 5 min, then 95° C. 1 min, 55° C. 1 min, 72° C. 2 min over 35 cycles and 72° C. for 8 min and with a final reaction volume of 50

Primers used for the PCR:
5' primer, identified by SEQ ID NO: 14

5' GGC ATT GAT AGC ACC CAT CAG 3';

3' primer, identified by SEQ ID NO: 15

5' CAT GTC ACC AGG GTG GAA TAG 3'

The primer SEQ ID NO: 14 is specific for the pol region of MSRV-1 and more precisely similar to the integrase region described above. The primer SEQ ID NO: 15 was defined on sequences of the clones obtained during preliminary tests.

An amplification product of about 760 by was obtained only in the test with RT and was cloned in the following manner:

the amplified DNA was inserted into a plasmid with the aid of the TA Cloning Kit®. The various steps were carried out in accordance with the instructions for the TA Cloning Kit® (Invitrogen). At the end of the procedure, the white colonies of recombinant bacteria (white) were subcultured so as to be cultured and allow the extraction of the plasmids incorporated according to the so-called "miniprep" procedure. The plasmid preparation of each recombinant colony was cut with an appropriate restriction enzyme and analyzed on agarose gel. The plasmids possessing an insert detected under UV light after staining the gel with ethidium bromide were selected for the sequencing of the insert after hybridization with a primer complementary to the T7 promoter present on the cloning plasmid of the TA Cloning Kit®. The reaction prior to the sequencing was then carried out according to the method recommended for using the sequencing kit "PRISM™ Ready Reaction AmpliTagR FS, DyeDeoxy™ Terminator" (Applied Biosystems, ref. 402119) and the automated sequencing was carried out on the Applied Biosystems 373 A and 377 apparatus, according to the manufacturer's instructions.

The LB16 clone obtained contains the sequences corresponding to integrase. The nucleotide sequence of this clone was identified by SEQ ID NO: 16 in FIG. 11, three reading frames are determined.

Example 5

Preparation of a Clone 2, CL2, Containing in 3' a Portion Homologous to the Pol Gene, Corresponding to the Protease Gene, and to the Gag Gene (GM3) Corresponding to the Nucleocapsid, and a New 5'Coding Region, Corresponding to the Gag Gene More Specifically the Template and the Capsid of MSRV-1.

A PCR amplification was carried out on the total RNA extracted from 100 µl of plasma from a patient suffering from MS. A water control, treated under the same conditions, was used as negative control. The synthesis of cDNA was carried out with 300 pmol of a random primer (GIBCO-BRL, France) and the reverse transcriptase "Expand RT" (BOEHRINGER MANNHEIM, France) according to the conditions recommended by the company. An amplification by PCR ("polymerase chain reaction") was carried out with the enzyme Tag polymerase (Perkin Elmer, France) using 10 µl of cDNA under the following conditions: 94° C. 2 min, 55° C. 1 min, 72° C. 2 min then 94° C. 1 min, 55° C. 1 min, 72° C. 2 min over 30 cycles and 72° C. for 7 min with a final reaction volume of 50

Primers used for the PCR amplification:
5' primer, identified by SEQ ID NO: 17

```
5' CGG ACA TCC AAA GTG ATG GGA AAC G 3';
```

3' primer, identified by SEQ ID NO: 18

```
5' GGA CAG GAA AGT AAG ACT GAG AAG GC 3'
```

A second amplification by so-called "seminested" PCR was carried out with a 5' primer situated inside the region already amplified. This second PCR was carried out under the same experimental conditions as those used during the first PCR, using 10 µl of the amplification product derived from the first PCR.

Primers used for the amplification by seminested PCR:
5' primer, identified by SEQ ID NO: 19

```
5' CCT AGA ACG TAT TCT GGA GAA TTG GG 3';
```

3' primer, identified by SEQ ID NO: 20

```
5' TGG CTC TCA ATG GTC AAA CAT ACC CG 3'
```

The primers SEQ ID NO: 18 and SEQ ID NO: 20 are specific for the pol region, clone G+E+A, more specifically the E region: nucleotide position No. 423 to No. 448. The primers used in the 5' region were defined on sequences of clones obtained during preliminary tests.

An amplification product of 1511 by was obtained from the RNA extracted from the plasma of an MS patient. The corresponding fragment was not observed for the water control. This amplification product was cloned in the following manner.

The amplified DNA was inserted into a plasmid with the aid of the TA Cloning Kit™. The 2 µl of DNA solution were mixed with 5~t1 of sterile distilled water, 1 µl of a 10 times concentrated ligation buffer "10× LIGATION BUFFER", 2 µl of "pCR™ VECTOR" (25 ng/ml) and 1 µl of "T4 DNA LIGASE". This mixture was incubated overnight at 14° C. The following steps were carried out in accordance with the instructions of the TA Cloning Kit® (Invitrogen). The mixture was plated after transformation of the ligation into E. coli INVαF' bacteria. At the end of the procedure, the white colonies of recombinant bacteria were subcultured so as to be cultured and allow the extraction of the plasmids incorporated according to the so-called "DNA minipreparation" procedure (17). The plasmid preparation of each recombinant colony was cut with the restriction enzyme EcoRI and analyzed on agarose gel. The plasmids possessing an insert detected under UV light after staining the gel with ethidium bromide were selected for the sequencing of the insert after hybridization with a primer domplementary to the T7 promoter present on the cloning plasmid of the TA Cloning Kit®. The reaction prior to the sequencing was then carried out according to the method recommended for using the sequencing kit "PRISM™ Ready Reaction Amplitaq® FS, DyeDeoxy™ Terminator" (Applied Biosystems, ref. 402119) and the automated sequencing was carried out on the Applied Biosystems 373 A and 377 apparatus, according to the manufacturer's instructions.

The clone obtained, called CL2, contains a C-terminal region similar to the 5' terminal region of the clones G+E+A of MSRV-1, which makes it possible to define the C-terminal region of the gag gene and a new region corresponding to the N-terminal region of the MSRV-1 gag gene.

CL2 makes it possible to define a region of 1511 by having an open reading frame in the N-terminal region of 1077 by encoding 359 amino acids and a non-open reading frame of 454 by corresponding to the C-terminal region of the MSRV-1 gag gene.

The nucleotide sequence of CL2 is identified by SEQ ID NO: 21. It is represented in FIG. 6 with the potential reading frames in amino acids.

The 1077 by fragment of CL2 encoding 359 amino acids was amplified by PCR with the Pwo enzyme (5U/µl) (Boehringer Mannheim, France) using 1 µl of the DNA miniprepararation of clone 2 under the following conditions: 95° C. 1 min, 60° C. 1 min, 72° C. 2 min over 25 cycles and with a final reaction volume of 50 µl with the aid of the primers:

5' primer (BamHI), identified by SEQ ID NO: 23

```
5' TGC TGG AAT TCG GGA TCC TAG AAC GTA TTC 3'
(30 mer),
``` and
3' primer (HindIII), identified by SEQ ID NO: 24

```
5' AGT TCT GCT CCG AAG CTT AGG CAG ACT TTT 3'
(30 mer)
``` corresponding, respectively, to the nucleotide sequence of clone 2 at position −9 to 21 and 1066 to 1095.

The fragment obtained by PCR was linearized with BamHI and HindIII and subcloned into the expression vectors pET28C and pET21C (NOVAGEN) linearized with BamHI and HindIII. The sequencing of the DNA of the 1077 by fragment of clone 2 in the two expression vectors was carried out according to the method recommended for the use of the sequencing kit "PRISM™ Ready Reaction Amplitaqe° FS, DyeDeoxy™ Terminator" (Applied Biosystems, ref. 402119 and the automated sequencing was carried out on the Applied Biosystems 373 A and 377 apparatus, according to the manufacturer's instructions.

The expression of the nucleotide sequence of the 1077 by fragment of clone 2 by the expression vectors pET28C and pET21C are identified by SEQ ID NO: 25 and SEQ ID NO: 26, respectively.

Example 6

Expression of Clone 2 in *Escherichia Coli*

The constructs pET28c-clone 2 (1077 bp) and pET21C-clone 2 (1077 bp) synthesize, in the bacterial strain BL21 (DE3), a protein fused at the N- and C-terminus for the vector pET28C and the C-terminus for the vector pET21C with 6 Histidines, having an apparent molecular mass of about 45 kDa, identified by SDS-PAGE polyacrylamide gel electrophoresis (SDS=Sodium Dodecyl Sulfate) (Laemmli, 1970 (1)). The reactivity of the protein was demonstrated towards an anti-Histidine monoclonal antibody (DIANOVA) by the Western-blot technique (Towbin et al., 1979 (2)).

The recombinant proteins pET28c-clone 2 (1077 bp) and pET21C-clone 2 (1077 bp) were visualized by SDS-PAGE in the insoluble fraction after enzymatic digestion of the bacterial extracts with 50 µl of lysozyme (10 mg/ml) and ultrasound lysis.

The antigenic properties of the recombinant antigens pET28C-clone 2 (1077 bp) and pET21C-clone 2 (1077 bp) were tested by Western blot after solubilization of the bacterial pellet with 2% SDS and 50 mM β-mercaptoethanol. After incubation with sera from patients suffering from multiple sclerosis, the sera from neurological controls and the sera from controls at the Blood Transfusion. Center (CTS), the immunocomplexes were detected with the aid of an alkaline phosphatase-coupled goat serum anti-human IgG and anti-human IgM.

The results are presented in the table below.

TABLE

Reactivity of sera affected by multiple sclerosis and controls with the MSRV-1 recombinant protein gag clone 2 (1077 bp) = pET21C-clone 2 (1077 bp) and pET28C-clone 2 (1077 bp)[a]

| DISEASE | NUMBER OF INDIVIDUALS TESTED | NUMBER OF POSITIVE INDIVIDUALS |
|---|---|---|
| MS | 15 | 6 2 (+++), 2 (++), 2 (+) |
| NEUROLOGICAL CONTROLS | 2 | 1 (+++) |
| HEALTHY CONTROLS (CTS) | 22 | 1 (+/−) |

[a]The strips containing 1.5 µg of recombinant antigen pET-gag clone 2 (1077 bp) exhibit reactivity against sera diluted 1/100. The Western-Blot interpretation is based on the presence or absence of a specific pET-gag clone 2 (1077 bp) band on the strips. Positive and negative controls are included in each experiment.

These results show that, under the technical conditions used, about 40% of the human sera affected by multiple sclerosis which were tested react with the recombinant proteins pET28C-clone 2 (1077 bp) and pET21C-clone 2 (1077 bp). Reactivity was observed on a neurological control and it is of interest to note that the RNAs extracted from this serum, after the reverse transcriptase step, are also amplified by PCR in the pol region. This suggests that people who have not declared MS may also harbor and express this virus. On the other hand, an apparently healthy control (CTS donor) possesses anti-gag (clone 2, 1077 bp) antibodies. This is compatible with an immunity acquired against MSRV-1 independently of a declared associated autoimmune disease.

Example 7

Preparation of an LB13 Clone Containing in 3' a Portion Homologous to Clone 2 Corresponding to the Gag Gene and in 5' a Portion Homologous to the 5M6 Clone Corresponding to the U5 LTR Region An RT-PCR ("reverse transcriptase-polymerase chain reaction") was carried out using total RNA extracted from virions, obtained from supernatants of B lymphocyte cells of patients suffering from multiple sclerosis, concentrated by ultracentrifugations. The synthesis of cDNA was carried out with a specific primer SEQ ID NO: 27 and the reverse transcriptase "Expand™ RT" from BOEHRINGER MANNHEIM according to the conditions recommended by the company.

Primer used for the synthesis of the cDNA, identified by SEQ ID NO: 27:

5' CTT GGA GGG TGC ATA ACC AGG GAA T 3'

A PCR amplification was carried out with Tag polymerase (Perkin Elmer, France) under the following conditions: 94° C. 1 min, 55° C. 1 min, 72° C. 2 min over 35 cycles at 72° C. for 7 min and with a final reaction volume of 100

Primers used for the PCR amplification:
5' primer, identified by SEQ ID NO: 28

5' TGT CCG CTG TGC TCC TGA TC 3'

3' primer, identified by SEQ ID NO: 27

5' CTT GGA GGG TGC ATA ACC AGG GAA T 3'

A second so-called "seminested" PCR amplification was carried out with a 3' primer situated inside the region already amplified. This second amplification was carried out under the same experimental conditions as those used during the first amplification, using 10 µl of the amplification product derived from the first PCR.

Primers used for the "seminested" PCR amplification:
5' primer, identified by SEQ ID NO: 28

5' TGT CCG CTG TGC TCC TGA TC 3'

3' primer, identified by SEQ ID NO: 29

5' CTA TGT CCT TTT GGA CTG TTT GGG T 3'

The primers SEQ ID NO: 27 and SEQ ID NO: 29 are specific for the gag region, clone 2 nucleotide position No. 373-397 and No. 433-456. The primers used in the 5' region were defined on sequences of the clones obtained during preliminary tests.

An amplification product of 764 by was obtained and cloned in the following manner:

The amplified DNA was inserted into a plasmid with the aid of the TA Cloning Kit™. The 2 µl of DNA solution were mixed with 5 µl of sterile distilled water, 1 µl of a 10 times concentrated ligation buffer "10× LIGATION BUFFER", 2 µl of "pCR™ VECTOR" (25 ng/ml) and 1 µl of "T4 DNA LIGASE". This mixture was incubated overnight at 14° C. The following steps were carried out in accordance with the instructions of the TA Cloning Kit® (Invitrogen). The mixture was plated after transformation of the ligation into E. coli INVαF' bacteria. At the end of the procedure, the white colonies of recombinant bacteria were subcultured so as to be cultured and allow the extraction of the plasmids incorporated according to the so-called "DNA minipreparation" procedure (17). The plasmid preparation of each recombinant colony was cut with the restriction enzyme EcoRI and analyzed on agarose gel. The plasmids possessing an insert detected under UV light after staining the gel with ethidium bromide were selected for the sequencing of the insert after hybridization with a primer complementary to the T7 promoter present on the cloning plasmid of the TA Cloning Kit®. The reaction prior to the sequencing was then carried out according to the method recommended for using the sequencing kit "PRISM™ Ready Reaction Amplitaq® FS, DyeDeoxy™ Terminator" (Applied Biosystems, ref. 402119) and the automated sequencing was carried out on the Applied Biosystems 373 A and 377 apparatus, according to the manufacturer's instructions.

The LB13 clone obtained contains an N-terminal region of MSRV-1 gag gene homologous to clone 2 and an LTR corresponding to a portion of the U5 region. Between the U5 region and gag, a binding site for the transfer RNAs, the PBS "primer binding site", was identified.

The nucleotide sequence of the 764 by fragment of the LB13 clone in the plasmid "pCR™ vector" is represented in the identifier SEQ ID NO: 30.

The binding site for the transfer RNAs, having a sequence of PBS tryptophan type, was identified at nucleotide position No. 342-359 of the LB13 clone.

As this same PBS was found in the endogenous copies homologous to MSRV1, the endogenous family thus defined is henceforth called HERV W, according to the nomenclature proposed for the endogenous retrovirus families (W=tryptophan).

A short ORF of about 65 amino acids was found in the U5 region of the 5' LTR of the LB13 clone.

Sequence of the ORF (SEQ ID NO: 32):

PMASNRAITLTAWSKIPFLGIRETKNPRSENTRLATMLEAAHHHFGSSP

PLSWELWEQGPQVTIW.

The corresponding nucleotide sequence starting at an ATG codon is capable of being expressed in a subgenomic DNA from a proviral LTR (U3RU5).

Another clone, called LA15, was obtained on the total RNA extracted from virions concentrated by ultracentrifugation from a culture supernatant of synoviocytes obtained from a patient suffering from rheumatoid arthritis. The strategy for amplifying and cloning the LA15 clone is exactly the same which was used for the LB13 clone.

The nucleotide sequence of the LA15 clone, which is represented in the identifier SEQ ID NO: 31, is very similar to the LD13 clone. This suggests that the MSVR-1 retrovirus detected in multiple sclerosis has sequences which are similar to those found in rheumatoid arthritis.

Example 8

Reconstruction of an RU5-Gag Region From the Clones LB15, LB13, CL2 and CL17

The clones CL2 and LB13 have already been described in the preceding examples. The LB15 clone was obtained using the R sequence of the LTR of the c16 clone in order to define a primer in 5' and the antisense primers used are the same as for the LB13 clone. The CL17 clone was obtained by nested RT-PCR using the following primers:

(SEQ ID NO: 33)
5'-TCATGCAACTGCACTCTTCTGGTCCG-3'
(sense)

(SEQ ID NO: 34)
5'-TCTTGCACTAACCTCCACTGTCCGTTGG-3'
(antisense)

(SEQ ID NO: 35)
5'-ATCCCCCAGTAACAATTTGGTGACCACG-3'
(sense)

(SEQ ID NO: 36)
5'-TCGGGTCTAAGAGGGTACTTCCTTTGGTAGG-3'
(antisense)

The LB15 clone was obtained from virions obtained by culturing MS cells. The LB17 clone was obtained from culturing plasma from an MS patient.

Figure 14:
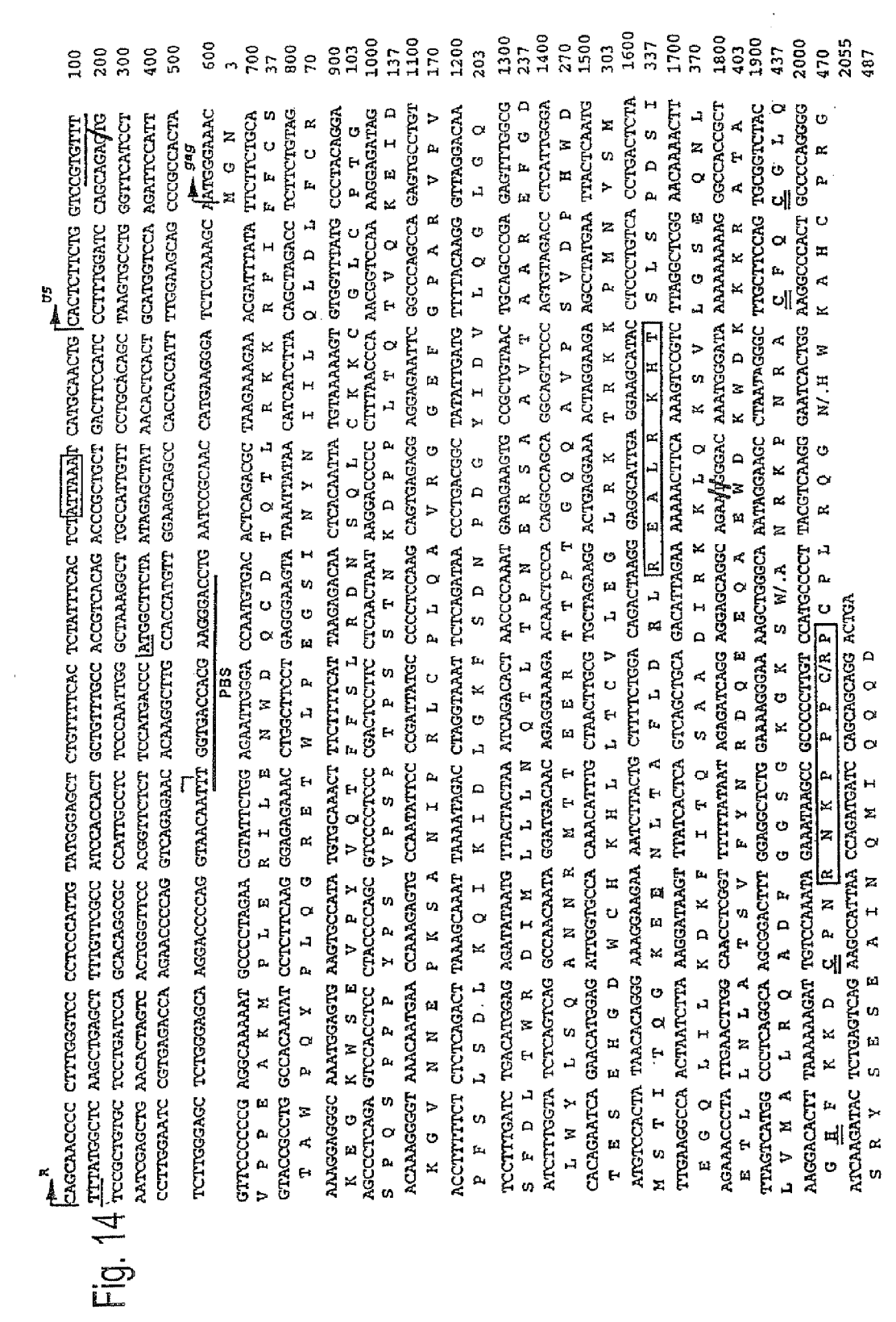

These overlapping clones made it possible to reconstruct an RU5-gag sequence with a potential ORF in the gag gene, as presented in FIG. 14.

Example 9

Preparation of a Clone 87-23

The region corresponding to integrase was amplified and cloned from MS plasma using a seminested RT PCR with the following primers situated in the pal and env regions of MSRV1.

In the pol region:

(SEQ ID NO: 37)
5'-TTACGCAGGTCTCAGGGATGAGCTT-3'
(sense-primary PCR)

(SEQ ID NO: 38)
5'-CGGCAGTAGCAGTCTTAGTATCTGAAGCAGTTA-3'
(sense-secondary PCR)

In the env region, (SEQ ID NO: 39)
5'-GGTACGGAGGGTTTCATGTAGTTTTGAG-3'
(anti-sense primary and secondary PCR)

The amplified clone contains 774 by in the pol/RT region, all the integrase region (1197 bp) and the start of the env region (480 bp). The nucleotide sequence corresponding to the integrase region and the translation to amino acids of the potential ORF are presented in FIG. 15.

Example 10

Figure 16:
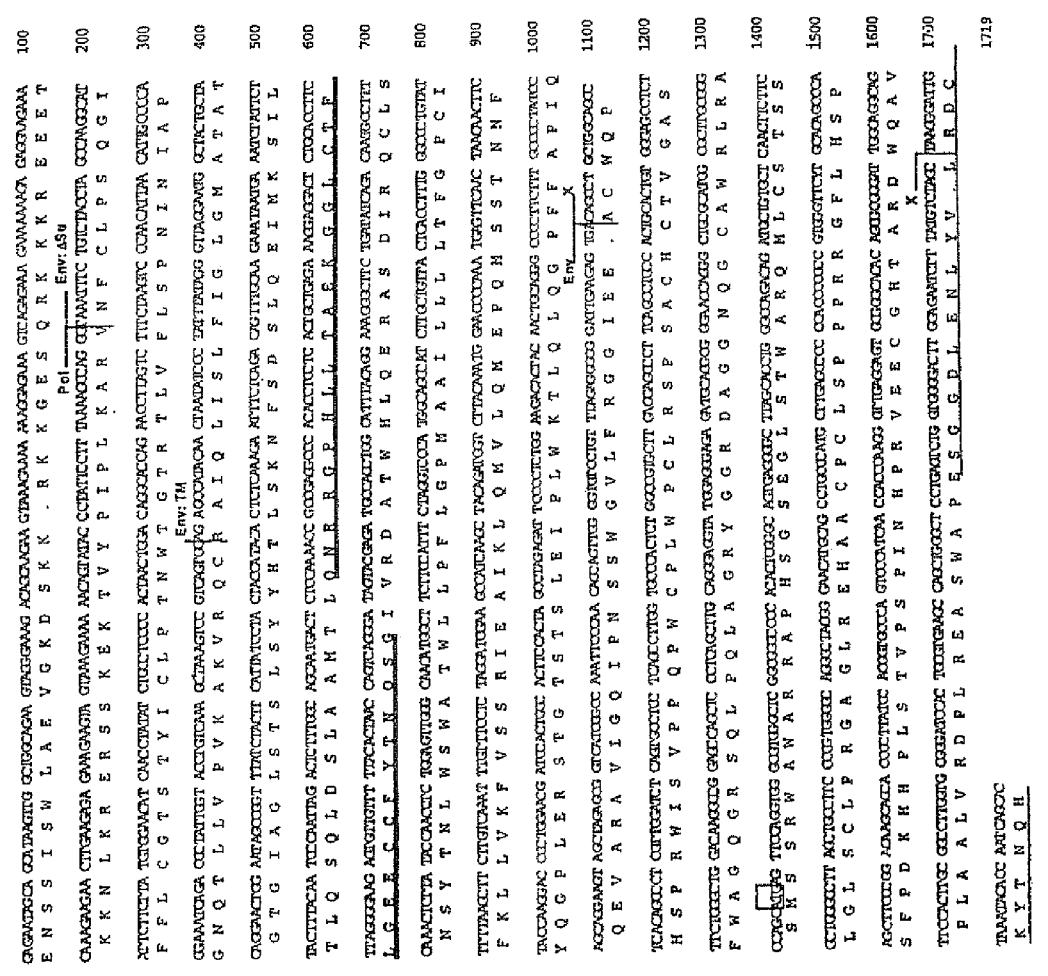

Confirmation of the Presence of RNA Containing Env Sequences Related to ERV9 in the Retroviral Particles Associated with the MSRV1 Genome Sequences related to ERV9 have been found in a minor proportion in the virion preparations obtained from MS compared with the MSRV1 sequences. The existence of phenomena of co-encapsidation of phylogenetically related endogenous sequences into retroviral particles produced by a replicative strain has been described. Surprisingly, an RNA region comprising an ORF starting in the 3' portion of env and continuing potentially into the 3' LTR has been found in various MS samples. In order to specify the existence of an ORF, transcription-translation tests were carried out and made it possible to show the reality of an env ORF containing the entire transmembrane (TM) portion and ending at the start of the putative LTR. However, an additional frame (ORFX) follows and continues in the 3' LTR. The two products of expression were visualized and their respective ORFs were subcloned. FIG. 16 represents the nucleotide and peptide sequences of the B13 clone already described, specifying the ORFs in the truncated env region and in the putative LTR. The presence of such RNAs may be responsible for recombinations with the replicative strain and consequently generate strains having a modified pathogenicity.

BIBLIOGRAPHIC REFERENCES (1) Laemmli U. K. Cleavage of structural proteins during the assembly of the head of bacteriophage T4.
Nature. (1970). 227: 680-685.

(2) Towbin. H., Staehelin T. & Gordon J. Electrophoretic transfer of proteins from polyacryalmide gels to nitrocellulose sheets: procedure and some applications. Proc. Natl. Acad. Sci. USA.
(1979). 76: 4350-4354.

What is claimed is:

1. An isolated polynucleotide comprising a nucleotide sequence selected from the group consisting of:
   (a) SEQ ID NO: 21,
   (b) the full-length sequences encoding a polypeptide having a peptide sequence selected from the group consisting of SEQ ID NOs: 25 and 26, and
   (c) the full-length complementary sequences to the sequences set forth in (a) or (b).

2. The isolated polynucleotide according to claim 1, wherein said polynucleotide is DNA.

3. The isolated polynucleotide according to claim 1, wherein said polynucleotide is RNA.

4. A recombinant vector comprising the polynucleotide defined in claim 1.

5. An expression vector comprising the polynucleotide defined in claim 1.

6. An isolated retroviral polynucleotide comprising:
   a C-terminal region of a gag gene comprising a nucleic acid having a nucleotide sequence selected from the group consisting of fragment 1-1418 of SEQ ID NO: 21 and the full-length complementary sequence thereof; and an N-terminal region of a pol gene comprising a nucleic acid having a nucleotide sequence selected from the group consisting of fragment 1419-1511 of SEQ ID NO: 21 and the full-length complementary sequence thereof.

7. An isolated retroviral polynucleotide comprising a gag gene that encodes a polypeptide having a peptide sequence selected from the group consisting of SEQ ID NOs: 25 and 26.

8. An isolated fragment comprising a nucleotide sequence selected from the group consisting of
   (a) SEQ ID NO: 21,
   (b) the full-length sequences encoding a polypeptide having a peptide sequence selected from the group consisting of SEQ ID NOs: 25 and 26, and
   (c) the full-length complementary sequences to the sequences set forth in (a) or (b).

9. The fragment according to claim 8, consisting of a nucleotide sequence selected from the group consisting of
   (a) SEQ ID NO: 21,
   (b) the full-length sequences encoding a polypeptide having a peptide sequence selected from the group consisting of SEQ ID NOs: 25 and 26, and
   (c) the full-length complementary sequences to the sequences set forth in (a) or (b).

10. An RNA molecule comprising a fragment according to claim 8.

11. A DNA molecule comprising a fragment according to claim 8.

12. A method for detecting a retrovirus associated with multiple sclerosis or rheumatoid arthritis, the method comprising:
   a) obtaining and preparing a biological sample from a patient suspected of being infected with multiple sclerosis- or rheumatoid arthritis-related retrovirus,
   b) denaturing the nucleic acids present in the sample,
   c) contacting the nucleic acids of b) with a probe comprising the isolated fragment according to claim 8, under conditions that allow specific binding between the probe and target nucleic acids, and
   d) detecting a hybridization complex between said probe and said target nucleic acids.

13. The method according to claim 12, further comprising amplifying the target nucleic acids with a primer having a sequence selected from the group consisting of the full-length sequences set forth in SEQ ID NOs: 18, 19, 20, 23, and 24.

* * * * *

SEQUENCE LISTING

```
<160> NUMBER OF SEQ ID NOS: 45

<210> SEQ ID NO 1
<211> LENGTH: 34
<212> TYPE: DNA
<213> ORGANISM: MSRV

<400> SEQUENCE: 1
gactcgctgc agatcgattt tttttttttt tttt                                   34

<210> SEQ ID NO 2
<211> LENGTH: 30
<212> TYPE: DNA
<213> ORGANISM: MSRV

<400> SEQUENCE: 2
gccatcaagc cacccaagaa ctcttaactt                                        30

<210> SEQ ID NO 3
<211> LENGTH: 30
<212> TYPE: DNA
<213> ORGANISM: MSRV

<400> SEQUENCE: 3
ccaatagcca gaccattata tacactaatt                                        30

<210> SEQ ID NO 4
<211> LENGTH: 310
<212> TYPE: DNA
<213> ORGANISM: MSRV

<400> SEQUENCE: 4
gcttatagaa ggacccctag tatggggtaa tcccctctgg gaaaccaagc cccagtactc      60
agcaggaaaa atagaatagg aaacctcaca aggacatact ttcctcccct ccagatggct     120
agccactgag gaaggaaaaa tactttcacc tgcagctaac caacagaaat tacttaaaac     180
ccttcaccaa accttccact taggcattga tagcacccat cagatggcca aattattatt     240
tactggacca ggccttttca aaactatcaa gaagatagtc aggggctgtg aagtgtgcca     300
aagaaataat                                                            310

<210> SEQ ID NO 5
<211> LENGTH: 103
<212> TYPE: PRT
<213> ORGANISM: MSRV
<220> FEATURE:
<221> NAME/KEY: misc_feature
<222> LOCATION: (26)..(26)
<223> OTHER INFORMATION: Xaa = any amino acid

<400> SEQUENCE: 5

Leu Ile Glu Gly Pro Leu Val Trp Gly Asn Pro Leu Trp Glu Thr Lys
1               5                   10                  15

Pro Gln Tyr Ser Ala Gly Lys Ile Glu Xaa Glu Thr Ser Gln Gly His
            20                  25                  30

Thr Phe Leu Pro Ser Arg Trp Leu Ala Thr Glu Glu Gly Lys Ile Leu
```

-continued

```
        35                  40                  45

Ser Pro Ala Ala Asn Gln Gln Lys Leu Leu Lys Thr Leu His Gln Thr
    50                  55                  60

Phe His Leu Gly Ile Asp Ser Thr His Gln Met Ala Lys Leu Leu Phe
65                  70                  75                  80

Thr Gly Pro Gly Leu Phe Lys Thr Ile Lys Lys Ile Val Arg Gly Cys
                85                  90                  95

Glu Val Cys Gln Arg Asn Asn
            100

<210> SEQ ID NO 6
<211> LENGTH: 635
<212> TYPE: DNA
<213> ORGANISM: MSRV

<400> SEQUENCE: 6
ccctgtatct ttaacctcct tgttaagttt gtctcttcca gaatcaaaac tgtaaaacta     60
caaattgttc ttcaaatgga gcaccagatg gagtccatga ctaagatcca ccgtggaccc    120
ctggaccggc ctgctagccc atgctccgat gttaatgaca ttgaaggcac ccctcccgag    180
gaaatctcaa ctgcacaacc cctactatgc cccaattcag cgggaagcag ttagagcggt    240
catcagccaa cctccccaac agcacttggg ttttcctgtt gagagggggg actgagagac    300
aggactagct ggatttccta ggccaacgaa gaatccctaa gcctagctgg gaaggtgact    360
gcatccacct ctaaacatgg ggcttgcaac ttagctcaca cccgaccaat cagagagctc    420
actaaaatgc taattaggca aaaataggag gtaaagaaat agccaatcat ctattgcctg    480
agagcacagc gggagggaca aggatcggga tataaaccca ggcattcgag ccggcaacgg    540
caaccccctt tgggtcccct ccctttgtat gggcgctctg ttttcactct atttcactct    600
attaaatctt gcaactgaaa aaaaaaaaaa aaaaa                               635

<210> SEQ ID NO 7
<211> LENGTH: 77
<212> TYPE: PRT
<213> ORGANISM: MSRV

<400> SEQUENCE: 7

Pro Cys Ile Phe Asn Leu Leu Val Lys Phe Val Ser Ser Arg Ile Lys
1               5                   10                  15

Thr Val Lys Leu Gln Ile Val Leu Gln Met Glu His Gln Met Glu Ser
            20                  25                  30

Met Thr Lys Ile His Arg Gly Pro Leu Asp Arg Pro Ala Ser Pro Cys
        35                  40                  45

Ser Asp Val Asn Asp Ile Glu Gly Thr Pro Pro Glu Glu Ile Ser Thr
    50                  55                  60

Ala Gln Pro Leu Leu Cys Pro Asn Ser Ala Gly Ser Ser
65                  70                  75

<210> SEQ ID NO 8
<211> LENGTH: 32
<212> TYPE: DNA
<213> ORGANISM: MSRV

<400> SEQUENCE: 8
tggggttcca tttgtaagac catctgtagc tt                                   32

<210> SEQ ID NO 9
<211> LENGTH: 1481
```

-continued

<212> TYPE: DNA
<213> ORGANISM: MSRV

<400> SEQUENCE: 9

```
atggccctcc cttatcatac ttttctcttt actgttctct taccccccttt cgctctcact      60
gcacccccctc catgctgctg tacaaccagt agctcccctt accaagagtt tctatgaaga     120
acgcggcttc ctggaaatat tgatgcccca tcatatagga gtttatctaa gggaaactcc     180
accttcactg cccacaccca tatgccccgc aactgctata actctgccac tctttgcatg     240
catgcaaata ctcattattg gacagggaaa atgattaatc ctagttgtcc tggaggactt     300
ggagccactg tctgttggac ttacttcacc cataccagta tgtctgatgg gggtggaatt     360
caaggtcagg caagagaaaa acaagtaaag gaagcaatct cccaactgac ccggggacat     420
agcaccccta gcccctacaa aggactagtt ctctcaaaac tacatgaaac cctccgtacc     480
catactcgcc tggtgagcct atttaatacc accctcactc ggctccatga ggtctcagcc     540
caaaacccta ctaactgttg gatgtgcctc cccctgcact tcaggccata catttcaatc     600
cctgttcctg aacaatggaa caacttcagc acagaaataa acaccacttc cgttttagta     660
ggacctcttg tttccaatct ggaaataacc catacctcaa acctcacctg tgtaaaattt     720
agcaatacta tagacacaac cagctcccaa tgcatcaggt gggtaacacc tcccacacga     780
atagtctgcc taccctcagg aatatttttt gtctgtggta cctcagccta tcattgtttg     840
aatggctctt cagaatctat gtgcttcctc tcattcttag tgccccctat gaccatctac     900
actgaacaag atttatacaa tcatgtcgta cctaagcccc acaacaaaag agtacccatt     960
cttccttttg ttatcagagc aggagtgcta ggcagactag gtactggcat tggcagtatc    1020
acaacctcta ctcagttcta ctacaaacta tctcaagaaa taaatggtga catggaacag    1080
gtcactgact ccctggtcac cttgcaagat caacttaact ccctagcagc agtagtcctt    1140
caaaatcgaa gagctttaga cttgctaacc gccaaaagag ggggaacctg tttatttttta   1200
ggagaagaac gctgttatta tgttaatcaa tccagaattg tcactgagaa agttaaagaa    1260
attcgagatc gaatacaatg tagagcagag gagcttcaaa acaccgaacg ctggggcctc    1320
ctcagccaat ggatgccctg ggttctcccc ttcttaggac ctctagcagc tctaatattg    1380
ttactcctct ttggaccctg tatctttaac ctccttgtta agtttgtctc ttccagaatt    1440
gaagctgtaa agctacagat ggtcttacaa atggaacccc a                        1481
```

<210> SEQ ID NO 10
<211> LENGTH: 493
<212> TYPE: PRT
<213> ORGANISM: MSRV
<220> FEATURE:
<221> NAME/KEY: misc_feature
<222> LOCATION: (39)..(39)
<223> OTHER INFORMATION: Xaa = any amino acid

<400> SEQUENCE: 10

```
Met Ala Leu Pro Tyr His Thr Phe Leu Phe Thr Val Leu Leu Pro Pro
1               5                   10                  15

Phe Ala Leu Thr Ala Pro Pro Pro Cys Cys Cys Thr Thr Ser Ser Ser
            20                  25                  30

Pro Tyr Gln Glu Phe Leu Xaa Arg Thr Arg Leu Pro Gly Asn Ile Asp
        35                  40                  45

Ala Pro Ser Tyr Arg Ser Leu Ser Lys Gly Asn Ser Thr Phe Thr Ala
    50                  55                  60

His Thr His Met Pro Arg Asn Cys Tyr Asn Ser Ala Thr Leu Cys Met
```

```
                65                  70                  75                  80
            His Ala Asn Thr His Tyr Trp Thr Gly Lys Met Ile Asn Pro Ser Cys
                                85                  90                  95

Pro Gly Gly Leu Gly Ala Thr Val Cys Trp Thr Tyr Phe Thr His Thr
                            100                 105                 110

Ser Met Ser Asp Gly Gly Ile Gln Gly Gln Ala Arg Glu Lys Gln
                        115                 120                 125

Val Lys Glu Ala Ile Ser Gln Leu Thr Arg Gly His Ser Thr Pro Ser
                130                 135                 140

Pro Tyr Lys Gly Leu Val Leu Ser Lys Leu His Glu Thr Leu Arg Thr
            145                 150                 155                 160

His Thr Arg Leu Val Ser Leu Phe Asn Thr Thr Leu Thr Arg Leu His
                            165                 170                 175

Glu Val Ser Ala Gln Asn Pro Thr Asn Cys Trp Met Cys Leu Pro Leu
                        180                 185                 190

His Phe Arg Pro Tyr Ile Ser Ile Pro Val Pro Glu Gln Trp Asn Asn
                    195                 200                 205

Phe Ser Thr Glu Ile Asn Thr Thr Ser Val Leu Val Gly Pro Leu Val
                210                 215                 220

Ser Asn Leu Glu Ile Thr His Thr Ser Asn Leu Thr Cys Val Lys Phe
            225                 230                 235                 240

Ser Asn Thr Ile Asp Thr Thr Ser Ser Gln Cys Ile Arg Trp Val Thr
                            245                 250                 255

Pro Pro Thr Arg Ile Val Cys Leu Pro Ser Gly Ile Phe Phe Val Cys
                        260                 265                 270

Gly Thr Ser Ala Tyr His Cys Leu Asn Gly Ser Ser Glu Ser Met Cys
                    275                 280                 285

Phe Leu Ser Phe Leu Val Pro Pro Met Thr Ile Tyr Thr Glu Gln Asp
                290                 295                 300

Leu Tyr Asn His Val Val Pro Lys Pro His Asn Lys Arg Val Pro Ile
            305                 310                 315                 320

Leu Pro Phe Val Ile Arg Ala Gly Val Leu Gly Arg Leu Gly Thr Gly
                            325                 330                 335

Ile Gly Ser Ile Thr Thr Ser Thr Gln Phe Tyr Tyr Lys Leu Ser Gln
                        340                 345                 350

Glu Ile Asn Gly Asp Met Glu Gln Val Thr Asp Ser Leu Val Thr Leu
                    355                 360                 365

Gln Asp Gln Leu Asn Ser Leu Ala Ala Val Val Leu Gln Asn Arg Arg
                370                 375                 380

Ala Leu Asp Leu Leu Thr Ala Lys Arg Gly Gly Thr Cys Leu Phe Leu
            385                 390                 395                 400

Gly Glu Glu Arg Cys Tyr Tyr Val Asn Gln Ser Arg Ile Val Thr Glu
                            405                 410                 415

Lys Val Lys Glu Ile Arg Asp Arg Ile Gln Cys Arg Ala Glu Glu Leu
                        420                 425                 430

Gln Asn Thr Glu Arg Trp Gly Leu Leu Ser Gln Trp Met Pro Trp Val
                    435                 440                 445

Leu Pro Phe Leu Gly Pro Leu Ala Ala Leu Ile Leu Leu Leu Leu Phe
                450                 455                 460

Gly Pro Cys Ile Phe Asn Leu Leu Val Lys Phe Val Ser Ser Arg Ile
            465                 470                 475                 480

Glu Ala Val Lys Leu Gln Met Val Leu Gln Met Glu Pro
                            485                 490
```

```
<210> SEQ ID NO 11
<211> LENGTH: 32
<212> TYPE: DNA
<213> ORGANISM: MSRV

<400> SEQUENCE: 11
tcaaaatcga agagctttag acttgctaac cg                                        32

<210> SEQ ID NO 12
<211> LENGTH: 1329
<212> TYPE: DNA
<213> ORGANISM: MSRV
<220> FEATURE:
<221> NAME/KEY: misc_feature
<222> LOCATION: (594)..(594)
<223> OTHER INFORMATION: n = a, g, c or t/u
<220> FEATURE:
<221> NAME/KEY: misc_feature
<222> LOCATION: (602)..(602)
<223> OTHER INFORMATION: n = a, g, c or t/u
<220> FEATURE:
<221> NAME/KEY: misc_feature
<222> LOCATION: (1232)..(1232)
<223> OTHER INFORMATION: n = a, g, c or t/u

<400> SEQUENCE: 12
tcaaaatcga agagctttag acttgctaac cgccaaaaga gggggaacct gtttattttt        60
aggggaagaa tgctgttagt atgttaatca atctggaatc attactgaga aagttaaaga       120
aatttgagat cgaatataat gtagagcaga ggaccttcaa acactgcac  cctggggcct       180 cctcagccaa tggatgccct ggactctccc cttcttagga cctctagcag ctataatatt       240
tttactcctc tttggaccct gtatcttcaa cttccttgtt aagtttgtct cttccagaat       300
tgaagctgta aagctacaaa tagttcttca aatggaaccc cagatgcagt ccatgactaa       360
aatctaccgt ggacccctgg accggcctgc tagactatgc tctgatgtta atgacattga       420
agtcacccct cccgaggaaa tctcaactgc acaaccccta ctacactcca attcagtagg       480
aagcagttag agcagttgtc agccaacctc cccaacagta cttgggtttt cctgttgaga       540
gggtggactg agagacagga ctagctggat ttcctaggct gactaagaat cccnaagcct       600
anctgggaag gtgaccgcat ccatctttaa acatggggct tgcaacttag ctcacacccg       660
accaatcaga gagctcacta aaatgctaat caggcaaaaa caggaggtaa agcaatagcc       720
aatcatctat tgcctgagag cacagcggga aggacaagga ttgggatata aactcaggca       780
ttcaagccag caacagcaac ccccctttggg tccctccca ttgtatggga gctctgtttt       840
cactctattt cactctatta aatcatgcaa ctgcactctt ctggtccgtg tttttatgg        900 ctcaagctga gcttttgttc gccatccacc actgctgttt gccaccgtca cagacccgct       960
gctgacttcc atcccttttgg atccagcaga gtgtccactg tgctcctgat ccagcgaggt      1020
acccattgcc actcccgatc aggctaaagg cttgccattg ttcctgcatg gctaagtgcc      1080
tgggtttgtc ctaatagaac tgaacactgg tcactgggtt ccatggttct cttccatgac      1140
ccacggcttc taatagagct ataacactca ccgcatggcc caagattcca ttccttggta      1200
tctgtgaggc caagaaccc  aggtcagaga angtgaggct tgccaccatt tgggaagtgg      1260
cccactgcca ttttggtagc ggcccaccac catcttggga gctgtgggag caaggatccc      1320
ccagtaaca                                                                1329

<210> SEQ ID NO 13
<211> LENGTH: 162
<212> TYPE: PRT
```

```
<213> ORGANISM: MSRV
<220> FEATURE:
<221> NAME/KEY: misc_feature
<222> LOCATION: (26)..(26)
<223> OTHER INFORMATION: Xaa = any amino acid
<220> FEATURE:
<221> NAME/KEY: misc_feature
<222> LOCATION: (42)..(42)
<223> OTHER INFORMATION: Xaa = any amino acid
<220> FEATURE:
<221> NAME/KEY: misc_feature
<222> LOCATION: (46)..(46)
<223> OTHER INFORMATION: Xaa = any amino acid

<400> SEQUENCE: 13

Gln Asn Arg Arg Ala Leu Asp Leu Leu Thr Ala Lys Arg Gly Gly Thr
1               5                   10                  15

Cys Leu Phe Leu Gly Glu Glu Cys Cys Xaa Tyr Val Asn Gln Ser Gly
            20                  25                  30

Ile Ile Thr Glu Lys Val Lys Glu Ile Xaa Asp Arg Ile Xaa Cys Arg
        35                  40                  45

Ala Glu Asp Leu Gln Asn Thr Ala Pro Trp Gly Leu Leu Ser Gln Trp
    50                  55                  60

Met Pro Trp Thr Leu Pro Phe Leu Gly Pro Leu Ala Ala Ile Ile Phe
65                  70                  75                  80

Leu Leu Leu Phe Gly Pro Cys Ile Phe Asn Phe Leu Val Lys Phe Val
                85                  90                  95

Ser Ser Arg Ile Glu Ala Val Lys Leu Gln Ile Val Leu Gln Met Glu
            100                 105                 110

Pro Gln Met Gln Ser Met Thr Lys Ile Tyr Arg Gly Pro Leu Asp Arg
        115                 120                 125

Pro Ala Arg Leu Cys Ser Asp Val Asn Asp Ile Glu Val Thr Pro Pro
    130                 135                 140

Glu Glu Ile Ser Thr Ala Gln Pro Leu Leu His Ser Asn Ser Val Gly
145                 150                 155                 160

Ser Ser

<210> SEQ ID NO 14
<211> LENGTH: 21
<212> TYPE: DNA
<213> ORGANISM: MSRV

<400> SEQUENCE: 14
ggcattgata gcacccatca g                                           21

<210> SEQ ID NO 15
<211> LENGTH: 21
<212> TYPE: DNA
<213> ORGANISM: MSRV

<400> SEQUENCE: 15
catgtcacca gggtggaata g                                           21

<210> SEQ ID NO 16
<211> LENGTH: 758
<212> TYPE: DNA
<213> ORGANISM: MSRV

<400> SEQUENCE: 16
ggcattgata gcacccatca gatggccaaa tcattattta ctggaccagg ccttttcaaa    60
actatcaagc agatagggcc cgtgaagcat gccaaagaaa taatcccctg ccttatcgcc   120
```

-continued

| | |
|---|---|
| atgttccttc aggagaacaa agaacaggcc attacccagg ggaagactgg caactagatt | 180 |
| ttacccacat ggccaaatgt cagggatttc agcatctact agtctgggca gatactttca | 240 |
| ctggttgggt ggagtcttct ccttgtagga cagaaaagac ccagaggta ataaaggcac | 300 |
| taatgaaata attcccagat ttggacttcc cccaggatta cagggtgaca atggcccgc | 360 |
| tttcaaggct gcagtaaccc agggagtatc ccaggtgtta ggcatacaat atcacttaca | 420 |
| ctgtgcctgg aggccacaat cctccagaaa agtcaagaaa atgaatgaaa cactcaaaga | 480 |
| tctaaaaaag ctaacccaag aaacccacat tgcatgacct gttctgttgc ctataacctt | 540 |
| actaagaatc cataactatc ccccaaaaag caggacttag cccatacgag atgctatatg | 600 |
| gatggccttt cctaaccaat gaccttgtgc ttgactgaga aatggccaac ttagttgcag | 660 |
| acatcacctc cttagccaaa tatcaacaag ttcttaaaac atcacaggga acctgtcccc | 720 |
| gagaggaggg aaaggaacta ttccaccctg gtgacatg | 758 |

<210> SEQ ID NO 17
<211> LENGTH: 25
<212> TYPE: DNA
<213> ORGANISM: MSRV

<400> SEQUENCE: 17

| | |
|---|---|
| cggacatcca aagtgatggg aaacg | 25 |

<210> SEQ ID NO 18
<211> LENGTH: 26
<212> TYPE: DNA
<213> ORGANISM: MSRV

<400> SEQUENCE: 18

| | |
|---|---|
| ggacaggaaa gtaagactga gaaggc | 26 |

<210> SEQ ID NO 19
<211> LENGTH: 26
<212> TYPE: DNA
<213> ORGANISM: MSRV

<400> SEQUENCE: 19

| | |
|---|---|
| cctagaacgt attctggaga attggg | 26 |

<210> SEQ ID NO 20
<211> LENGTH: 26
<212> TYPE: DNA
<213> ORGANISM: MSRV

<400> SEQUENCE: 20

| | |
|---|---|
| tggctctcaa tggtcaaaca tacccg | 26 |

<210> SEQ ID NO 21
<211> LENGTH: 1511
<212> TYPE: DNA
<213> ORGANISM: MSRV

<400> SEQUENCE: 21

| | |
|---|---|
| cctagaacgt attctggaga attgggacca atgtgacact cagacgctaa gaaagaaacg | 60 |
| atttatattc ttctgcagta ccgcctggcc acaatatcct cttcaaggga gagaaacctg | 120 |
| gcttcctgag ggaagtataa attataacat catcttacag ctagacctct tctgtagaaa | 180 |
| ggagggcaaa tggagtgaag tgccatatgt gcaaactttc ttttcattaa gagacaactc | 240 |
| acaattatgt aaaaagtgtg gtttatgccc tacaggaagc cctcagagtc cacctcccta | 300 |

```
cccccagcgtc ccctccccga ctccttcctc aactaataag gaccccctt taacccaaac     360
ggtccaaaag gagatagaca aaggggtaaa caatgaacca aagagtgcca atattccccg     420
attatgcccc ctccaagcag tgagaggagg agaattcggc ccagccagag tgcctgtacc     480
tttttctctc tcagacttaa agcaaattaa aatagaccta ggtaaattct cagataaccc     540
tgacggctat attgatgttt tacaagggtt aggacaatcc tttgatctga catggagaga     600
tataatgtta ctactaaatc agacactaac cccaaatgag agaagtgccg ctgtaactgc     660
agcccgagag tttggcgatc tttggtatct cagtcaggcc aacaatagga tgacaacaga     720
ggaaagaaca actcccacag gccagcaggc agttcccagt gtagaccctc attgggacac     780
agaatcagaa catggagatt ggtgccacaa acatttgcta acttgcgtgc tagaaggact     840
gaggaaaact aggaagaagc ctatgaatta ctcaatgatg tccactataa cacagggaaa     900
ggaagaaaat cttactgctt ttctggacag actaagggag gcattgagga agcatacctc     960
cctgtcacct gactctattg aaggccaact aatcttaaag gataagttta tcactcagtc    1020
agctgcagac attagaaaaa acttcaaaag tctgccttag gcccggagca gaacttagaa    1080
accctatttta acttggcatc ctcagttttt tataatagag atcaggagga gcaggcgaaa    1140
cgggacaaac gggataaaaa aaaagggggg ggtccactac tttagtcatg gccctcaggc    1200
aagcagactt tggaggctct gcaaaaggga aaagctgggc aaatcaaatg cctaataggg    1260
ctggcttcca gtgcggtcta caaggacact ttaaaaaaga ttatccaagt agaaataagc    1320
cgccccttg tccatgcccc ttacgtcaag ggaatcactg gaaggccac tgccccaggg    1380
gatgaagata ctctgagtca gaagccatta accagatgat ccagcagcag gactgagggt    1440
gcccggggcg agcgccagcc catgccatca ccctcacaga gccccgggta tgtttgacca    1500
ttgagagcca a                                                         1511
```

<210> SEQ ID NO 22
<211> LENGTH: 352
<212> TYPE: PRT
<213> ORGANISM: MSRV

<400> SEQUENCE: 22

```
Leu Glu Arg Ile Leu Glu Asn Trp Asp Gln Cys Asp Thr Gln Thr Leu
1               5                   10                  15

Arg Lys Lys Arg Phe Ile Phe Phe Cys Ser Thr Ala Trp Pro Gln Tyr
            20                  25                  30

Pro Leu Gln Gly Arg Glu Thr Trp Leu Pro Glu Gly Ser Ile Asn Tyr
        35                  40                  45

Asn Ile Ile Leu Gln Leu Asp Leu Phe Cys Arg Lys Glu Gly Lys Trp
    50                  55                  60

Ser Glu Val Pro Tyr Val Gln Thr Phe Phe Ser Leu Arg Asp Asn Ser
65                  70                  75                  80

Gln Leu Cys Lys Lys Cys Gly Leu Cys Pro Thr Gly Ser Pro Gln Ser
                85                  90                  95

Pro Pro Pro Tyr Pro Ser Val Pro Ser Pro Thr Pro Ser Ser Thr Asn
            100                 105                 110

Lys Asp Pro Pro Leu Thr Gln Thr Val Gln Lys Glu Ile Asp Lys Gly
        115                 120                 125

Val Asn Asn Glu Pro Lys Ser Ala Asn Ile Pro Arg Leu Cys Pro Leu
    130                 135                 140

Gln Ala Val Arg Gly Gly Glu Phe Gly Pro Ala Arg Val Pro Val Pro
145                 150                 155                 160
```

-continued

```
Phe Ser Leu Ser Asp Leu Lys Gln Ile Lys Ile Asp Leu Gly Lys Phe
                165                 170                 175

Ser Asp Asn Pro Asp Gly Tyr Ile Asp Val Leu Gln Gly Leu Gly Gln
            180                 185                 190

Ser Phe Asp Leu Thr Trp Arg Asp Ile Met Leu Leu Leu Asn Gln Thr
        195                 200                 205

Leu Thr Pro Asn Glu Arg Ser Ala Ala Val Thr Ala Ala Arg Glu Phe
    210                 215                 220

Gly Asp Leu Trp Tyr Leu Ser Gln Ala Asn Asn Arg Met Thr Thr Glu
225                 230                 235                 240

Glu Arg Thr Thr Pro Thr Gly Gln Gln Ala Val Pro Ser Val Asp Pro
                245                 250                 255

His Trp Asp Thr Glu Ser Glu His Gly Asp Trp Cys His Lys His Leu
            260                 265                 270

Leu Thr Cys Val Leu Glu Gly Leu Arg Lys Thr Arg Lys Lys Pro Met
        275                 280                 285

Asn Tyr Ser Met Met Ser Thr Ile Thr Gln Gly Lys Glu Glu Asn Leu
    290                 295                 300

Thr Ala Phe Leu Asp Arg Leu Arg Glu Ala Leu Arg Lys His Thr Ser
305                 310                 315                 320

Leu Ser Pro Asp Ser Ile Glu Gly Gln Leu Ile Leu Lys Asp Lys Phe
                325                 330                 335

Ile Thr Gln Ser Ala Ala Asp Ile Arg Lys Asn Phe Lys Ser Leu Pro
            340                 345                 350

<210> SEQ ID NO 23
<211> LENGTH: 30
<212> TYPE: DNA
<213> ORGANISM: MSRV

<400> SEQUENCE: 23
tgctggaatt cgggatccta gaacgtattc                                      30

<210> SEQ ID NO 24
<211> LENGTH: 30
<212> TYPE: DNA
<213> ORGANISM: MSRV

<400> SEQUENCE: 24
agttctgctc cgaagcttag gcagactttt                                      30

<210> SEQ ID NO 25
<211> LENGTH: 398
<212> TYPE: PRT
<213> ORGANISM: MSRV

<400> SEQUENCE: 25

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Ile Leu Glu Arg Ile Leu Glu Asn Trp Asp Gln Cys Asp Thr Gln Thr
        35                  40                  45

Leu Arg Lys Lys Arg Phe Ile Phe Phe Cys Ser Thr Ala Trp Pro Gln
    50                  55                  60

Tyr Pro Leu Gln Gly Arg Glu Thr Trp Leu Pro Glu Gly Ser Ile Asn
65                  70                  75                  80

Tyr Asn Ile Ile Leu Gln Leu Asp Leu Phe Cys Arg Lys Glu Gly Lys
```

```
                85                  90                  95

Trp Ser Glu Val Pro Tyr Val Gln Thr Phe Phe Ser Leu Arg Asp Asn
            100                 105                 110

Ser Gln Leu Cys Lys Lys Cys Gly Leu Cys Pro Thr Gly Ser Pro Gln
        115                 120                 125

Ser Pro Pro Pro Tyr Pro Ser Val Pro Ser Pro Thr Pro Ser Ser Thr
    130                 135                 140

Asn Lys Asp Pro Pro Leu Thr Gln Thr Val Gln Lys Glu Ile Asp Lys
145                 150                 155                 160

Gly Val Asn Asn Glu Pro Lys Ser Ala Asn Ile Pro Arg Leu Cys Pro
                165                 170                 175

Leu Gln Ala Val Arg Gly Gly Glu Phe Gly Pro Ala Arg Val Pro Val
            180                 185                 190

Pro Phe Ser Leu Ser Asp Leu Lys Gln Ile Lys Ile Asp Leu Gly Lys
        195                 200                 205

Phe Ser Asp Asn Pro Asp Gly Tyr Ile Asp Val Leu Gln Gly Leu Gly
    210                 215                 220

Gln Ser Phe Asp Leu Thr Trp Arg Asp Ile Met Leu Leu Leu Asn Gln
225                 230                 235                 240

Thr Leu Thr Pro Asn Glu Arg Ser Ala Ala Val Thr Ala Ala Arg Glu
                245                 250                 255

Phe Gly Asp Leu Trp Tyr Leu Ser Gln Ala Asn Asn Arg Met Thr Thr
            260                 265                 270

Glu Glu Arg Thr Thr Pro Thr Gly Gln Gln Ala Val Pro Ser Val Asp
        275                 280                 285

Pro His Trp Asp Thr Glu Ser Glu His Gly Asp Trp Cys His Lys His
    290                 295                 300

Leu Leu Thr Cys Val Leu Glu Gly Leu Arg Lys Thr Arg Lys Lys Pro
305                 310                 315                 320

Met Asn Tyr Ser Met Met Ser Thr Ile Thr Gln Gly Lys Glu Glu Asn
                325                 330                 335

Leu Thr Ala Phe Leu Asp Arg Leu Arg Glu Ala Leu Arg Lys His Thr
            340                 345                 350

Ser Leu Ser Pro Asp Ser Ile Glu Gly Gln Leu Ile Leu Lys Asp Lys
        355                 360                 365

Phe Ile Thr Gln Ser Ala Ala Asp Ile Arg Lys Asn Phe Lys Ser Leu
    370                 375                 380

Pro Lys Leu Ala Ala Ala Leu Glu His His His His His His
385                 390                 395

<210> SEQ ID NO 26
<211> LENGTH: 378
<212> TYPE: PRT
<213> ORGANISM: MSRV

<400> SEQUENCE: 26

Met Ala Ser Met Thr Gly Gly Gln Gln Met Gly Arg Ile Leu Glu Arg
1               5                   10                  15

Ile Leu Glu Asn Trp Asp Gln Cys Asp Thr Gln Thr Leu Arg Lys Lys
            20                  25                  30

Arg Phe Ile Phe Phe Cys Ser Thr Ala Trp Pro Gln Tyr Pro Leu Gln
        35                  40                  45

Gly Arg Glu Thr Trp Leu Pro Glu Gly Ser Ile Asn Tyr Asn Ile Ile
    50                  55                  60

Leu Gln Leu Asp Leu Phe Cys Arg Lys Glu Gly Lys Trp Ser Glu Val
```

```
                65                  70                  75                  80
        Pro Tyr Val Gln Thr Phe Phe Ser Leu Arg Asp Asn Ser Gln Leu Cys
                        85                  90                  95
        Lys Lys Cys Gly Leu Cys Pro Thr Gly Ser Pro Gln Ser Pro Pro Pro
                    100                 105                 110
        Tyr Pro Ser Val Pro Ser Pro Thr Pro Ser Ser Thr Asn Lys Asp Pro
                    115                 120                 125
        Pro Leu Thr Gln Thr Val Gln Lys Glu Ile Asp Lys Gly Val Asn Asn
                130                 135                 140
        Glu Pro Lys Ser Ala Asn Ile Pro Arg Leu Cys Pro Leu Gln Ala Val
        145                 150                 155                 160
        Arg Gly Gly Glu Phe Gly Pro Ala Arg Val Pro Val Pro Phe Ser Leu
                        165                 170                 175
        Ser Asp Leu Lys Gln Ile Lys Ile Asp Leu Gly Lys Phe Ser Asp Asn
                    180                 185                 190
        Pro Asp Gly Tyr Ile Asp Val Leu Gln Gly Leu Gly Gln Ser Phe Asp
                    195                 200                 205
        Leu Thr Trp Arg Asp Ile Met Leu Leu Leu Asn Gln Thr Leu Thr Pro
                210                 215                 220
        Asn Glu Arg Ser Ala Ala Val Thr Ala Ala Arg Glu Phe Gly Asp Leu
        225                 230                 235                 240
        Trp Tyr Leu Ser Gln Ala Asn Asn Arg Met Thr Thr Glu Glu Arg Thr
                        245                 250                 255
        Thr Pro Thr Gly Gln Gln Ala Val Pro Ser Val Asp Pro His Trp Asp
                    260                 265                 270
        Thr Glu Ser Glu His Gly Asp Trp Cys His Lys His Leu Leu Thr Cys
                    275                 280                 285
        Val Leu Glu Gly Leu Arg Lys Thr Arg Lys Lys Pro Met Asn Tyr Ser
                290                 295                 300
        Met Met Ser Thr Ile Thr Gln Gly Lys Glu Asn Leu Thr Ala Phe
        305                 310                 315                 320
        Leu Asp Arg Leu Arg Glu Ala Leu Arg Lys His Thr Ser Leu Ser Pro
                        325                 330                 335
        Asp Ser Ile Glu Gly Gln Leu Ile Leu Lys Asp Lys Phe Ile Thr Gln
                    340                 345                 350
        Ser Ala Ala Asp Ile Arg Lys Asn Phe Lys Ser Leu Pro Lys Leu Ala
                    355                 360                 365
        Ala Ala Leu Glu His His His His His His
                370                 375

<210> SEQ ID NO 27
<211> LENGTH: 25
<212> TYPE: DNA
<213> ORGANISM: MSRV

<400> SEQUENCE: 27
cttggagggt gcataaccag ggaat                                    25

<210> SEQ ID NO 28
<211> LENGTH: 20
<212> TYPE: DNA
<213> ORGANISM: MSRV

<400> SEQUENCE: 28
tgtccgctgt gctcctgatc                                          20
```

```
<210> SEQ ID NO 29
<211> LENGTH: 25
<212> TYPE: DNA
<213> ORGANISM: MSRV

<400> SEQUENCE: 29
ctatgtcctt ttggactgtt tgggt                                           25

<210> SEQ ID NO 30
<211> LENGTH: 764
<212> TYPE: DNA
<213> ORGANISM: MSRV

<400> SEQUENCE: 30
tgtccgctgt gctcctgatc cagcacaggc gcccattgcc tctcccaatt gggctaaagg     60
cttgccattg ttcctgcaca gctaagtgcc tgggttcatc ctaatcgagc tgaacactag    120
tcactgggtt ccacggttct cttccatgac ccatggcttc taatagagct ataacactca    180
ctgcatggtc caagattcca ttccttggaa tccgtgagac caagaacccc aggtcagaga    240
acacaaggct tgccaccatg ttggaagcag cccaccacca ttttggaagc agcccgccac    300
tatcttggga gctctgggag caaggacccc aggtaacaat tggtgaccca cgaagggacc    360
tgaatccgca accatgaagg gatctccaaa gcaattggaa atgttcctcc caaggcaaaa    420
atgcccctaa gatgtattct ggagaattgg accaatttg  accctcagac agtaagaaaa    480
aaatgactta tattcttctg cagtaccgcc ctggccacga tatcctcttc aagggggaga    540
aacctggcct cctgagggaa gtataaatta taacaccatc ttacagctag acctgttttg    600
tagaaaagga ggcaaatgga gtgaagtgcc atatttacaa actttctttt cattaaaaga    660
caactcgcaa ttatgttaac agtgtgattt gtgttcctac acggaagccc tcagattcta    720
ctccccaccc ccggcatctc ccctgaatcc ctccccaact tatt                     764

<210> SEQ ID NO 31
<211> LENGTH: 800
<212> TYPE: DNA
<213> ORGANISM: MSRV

<400> SEQUENCE: 31
tgtccgctgt gctcctgatc cagcacaggc gcccattgcc tctcccaatt gggctaaagg     60
cttgccattg ttcctgcaca gctaagtgcc tgggttcatc ctaatcgagc tgaacactag    120
tcactgggtt ccacggttct cttccatgac ccatggcttc taatagagct ataacactca    180
ctgcatggtc caagattcca ttccttggaa tccgtgagac caagaacccc aggtcagaga    240
acacaaggct tgccaccatg ttggaagcag cccaccacca ttttggaagc ggcccgccac    300
tatcttggga gctctgggag caaggacccc aggtaacaa  tttggtgacc acgaagggac    360
ctgaatccgc aaccatgaag ggatctccaa agcaattgga atgttcctc  ccaaggcaaa    420
aatgccccta agatgtattc tggagaattg gaccaatct  gaccctcaga cagtaagaaa    480
aaaaatgact tatattcttc tgcagtaccg cctggccacg gatatcctct tcaaggggga    540
gaaacctggc tcctgaggg  aagtataaat tataaccaca tcttcagct  agacctgttt    600
tgtagaaaag gaggcaaatg gagtgaagtg ccatatttac aaactttctt ttcattaaaa    660
gacaactcgc aattatgtaa acagtgtgat ttgtgtccta caggaagccc tcagatctac    720
ctccctaccc cggcatctcc ctgactcctt ccccaactaa taaggaccca cttcagccca    780
aacagtccaa aaggacatag                                                800
```

```
<210> SEQ ID NO 32
<211> LENGTH: 65
<212> TYPE: PRT
<213> ORGANISM: MSRV

<400> SEQUENCE: 32

Pro Met Ala Ser Asn Arg Ala Ile Thr Leu Thr Ala Trp Ser Lys Ile
1               5                   10                  15

Pro Phe Leu Gly Ile Arg Glu Thr Lys Asn Pro Arg Ser Glu Asn Thr
            20                  25                  30

Arg Leu Ala Thr Met Leu Glu Ala Ala His His Phe Gly Ser Ser
        35                  40                  45

Pro Pro Leu Ser Trp Glu Leu Trp Glu Gln Gly Pro Gln Val Thr Ile
    50                  55                  60

Trp
65

<210> SEQ ID NO 33
<211> LENGTH: 26
<212> TYPE: DNA
<213> ORGANISM: MSRV

<400> SEQUENCE: 33
tcatgcaact gcactcttct ggtccg                                                26

<210> SEQ ID NO 34
<211> LENGTH: 28
<212> TYPE: DNA
<213> ORGANISM: MSRV

<400> SEQUENCE: 34
tcttgcacta acctccactg tccgttgg                                              28

<210> SEQ ID NO 35
<211> LENGTH: 28
<212> TYPE: DNA
<213> ORGANISM: MSRV

<400> SEQUENCE: 35
atcccccagt aacaatttgg tgaccacg                                              28

<210> SEQ ID NO 36
<211> LENGTH: 31
<212> TYPE: DNA
<213> ORGANISM: MSRV

<400> SEQUENCE: 36
tcgggtctaa gagggtactt cctttggtag g                                          31

<210> SEQ ID NO 37
<211> LENGTH: 25
<212> TYPE: DNA
<213> ORGANISM: MSRV

<400> SEQUENCE: 37
ttacgcaggt ctcagggatg agctt                                                 25

<210> SEQ ID NO 38
<211> LENGTH: 33
<212> TYPE: DNA
<213> ORGANISM: MSRV

<400> SEQUENCE: 38
```

```
cggcagtagc agtcttagta tctgaagcag tta                             33
```

<210> SEQ ID NO 39
<211> LENGTH: 28
<212> TYPE: DNA
<213> ORGANISM: MSRV

<400> SEQUENCE: 39

```
ggtacggagg gtttcatgta gttttgag                                   28
```

<210> SEQ ID NO 40
<211> LENGTH: 1247
<212> TYPE: DNA
<213> ORGANISM: MSRV
<220> FEATURE:
<221> NAME/KEY: misc_feature
<222> LOCATION: (1240)..(1240)
<223> OTHER INFORMATION: n = a, g, c or t/u
<220> FEATURE:
<221> NAME/KEY: misc_feature
<222> LOCATION: (1246)..(1246)
<223> OTHER INFORMATION: n = a, g, c or t/u

<400> SEQUENCE: 40

```
atgggcagca gccatcatca tcatcatcac agcagcggcc tggtgccgcg cggcagccat   60
atggctagca tgactggtgg acagcaaatg ggtcggatcc tagaacgtat tctggagaat  120
tgggaccaat gtgacactca gacgctaaga aagaaacgat ttatattctt ctgcagtacc  180
gcctggccac aatatcctct tcaagggaga gaaacctggc ttcctgaggg aagtataaat  240
tataacatca tcttacagct agacctcttc tgtagaaagg agggcaaatg gagtgaagtg  300
ccatatgtgc aaactttctt ttcattaaga gacaactcac aattatgtaa aaagtgtggt  360
ttatgcccta caggaagccc tcagagtcca cctccctacc ccagcgtccc ctccccgact  420
ccttcctcaa ctaataagga ccccccttta acccaaacgg tccaaaagga gatagacaaa  480
ggggtaaaca atgaaccaaa gagtgccaat attccccgat tatgccccct ccaagcagtg  540
agaggaggag aattcggccc agccagagtg cctgtacctt tttctctctc agacttaaag  600
caaattaaaa tagacctagg taaattctca gataaccctg acggctatat tgatgtttta  660
caagggttag acaatccctt tgatctgaca tggagagata taatgttact actaaatcag  720
acactaaccc caaatgagag aagtgccgct gtaactgcag cccgagagtt tggcgatctt  780
tggtatctca gtcaggccaa caataggatg acaacagagg aaagaacaac tcccacaggc  840
cagcaggcag ttcccagtgt agaccctcat tgggacacag aatcagaaca tggagattgg  900
tgccacaaac atttgctaac ttgcgtgcta gaaggactga ggaaaactag gaagaagcct  960
atgaattact caatgatgtc cactataaca cagggaaagg aagaaaatct tactgctttt 1020
ctggacagac taagggaggc attgaggaag catacctccc tgtcacctga ctctattgaa 1080
ggccaactaa tcttaaagga taagtttatc actcagtcag ctgcagacat tagaaaaaac 1140
ttcaaaagtc tgcctaagct tgcggccgca ctcgagcacc accaccacca ccactgagat 1200
ccggctgcta acaaagcccg aaaggaagct gagttgggtn gtggcna            1247
```

<210> SEQ ID NO 41
<211> LENGTH: 1186
<212> TYPE: DNA
<213> ORGANISM: MSRV

<400> SEQUENCE: 41

```
atggctagca tgactggtgg acagcaaatg ggtcggatcc tagaacgtat tctggagaat   60
```

-continued

```
tgggaccaat gtgacactca gacgctaaga aagaaacgat ttatattctt ctgcagtacc    120
gcctggccac aatatcctct tcaagggaga gaaacctggc ttcctgaggg aagtataaat    180
tataacatca tcttacagct agacctcttc tgtagaaagg agggcaaatg gagtgaagtg    240
ccatatgtgc aaactttctt ttcattaaga gacaactcac aattatgtaa aaagtgtggt    300
ttatgcccta caggaagccc tcagagtcca cctccctacc ccagcgtccc ctccccgact    360
ccttcctcaa ctaataagga cccccccttta acccaaacgg tccaaaagga gatagacaaa    420
ggggtaaaca atgaaccaaa gagtgccaat attccccgat tatgcccct ccaagcagtg    480 agaggaggag aattcggccc agccagagtg cctgtacctt tttctctctc agacttaaag    540
caaattaaaa tagacctagg taaattctca gataaccctg acggctatat tgatgtttta    600
caagggttag gacaatcctt tgatctgaca tggagagata taatgttact actaaatcag    660
acactaaccc caaatgagag aagtgccgct gtaactgcag cccgagagtt tggcgatctt    720
tggtatctca gtcaggccaa caataggatg acaacagagg aaagaacaac tcccacaggc    780
cagcaggcag ttcccagtgt agaccctcat tgggacacag aatcagaaca tggagattgg    840
tgccacaaac atttgctaac ttgcgtgcta gaaggactga ggaaaactag gaagaagcct    900
atgaattact caatgatgtc cactataaca cagggaaagg aagaaaatct tactgctttt    960
ctggacagac taagggaggc attgaggaag catacctccc tgtcacctga ctctattgaa   1020
ggccaactaa tcttaaagga taagtttatc actcagtcag ctgcagacat tagaaaaaac   1080
ttcaaaagtc tgcctaagct tgcggccgca ctcgagcacc accaccacca ccactgagat   1140
ccggctgcta acaaagcccg aaaggaagct gagttggctg gtggca                  1186
```

<210> SEQ ID NO 42
<211> LENGTH: 2030
<212> TYPE: DNA
<213> ORGANISM: MSRV

<400> SEQUENCE: 42

```
atggccctcc cttatcatac ttttctcttt actgttctct taccccccttt cgctctcact     60 gcacccccctc catgctgctg tacaaccagt agctcccctt accaagagtt tctatgaaga    120
acgcggcttc ctggaaatat tgatgcccca tcatatagga gtttatctaa gggaaactcc    180
accttcactg cccacaccca tatgccccgc aactgctata actctgccac tctttgcatg    240
catgcaaata ctcattattg gacagggaaa atgattaatc ctagttgtcc tggaggactt    300
ggagccactg tctgttggac ttacttcacc cataccagta tgtctgatgg gggtggaatt    360
caaggtcagg caagagaaaa acaagtaaag gaagcaatct cccaactgac ccggggacat    420
agcaccccta gcccctacaa aggactagtt ctctcaaaac tacatgaaac cctccgtacc    480
catactcgcc tggtgagcct atttaatacc accctcactc ggctccatga ggtctcagcc    540
caaaacccta ctaactgttg gatgtgcctc cccctgcact tcaggccata catttcaatc    600
cctgttcctg aacaatggaa caacttcagc acagaaataa acaccacttc cgttttagta    660
ggacctcttg tttccaatct ggaaataacc catacctcaa acctcacctg tgtaaaattt    720
agcaatacta tagacacaac cagctcccaa tgcatcaggt gggtaacacc tcccacacga    780
atagtctgcc taccctcagg aatatttttt gtctgtggta cctcagccta tcattgtttg    840
aatggctctt cagaatctat gtgcttcctc tcattcttag tgccccctat gaccatctac    900
actgaacaag atttatacaa tcatgtcgta cctaagcccc acaacaaaag agtacccatt    960
cttccttttg ttatcagagc aggagtgcta ggcagactag gtactggcat tggcagtatc   1020
```

-continued

```
acaacctcta ctcagttcta ctacaaacta tctcaagaaa taaatggtga catggaacag   1080
gtcactgact ccctggtcac cttgcaagat caacttaact ccctagcagc agtagtcctt   1140
caaaatcgaa gagctttaga cttgctaacc gccaaaagag ggggaacctg tttattttta   1200
ggagaagaac gctgttatta tgttaatcaa tccagaattg tcactgagaa agttaaagaa   1260
attcgagatc gaatacaatg tagagcagag gagcttcaaa acaccgaacg ctggggcctc   1320
ctcagccaat ggatgccctg ggttctcccc ttcttaggac ctctagcagc tctaatattg   1380
ttactcctct ttggaccctg tatctttaac ctccttgtta agtttgtctc ttccagaatt   1440
gaagctgtaa agctacagat ggtcttacaa atggaacccc agatggagtc catgactaag   1500
atccaccgtg gacccctgga ccggcctgct agcccatgct ccgatgttaa tgacattgaa   1560
ggcacccctc ccgaggaaat ctcaactgca caacccctac tatgccccaa ttcagcggga   1620
agcagttaga gcggtcatca gccaacctcc ccaacagcac ttgggttttc ctgttgagag   1680
gggggactga gagacaggac tagctggatt tcctaggcca acgaagaatc cctaagccta   1740
gctgggaagg tgactgcatc cacctctaaa catggggctt gcaacttagc tcacacccga   1800
ccaatcagag agctcactaa aatgctaatt aggcaaaaat aggaggtaaa gaaatagcca   1860
atcatctatt gcctgagagc acagcgggag ggacaaggat cgggatataa acccaggcat   1920
tcgagccggc aacggcaacc ccctttgggt cccctccctt tgtatgggcg ctctgttttc   1980
actctatttc actctattaa atcttgcaac tgaaaaaaaa aaaaaaaaaa              2030
```

```

<210> SEQ ID NO 43
<211> LENGTH: 2055
<212> TYPE: DNA
<213> ORGANISM: MSRV

<400> SEQUENCE: 43
```

```
cagcaacccc ctttgggtcc cctcccattg tatgggagct ctgttttcac tctatttcac     60
tctattaaat catgcaactg cactcttctg gtccgtgttt tttatggctc aagctgagct    120
tttgttcgcc atccaccact gctgtttgcc accgtcacag acccgctgct gacttccatc    180
cctttggatc cagcagagtg tccgctgtgc tcctgatcca gcacaggcgc ccattgcctc    240
tcccaattgg gctaaaggct tgccattgtt cctgcacagc taagtgcctg ggttcatcct    300
aatcgagctg aacactagtc actgggttcc acggttctct tccatgaccc atggcttcta    360
atagagctat aacactcact gcatggtcca agattccatt ccttggaatc cgtgagacca    420
agaaccccag gtcagagaac acaaggcttg ccaccatgtt ggaagcagcc caccaccatt    480
ttggaagcag cccgccacta tcttgggagc tctgggagca aggaccccag gtaacaattt    540
ggtgaccacg aagggacctg aatccgcaac catgaaggga tctccaaagc aatgggaaac    600
gttccccccg aggcaaaaat gcccctagaa cgtattctgg agaattggga ccaatgtgac    660
actcagacgc taagaaagaa acgatttata ttcttctgca gtaccgcctg gccacaatat    720
cctcttcaag ggagagaaac ctggcttcct gagggaagta taaattataa catcatctta    780
cagctagacc tcttctgtag aaaggagggc aaatggagtg aagtgccata tgtgcaaact    840
ttcttttcat taagagacaa ctcacaatta tgtaaaaagt gtggtttatg ccctacagga    900
agccctcaga gtccacctcc ctaccccagc gtcccctccc cgactccttc ctcaactaat    960
aaggaccccc ctttaaccca aacggtccaa aaggagatag acaaaggggt aaacaatgaa   1020
ccaaagagtg ccaatattcc ccgattatgc cccctccaag cagtgagagg aggagaattc   1080
ggcccagcca gagtgcctgt accttttct ctctcagact taaagcaaat taaaatagac   1140
```

```
ctaggtaaat tctcagataa ccctgacggc tatattgatg ttttacaagg gttaggacaa   1200
tcctttgatc tgacatggag agatataatg ttactactaa atcagacact aaccccaaat   1260
gagagaagtg ccgctgtaac tgcagcccga gagtttggcg atctttggta tctcagtcag   1320
gccaacaata ggatgacaac agaggaaaga acaactccca caggccagca ggcagttccc   1380
agtgtagacc ctcattggga cacagaatca gaacatggag attggtgcca caaacatttg   1440
ctaacttgcg tgctagaagg actgaggaaa actaggaaga agcctatgaa ttactcaatg   1500
atgtccacta aacacaggg aaaggaagaa aatcttactg cttttctgga cagactaagg   1560
gaggcattga ggaagcatac ctccctgtca cctgactcta ttgaaggcca actaatctta   1620
aaggataagt ttatcactca gtcagctgca gacattagaa aaaaacttca aaagtccgtc   1680
ttaggctcgg aacaaaactt agaaacccta ttgaacttgg caacctcggt tttttataat   1740
agagatcagg aggagcaggc agaatgggac aaatgggata aaaaaaaaag ggccaccgct   1800
ttagtcatgg ccctcaggca agcggacttt ggaggctctg gaaagggaa aagctgggca    1860 aataggaagc ctaatagggc ttgcttccag tgcggtctac aaggacactt taaaaagat    1920 tgtccaaata gaaataagcc gccccttgt ccatgcccct tacgtcaagg gaatcactgg    1980
aaggcccact gccccagggg atcaagatac tctgagtcag aagccattaa ccagatgatc   2040
cagcagcagg actga                                                   2055

<210> SEQ ID NO 44
<211> LENGTH: 1197
<212> TYPE: DNA
<213> ORGANISM: MSRV

<400> SEQUENCE: 44
ggacccgtag tatggggtaa tcccctccgg gaaaccaagc cccagtactc agaagaagaa     60
atagaatggg gaacctcacg aggacatggt ttcctcccct caggatggct agccactgaa    120
gaaggaaaaa tacttttgct ggcagctaac caatggaaat tacttaaaac ccttcagcaa    180
accttccact taggcattga tagcacccat cagatagcca aatcattatt tactggacca    240 ggcctttca aaactatcaa gcagatagtc agggcctgtg aagtgtgcca aagaaataat     300
cccctgcctt atcgccaagc tccttcagga gaacaaagaa caggcaatta cccaagagaa    360
gactggcaac tagattttat ccacatgcca aaatcacagg gatttcagtg tctactagtc    420
tgggtagata ctttcactgg ttgggcagag gccttcccct gtaggacaga aaagttccaa    480
gaggtaataa aggcactagt tcatgaagta attcccagat tcggacttcc ctgaggctta    540
cagagtgaca atggtcctgc tttcaaggcc acagtaaccc agggagtatc ccaggcgtta    600
ggtatagaat atcacttaca ctgcacctag aggccacaat cctcagggaa ggttgagaaa    660
atgaaaacac tcaaacgaca tctaaacaag ctaacccagg aaacccacct cgcatggtct    720
gctctgttgt ctatagcctt actaagaatc caaaactctc cccaaaaggc aggacttagc    780
ccatacagaa tgctgtatgg acggtccttc ctaaccaatg accttctgct tgaccaagag    840
atggccaact tagttgcaga catcacctcc ttagccaaat atcaacaagt tcttaaaaca    900
ttacaaggag cctgtccccg agaggaggga aaagaaatat tccaccctgg tgtcatggta    960
ttagtcaagt cccttccctc taattcccca tccctagaca catcctgggg aggaccctac   1020
ccagtcattt tatctatccc aactgcggtt aaagtggctg gagtggagtc ttggatacat   1080
cacactcgaa tcaaacccctg gatactgccg aaggaacccg aaaatccagg ggacaacgct   1140
agctatttct ttgaacctct agaggatctg tgcctgctct tcaagcaaca accgtga       1197
```

```
<210> SEQ ID NO 45
<211> LENGTH: 1718
<212> TYPE: DNA
<213> ORGANISM: MSRV

<400> SEQUENCE: 45
gagaatagca gcataagttg gctggcagaa gtagggaaag acagcaagaa gtaaagaaaa      60
aaaggagaaa gtcagagaaa gaaaaaaaga gaggaagaaa caagaagaa cttgaagaga     120 gaaagaagta gtaaagaaaa aacagtatac cctattcctt taaaagccag ggtaaatttc     180
tgtctaccta gccaaggcat attcttctta tgtggaacat caacctatat ctgcctcccc     240
actaactgga caggcaccag aaccttagtc tttctaagtc ccaacattaa cattgcccca     300
ggaaatcaga ccctattggt acctgtcaaa gctaaagtcc gtcagtgcag agccatacaa     360
ctaatatccc tatttatagg gttaggaatg gctactgcta caggaactgg aatagccggt     420
ttatctactt cattatccta ctaccataca ctctcaaaga atttctcaga cagtttgcaa     480
gaaataatga atctattct  tactttacaa tcccaattag actctttggc agcaatgact     540
ctccaaaacc gccgaggccc acacctcctc actgctgaga aggaggact ctgcaccttc      600 ttaggggaag agtgttgttt ttacactaac cagtcaggga tagtacgaga tgccacctgg     660
catttacagg aaagggcttc tgatatcaga caatgccttt caaactctta taccaacctc     720
tggagttggg caacatggct tcttccattt ctaggtccca tggcagccat cttgctgtta     780
ctcacctttg ggccctgtat ttttaagctt cttgtcaaat ttgtttcctc taggatcgaa     840
gccatcaagc tacagatggt cttacaaatg gaaccccaaa tgagttcaac taacaacttc     900
taccaaggac ccctggaacg atccactggc acttccacta gcctagagat tcccctctgg     960
aagacactac aactgcaggg ccccttcttt gcccctatcc agcaggaagt agctagagcg    1020
gtcatcggcc aaattcccaa cagcagttgg ggtgtcctgt ttagagggg  gattgaagag    1080 tgacagcctg ctggcagcct cacagccctc gttggatctc agtgcctcct cagccttggt    1140
gcccactctg gccgtgcttg aggagccctt cagcctgcca ctgcactgtg ggagcctctt    1200
tctgggctgg acaaggccgg agccagctcc ctcagcttgc agggaggtat ggagggagag    1260
atgcaggcgg gaaccagggc tgcgcatggc gcttgcgggc cagcatgagt tccaggtggg    1320
cgtgggctcg gcgggcccca cactcgggca gtgaggggct tagcacctgg gccagacaga    1380
tgctgtgctc aacttcttcg ctgggcctta gctgccttcc ccgtggggca gggctacggg    1440
aacatgcagc ctgcccatgc ttgagcccc  caccccgccg tgggttcytg cacagcccaa    1500
gcttcccgga caagcaccac cccttatcca cggtgcccag tcccatcaac cacccaaggg    1560
ttgaggagtg cgggcacaca gcgcgggatt ggcaggcagt tccacttgcg gccttggtgc    1620
gggatccact gcgtgaagcc agctgggctc ctgagtctgg tggggacttg gagaatcttt    1680
atgtctagct aagggattgt aaatacacca atcagcac                            1718
```